United States Patent
Shin et al.

(10) Patent No.: US 12,084,439 B2
(45) Date of Patent: Sep. 10, 2024

(54) COMPOUND AND PHOTOELECTRIC DEVICE, IMAGE SENSOR, AND ELECTRONIC DEVICE INCLUDING THE SAME

(71) Applicant: Samsung Electronics Co., Ltd., Suwon-si (KR)

(72) Inventors: Jisoo Shin, Suwon-si (KR); Chul Baik, Suwon-si (KR); Taejin Choi, Suwon-si (KR); Sung Young Yun, Suwon-si (KR); Kyung Bae Park, Hwaseong-si (KR); Gae Hwang Lee, Seongnam-si (KR); Yeong Suk Choi, Suwon-si (KR); Chul Joon Heo, Busan (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 696 days.

(21) Appl. No.: 17/163,712

(22) Filed: Feb. 1, 2021

(65) Prior Publication Data
US 2021/0246134 A1   Aug. 12, 2021

(30) Foreign Application Priority Data

Jan. 31, 2020   (KR) .................. 10-2020-0011925

(51) Int. Cl.
| C07D 471/04 | (2006.01) |
| H10K 85/60 | (2023.01) |
| H10K 30/20 | (2023.01) |
| H10K 30/81 | (2023.01) |

(52) U.S. Cl.
CPC ....... C07D 471/04 (2013.01); H10K 85/6572 (2023.02); H10K 85/6574 (2023.02); H10K 30/20 (2023.02); H10K 30/81 (2023.02)

(58) Field of Classification Search
CPC .................................. C07D 471/04
See application file for complete search history.

(56) References Cited

U.S. PATENT DOCUMENTS

| 4,579,799 A | 4/1986 | Katagiri et al. |
| 6,300,612 B1 | 10/2001 | Yu |
| 7,129,466 B2 | 10/2006 | Iwasaki |
| 7,973,307 B2 | 7/2011 | Rand et al. |
| 8,035,708 B2 | 10/2011 | Takizawa et al. |
| 8,426,727 B2 | 4/2013 | Pfeiffer et al. |
| 8,525,577 B2 | 9/2013 | Yofu et al. |
| 9,070,887 B2 | 6/2015 | Yofu et al. |
| 9,666,810 B2 | 5/2017 | Yun et al. |
| 9,786,847 B2 | 10/2017 | Lim et al. |
| 9,818,956 B2 | 11/2017 | Ro et al. |
| 9,941,477 B2 | 4/2018 | Choi et al. |
| 10,236,449 B2 | 3/2019 | Yun et al. |
| 10,244,486 B2 | 3/2019 | Lee |
| 10,276,802 B2 | 4/2019 | Shibuya et al. |
| 10,326,083 B2 | 6/2019 | Yagi et al. |
| 10,461,256 B2 | 10/2019 | Choi et al. |
| 10,566,544 B2 | 2/2020 | Shibuya et al. |
| 2005/0049267 A1* | 3/2005 | Suto ............ C07D 405/06 514/270 |
| 2007/0012955 A1 | 1/2007 | Ihama |
| 2009/0085029 A1 | 4/2009 | Mitsui et al. |
| 2010/0137388 A1 | 6/2010 | Barden et al. |
| 2012/0313088 A1 | 12/2012 | Yofu et al. |

FOREIGN PATENT DOCUMENTS

| EP | 3243822 A1 | 11/2017 |
| EP | 3473622 A1 | 4/2019 |
| JP | 2005-132914 A | 5/2005 |
| JP | 2014-082483 A | 5/2014 |
| KR | 2016-0046567 A | 4/2016 |
| KR | 2016-0052448 A | 5/2016 |
| KR | 2016-0062527 A | 6/2016 |
| KR | 10-1676041 B1 | 11/2016 |
| KR | 2017-0037390 A | 4/2017 |
| KR | 2017-0060488 A | 6/2017 |
| KR | 2017-0114839 A | 10/2017 |
| KR | 2017-0126753 A | 11/2017 |
| KR | 2017-0137648 A | 12/2017 |

OTHER PUBLICATIONS

Teimuri-Mofrad, Res. on Chem. Intermed., vol. 42, No. 10 (2016) pp. 7501-7511.*
Sun et al., Crystallography Reports, vol. 61, No. 7, Nov. 2016 pp. 1072-1076.*

(Continued)

*Primary Examiner* — Paul V Ward
(74) *Attorney, Agent, or Firm* — Harness, Dickey & Pierce, P.L.C.

(57) ABSTRACT

A compound of Chemical Formula 1, and an organic photoelectric device, an image sensor, and an electronic device including the same are disclosed:

[Chemical Formula 1]

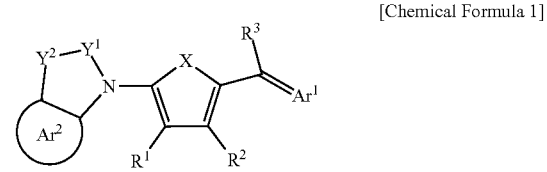

In Chemical Formula 1, each substituent is the same as defined in the detailed description.

28 Claims, 10 Drawing Sheets

(56) References Cited

OTHER PUBLICATIONS

Heichert et al., J'nal of Chem Sci. vol. 71, No. 10, Apr. 2016 pp. 651-658.*

Jin Seok Hong et al., '(N-7-Azaindolyl)oligothiophenes: synthesis, characterization, and photophysical properties' *Tetrahedron*, vol. 63, Jun. 2007, pp. 8761-8769.

Extended European Search Report dated Apr. 6, 2021, issued in corresponding European Patent Application No. 21154575.1.

S.-W. Sun et al., 'Synthesis of 2-Arylidenebenzocycloalkanones Containing N-Donor Heterocyclic Rings' *Crystallography Reports*, vol. 61, No. 7, Nov. 2016, pp. 1072-1076.

Christoph Heichert and Horst Hartmann, 'Synthesis and characterisation of long wavelength-absorbing donor/acceptor-substituted methine dyes' *Zeitschrift Fur Naturforschung—Section B Journal of Chemical Sciences* vol. 71, No. 6, Jan. 2016, pp. 651-658.

Reza Teimuri-Mofrad et al., 'A convenient and efficient method for the synthesis of new 2-(4-amino substituted benzilidine) indanone derivatives' *Research on Chemical Intermediates*, vol. 42, No. 10, Apr. 2016, pp. 7501-7511.

Timothy Mckee et al., 'Pin1-modulating compounds and methods of use thereof IN-IT' *Chemical Abstracts Service*, XP055790176, * 600690-55-9* *600691-14-3*RL, CAPLUS, 2003.

Hokuto Seo et al., 'Color Sensors with Three Vertically Stacked Organic Photodetectors' *Japanese Journal of Applied Physics*, vol. 46, No. 49, 2007, pp. L1240-L1242.

Satoshi Aihara et al., 'Stacked Image Sensor With Green- and Red-Sensitive Organic Photoconductive Films Applying Zinc Oxide Thin-Film Transistors to a Signal Readout Circuit' *IEEE Transactions on Electron Devices*, vol. 56, No. 11, Nov. 2009, pp. 2570-2576.

Mikio Ihama et al., 'CMOS Image Sensor with a Thin Overlaid Panchromatic Organic Photoconductive Layer for Sensors with Reduced Pixel Size' INP 1-4, *IDW* 2009, pp. 2123-2126.

Seon-Jeong Lim et al. 'Organic-on-silicon complementary metal-oxide-semiconductor colour image sensors' *Scientific Reports*, 5:7708, Jan. 2015.

Juha Alakarhu, 'Image Sensors and Image Quality in Mobile Phones' *International Image Sensor Workshop*, Jun. 2007.

Kazuko Takahashi et al., 'Efficient Synthesis of 2-IODO and 2-Dicyanomethyl Derivitives of Thiophene, Selenophene, Tellurophene, and Thieno[3,2-b]Thiophene' *Heterocycles*, vol. 43, No. 9, 1996, pp. 1927-1935.

* cited by examiner

COMPOUND AND PHOTOELECTRIC DEVICE, IMAGE SENSOR, AND ELECTRONIC DEVICE INCLUDING THE SAME

CROSS-REFERENCE TO RELATED APPLICATION

This application claims priority to and the benefit of Korean Patent Application No. 10-2020-0011925, filed in the Korean Intellectual Property Office on Jan. 31, 2020, the entire contents of which are incorporated herein by reference.

BACKGROUND

1. Field

Example embodiments provide a compound and a photoelectric device, an image sensor, and an electronic device including the same.

2. Description of Related Art

A photoelectric device converts light into an electrical signal using photoelectric effects. The photoelectric device may include a photodiode, a phototransistor, and the like, and it may be applied to an image sensor, an organic light emitting diode, and the like.

An image sensor including a photodiode requires high resolution and thus a small pixel. At present, a silicon photodiode is widely used, but it has a problem of deteriorated sensitivity since silicon photodiode has a smaller absorption area due to small pixels. Accordingly, an organic material that is capable of replacing silicon has been researched.

The organic material has a high extinction coefficient and selectively absorbs light in a particular wavelength region depending on a molecular structure, and thus may simultaneously replace a photodiode and a color filter and resultantly improve sensitivity and contribute to high integration.

SUMMARY

Example embodiments provide a compound capable of selectively absorbing light in a green wavelength region and/or having improved thermal stability.

Example embodiments also provide a photoelectric device capable of selectively absorbing light in the green wavelength region and/or maintaining good efficiency even under high temperature conditions.

Example embodiments also provide an image sensor including the photoelectric device.

Example embodiments also provide an electronic device including the image sensor.

According to example embodiments, a compound is represented by Chemical Formula 1.

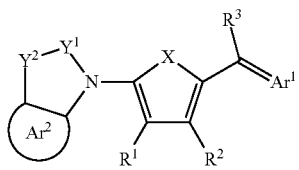

[Chemical Formula 1]

In Chemical Formula 1, $Ar^1$ is a substituted or unsubstituted C6 to C30 hydrocarbon cyclic group having at least one functional group selected from C=O, C=S, C=Se, and C=Te, a substituted or unsubstituted C6 to C30 heterocyclic group having at least one functional group selected from C=O, C=S, C=Se, and C=Te, or a fused ring thereof, $Ar^2$ is a substituted or unsubstituted C6 to C30 arene group, a substituted or unsubstituted C3 to C30 heteroarene group, or a condensed ring thereof, X is —O—, —S—, —Se—, —Te—, —S(=O)—, —S(=O)$_2$—, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^d$, R$^e$, R$^f$, R$^g$, R$^h$, and R$^i$ are independently hydrogen or a substituted or unsubstituted C1 to C10 alkyl group, and n is an integer of 1 or 2, $R^1$ to $R^3$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —SiR$^a$R$^b$R$^c$, wherein R$^a$, R$^b$, and R$^c$ are independently hydrogen or a substituted or unsubstituted C1 to C10 alkyl group, or a combination thereof, and $Y^1$ and $Y^2$ are independently —NR$^{a1}$—, —N=, —O—, —S—, —Se—, —Te—, —(CR$^{a2}$)=, or —(CR$^{a3}$R$^{a4}$)$_n$—, provided that both $Y^1$ and $Y^2$ are not —NR$^{a1}$—, —N=, —O—, —S—, —Se—, or —Te—, or —Y$^1$—Y$^2$— is —(C(R$^{a5}$)=C(R$^{a6}$))—, wherein R$^{a1}$, R$^{a2}$, R$^{a3}$, R$^{a4}$, R$^{a5}$, and R$^{a6}$ are independently hydrogen or a C1 to C10 alkyl group, and n is an integer of 1 or 2.

In some embodiments, in Chemical Formula 1, a fused ring of the Ar$^2$ ring and the N—Y$^1$-Y$^2$-containing ring may be represented by Chemical Formula 2A or Chemical Formula 2B.

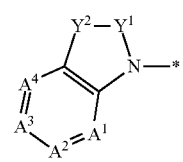

[Chemical Formula 2A]

In Chemical Formula 2A, $Y^1$ and $Y^2$ are independently —NR$^{a1}$—, —N=, —O—, —S—, —Se—, —Te—, —(CR$^{a2}$)=, or —(CR$^{a3}$R$^{a4}$)$_n$—, provided that both $Y^1$ and $Y^2$ are not —NR$^{a1}$—, —N=, —O—, —S—, —Se—, or —Te—, or —Y$^1$—Y$^2$— is —(C(R$^{a5}$)=C(R$^{a6}$))—, wherein R$^{a1}$, R$^{a2}$, R$^{a3}$, R$^{a4}$, R$^{a5}$, and R$^{a6}$ are independently hydrogen or a C1 to C10 alkyl group, and n is an integer of 1 or 2, and $A^1$ to $A^4$ are independently N or CR$^x$, wherein R$^x$ is hydrogen, a halogen, a cyano group, or a substituted or unsubstituted C1 to C10 alkyl group.

[Chemical Formula 2B]

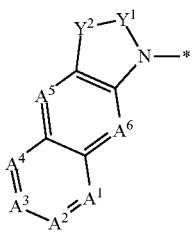

In Chemical Formula 2B,
$Y^1$ and $Y^2$ are independently —$NR^{a1}$—, —N=, —O—, —S—, —Se—, —Te—, —($CR^{a2}$)=, or —($CR^{a3}R^{a4}$)$_n$—, provided that both $Y^1$ and $Y^2$ are not —$NR^{a1}$—, —N=, —O—, —S—, —Se—, or —Te—, or —$Y^1$—$Y^2$— is —($C(R^{a5})$=$C(R^{a6})$)—, wherein $R^{a1}$, $R^{a2}$, $R^{a3}$, $R^{a4}$, $R^{a5}$, and $R^{a6}$ are independently hydrogen or a C1 to C10 alkyl group, and n is an integer of 1 or 2, and $A^1$ to $A^6$ are independently N or $CR^x$, wherein $R^x$ is hydrogen, a halogen, a cyano group, or a C1 to C10 alkyl group.

In some embodiments, at least one of $A^1$ to $A^4$ in Chemical Formula 2A may be N.

In some embodiments, in Chemical Formula 2A, two of $A^1$ to $A^4$ that are adjacent to each other may be linked to each other to provide a fused aromatic ring.

In some embodiments, at least one of $A^1$ to $A^6$ in Chemical Formula 2B may be N.

In some embodiments, in Chemical Formula 2B, two of $A^1$ to $A^4$ that are adjacent to each other may be linked to each other to provide a fused aromatic ring.

In some embodiments, Chemical Formula 2A may be represented by one of Chemical Formulas 2A-1 to 2A-5.

[Chemical Formula 2A-1]

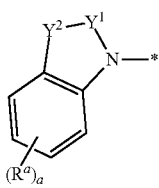

[Chemical Formula 2A-2]

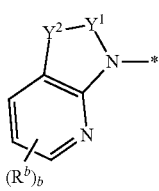

[Chemical Formula 2A-3]

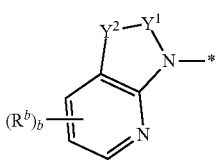

[Chemical Formula 2A-4]

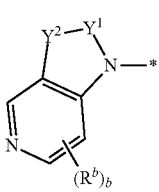

[Chemical Formula 2A-5]

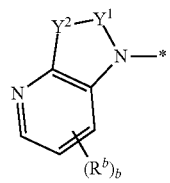

In Chemical Formulas 2A-1 to 2A-5,
$Y^1$ and $Y^2$ are independently —$NR^{a1}$—, —N=, —O—, —S—, —Se—, —Te—, —($CR^{a2}$)=, or —($CR^{a3}R^{a4}$)$_n$—, provided that both $Y^1$ and $Y^2$ are not —$NR^{a1}$—, —N=, —O—, —S—, —Se—, or —Te—, or —$Y^1$—$Y^2$— is —($C(R^{a5})$=$C(R^{a6})$)—, wherein $R^{a1}$, $R^{a2}$, $R^{a3}$, $R^{a4}$, $R^{a5}$, and $R^{a6}$ are independently hydrogen or a C1 to C10 alkyl group, and n is an integer of 1 or 2, $R^a$ is hydrogen or a substituted or unsubstituted C1 to C10 alkyl group, a is an integer of 1 to 4, $R^b$ is hydrogen or a substituted or unsubstituted C1 to C10 alkyl group, and b is an integer of 1 to 3.

In some embodiments, Chemical Formula 2A may be represented by one of Chemical Formulas 2A-6 to 2A-10.

[Chemical Formula 2A-6]

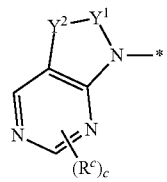

[Chemical Formula 2A-7]

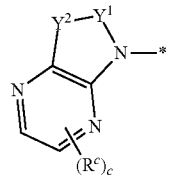

[Chemical Formula 2A-8]

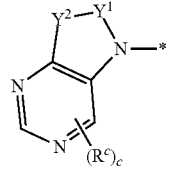

[Chemical Formula 2A-9]

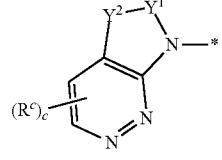

[Chemical Formula 2A-10]

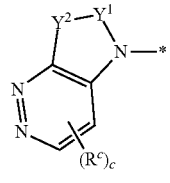

In Chemical Formulas 2A-6 to 2A-10, $Y^1$ and $Y^2$ are independently —$NR^{a1}$—, —N═, —O—, —S—, —Se—, —Te—, —$(CR^{a2})$═, or —$(CR^{a3}R^{a4})_n$—, provided that both $Y^1$ and $Y^2$ are not —$NR^{a1}$—, —N═, —O—, —S—, —Se—, or —Te—, or —$Y^1$—$Y^2$— is —$(C(R^{a5})$═$C(R^{a6}))$—, wherein $R^{a1}$, $R^{a2}$, $R^{a3}$, $R^{a4}$, $R^{a5}$, and $R^{a6}$ are independently hydrogen or a C1 to C10 alkyl group, and n is an integer of 1 or 2, $R^c$ is hydrogen or a substituted or unsubstituted C1 to C10 alkyl group, and c is an integer of 1 or 2.

In some embodiments, Chemical Formula 2B may be represented by one of Chemical Formulas 2B-1 to 2B-5.

[Chemical Formula 2B-1]

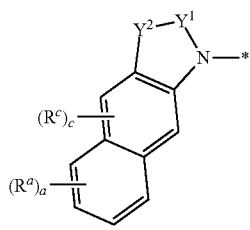

[Chemical Formula 2B-2]

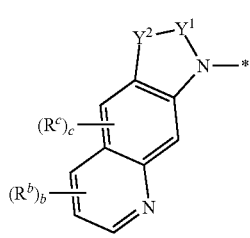

[Chemical Formula 2B-3]

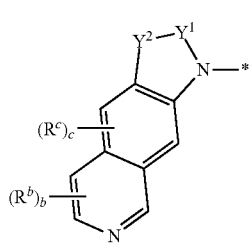

[Chemical Formula 2B-4]

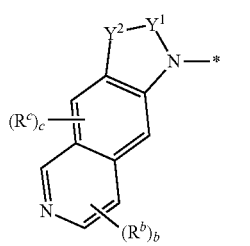

[Chemical Formula 2B-5]

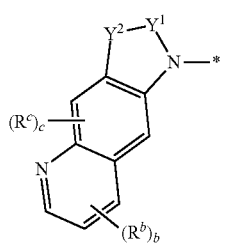

In Chemical Formulas 2B-1 to 2B-5, $Y^1$ and $Y^2$ are independently —$NR^{a1}$—, —N═, —O—, —S—, —Se—, —Te—, —$(CR^{a2})$═, or —$(CR^{a3}R^{a4})_n$—, provided that both $Y^1$ and $Y^2$ are not —$NR^{a1}$—, —N═, —O—, —S—, —Se—, or —Te—, or —$Y^1$—$Y^2$— is —$(C(R^{a5})$═$C(R^{a6}))$—, wherein $R^{a1}$, $R^{a2}$, $R^{a3}$, $R^{a4}$, $R^{a5}$, and $R^{a6}$ are independently hydrogen or a C1 to C10 alkyl group, and n is an integer of 1 or 2, $R^a$ is hydrogen or a substituted or unsubstituted C1 to C10 alkyl group, a is an integer of 1 to 4, $R^b$ is hydrogen or a substituted or unsubstituted C1 to C10 alkyl group, b is an integer of 1 to 3, $R^c$ is hydrogen or a substituted or unsubstituted C1 to C10 alkyl group, and c is an integer of 1 or 2.

In some embodiments, Chemical Formula 2B may be represented by one of Chemical Formulas 2B-6 to 2B-10.

[Chemical Formula 2B-6]

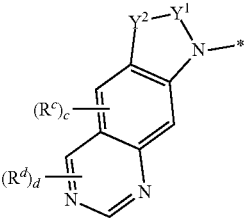

[Chemical Formula 2B-7]

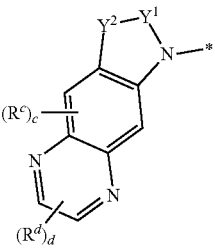

[Chemical Formula 2B-8]

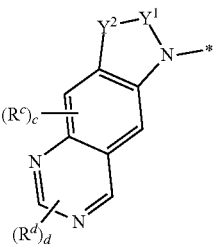

[Chemical Formula 2B-9]

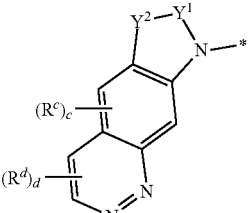

[Chemical Formula 2B-10]

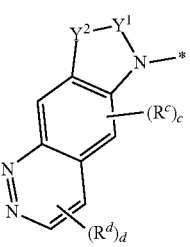

In Chemical Formulas 2B-6 to 2B-10, $Y^1$ and $Y^2$ are independently —$NR^{a1}$—, —N=, —O—, —S—, —Se—, —Te—, —$(CR^{a2})$=, or —$(CR^{a3}R^{a4})_n$—, provided that both $Y^1$ and $Y^2$ are not —$NR^{a1}$—, —N=, —O—, —S—, —Se—, or —Te—, or —$Y^1$—$Y^2$— is —$(C(R^{a5})$=$C(R^{a6}))$—, wherein $R^{a1}$, $R^{a2}$, $R^{a3}$, $R^{a4}$, $R^{a5}$, and $R^{a6}$ are independently hydrogen or a C1 to C10 alkyl group, and n is an integer of 1 or 2, and $R^c$ is hydrogen or a substituted or unsubstituted C1 to C10 alkyl group, c is an integer of 1 or 2, $R^d$ is hydrogen or a substituted or unsubstituted C1 to C10 alkyl group, and d is an integer of 1 or 2.

In some embodiments, in Chemical Formula 1, $Ar^1$ may be a cyclic group represented by Chemical Formula 3.

[Chemical Formula 3]

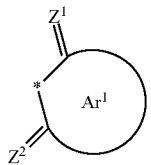

In Chemical Formula 3, $Ar'^1$ is a substituted or unsubstituted C6 to C30 aryl group or a substituted or unsubstituted C3 to C30 heteroaryl group, $Z^1$ is O, S, Se, or Te, and $Z^2$ is O, S, Se, Te, or $CR^aR^b$, wherein $R^a$ and $R^b$ are independently hydrogen, a substituted or unsubstituted C1 to C10 alkyl group, a cyano group or a cyano-containing group, provided that when $Z^2$ is $CR^aR^b$, at least one of $R^a$ and $R^b$ is a cyano group or a cyano-containing group.

In some embodiments, in Chemical Formula 1, $Ar^1$ may be a cyclic group represented by one of Chemical Formula 4A to Chemical Formula 4F.

[Chemical Formula 4A]

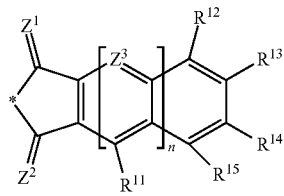

In Chemical Formula 4A, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group or a cyano-containing group, provided that when $Z^2$ is $CR^aR^b$, at least one of $R^a$ and $R^b$ is a cyano group or a cyano-containing group, $Z^3$ is N or $CR^0$, wherein $R^c$ is hydrogen, deuterium, or a substituted or unsubstituted C1 to C10 alkyl group, $R^{11}$, $R^{12}$, $R^{13}$, $R^{14}$, and $R^{15}$ are the same or different and are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof or $R^{12}$ and $R^{13}$ and $R^{14}$ and $R^{15}$ are independently present and are linked to each other to provide a fused aromatic ring, n is 0 or 1, and

* is a linking point.

[Chemical Formula 4B]

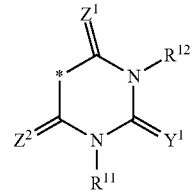

In Chemical Formula 4B, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group or a cyano-containing group, provided that when $Z^2$ is $CR^aR^b$, at least one of $R^a$ and $R^b$ is a cyano group or a cyano-containing group, $Y^1$ is O, S, Se, Te, or $C(R^a)(CN)$, wherein $R^a$ is hydrogen, a cyano group (—CN), or a C1 to C10 alkyl group, $R^{11}$ and $R^{12}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking point.

[Chemical Formula 4C]

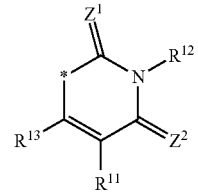

In Chemical Formula 4C, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group or a cyano-containing group, provided that when $Z^2$ is $CR^aR^b$, at least one of $R^a$ and $R^b$ is a cyano group or a cyano-containing group, $R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking point.

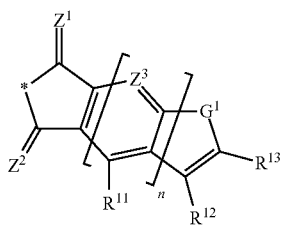

[Chemical Formula 4D]

In Chemical Formula 4D,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group or a cyano-containing group, provided that when $Z^2$ is $CR^aR^b$, at least one of $R^a$ and $R^b$ is a cyano group or a cyano-containing group,
$Z^3$ is N or $CR^c$, wherein $R^c$ is hydrogen or a substituted or unsubstituted C1 to C10 alkyl group,
$G^1$ is —O—, —S—, —Se—, —Te—, —$SiR^xR^y$—, or —$GeR^zR^w$—, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group,
$R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, $R^{12}$ and $R^{13}$ may independently be present or may be linked to each other to provide a fused aromatic ring,
n is 0 or 1, and
* is a linking point.

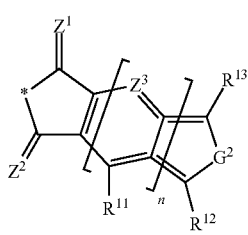

[Chemical Formula 4E]

In Chemical Formula 4E,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group or a cyano-containing group, provided that when $Z^2$ is $CR^aR^b$, at least one of $R^a$ and $R^b$ is a cyano group or a cyano-containing group,
$Z^3$ is N or $CR^c$, wherein $R^c$ is hydrogen or a substituted or unsubstituted C1 to C10 alkyl group,
$G^2$ is —O—, —S—, —Se—, —Te—, —$SiR^xR^y$—, or —$GeR^zR^w$—, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group,
$R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof,
n is 0 or 1, and
* is a linking point.

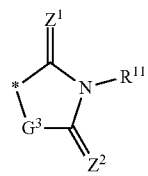

[Chemical Formula 4F]

In Chemical Formula 4F,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group or a cyano-containing group, provided that when $Z^2$ is $CR^aR^b$, at least one of $R^a$ and $R^b$ is a cyano group or a cyano-containing group,
$R^{11}$ is hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and
$G^3$ is —O—, —S—, —Se—, —Te—, —$SiR^xR^y$—, or —$GeR^zR^w$—, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group.

In some embodiments, $Z^1$ and $Z^2$ may be the same in Chemical Formula 4A to Chemical Formula 4F.

In some embodiments, $Z^1$ and $Z^2$ may be different in Chemical Formula 4A to Chemical Formula 4F.

In some embodiments, $Ar^1$ in Chemical Formula 1 may be represented by one of Chemical Formula 4A, Chemical Formula 4D, or Chemical Formula 4E, and n may be 0 in Chemical Formula 4A, Chemical Formula 4D, and Chemical Formula 4E.

In some embodiments, $Ar^1$ in Chemical Formula 1 may be represented by one of Chemical Formula 4A, Chemical Formula 4D, or Chemical Formula 4E, and n may be 1 in Chemical Formula 4A, Chemical Formula 4D, and Chemical Formula 4E.

In some embodiments, the compound may have a maximum absorption wavelength (λmax) in a wavelength region of greater than or equal to about 500 nm and less than about 600 nm, in a thin film state.

In some embodiments, the compound may exhibit a light absorption curve having a full width at half maximum (FWHM) of about 50 nm to about 120 nm, in a thin film state.

In some embodiments, a difference between a melting point of the compound and a temperature (deposition temperature) at which 10% by weight of the initial weight is lost may be greater than or equal to about 10° C.

In some embodiments, $R^1$ to $R^3$ in Chemical Formula 1 independently may be hydrogen, deuterium, or a substituted or unsubstituted C1 to C30 alkyl group. X in Chemical Formula 1 may be Se or Te.

According to another embodiment, a photoelectric device (e.g., organic photoelectric device) includes a first electrode and a second electrode facing each other and an active layer interposed between the first electrode and the second electrode and including the compound represented by Chemical Formula 1.

According to another embodiment, an image sensor includes the photoelectric device.

The image sensor may include a semiconductor substrate integrated with a plurality of first photo-sensing devices configured to sense light in a blue wavelength region and a plurality of second photo-sensing devices configured to sense light in a red wavelength region, and the photoelectric device may be on the semiconductor substrate and may be selectively configured to sense light in a green wavelength region.

In some embodiments, the first photo-sensing devices and the second photo-sensing devices may be stacked in a vertical direction in the semiconductor substrate.

In some embodiments, the image sensor may further include a color filter layer including a blue filter configured to selectively transmit light in a blue wavelength region and a red filter configured to selectively transmit light in a red wavelength region. The color filter layer may be on the substrate.

In some embodiments, the image sensor may include a green photoelectric device which is the photoelectric device, a blue photoelectric device configured to selectively absorb light in a blue wavelength region, and a red photoelectric device configured to selectively absorb light in a red wavelength region that are stacked.

According to another embodiment, an electronic device includes the image sensor.

The compound may selectively absorb light in a green wavelength region and may have thermal stability. The compound improves efficiency by increasing wavelength selectivity of the green wavelength region and provides photoelectric devices, image sensors and electronic devices that do not deteriorate performance even at high temperature processes due to improved thermal stability.

DETAILED DESCRIPTION

Figure 1:
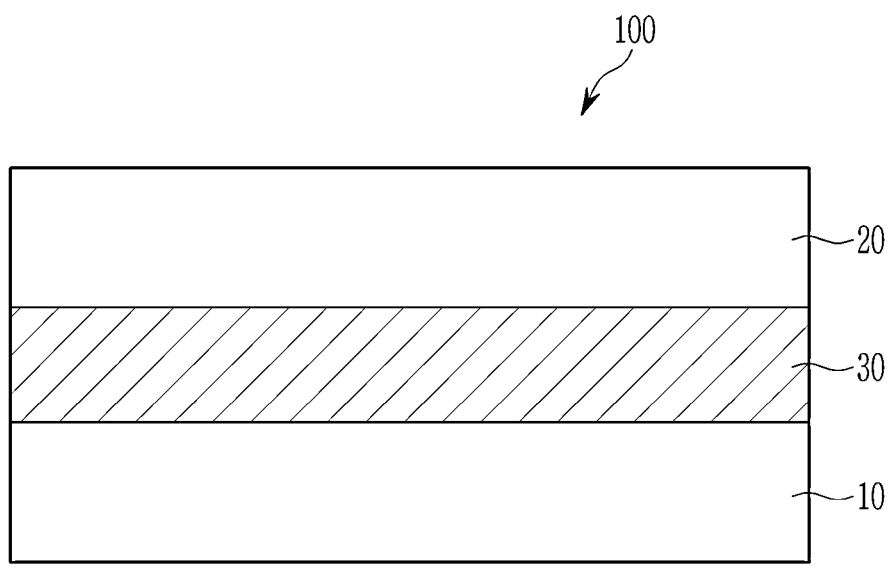
FIG. 1 is a cross-sectional view showing a photoelectric device according to an embodiment.

Hereinafter, embodiments are described in detail so that those of ordinary skill in the art can easily implement them. However, a structure that is actually applied may be implemented in various different forms, and is not limited to the embodiments described herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

As used herein, "at least one of A, B, or C," "one of A, B, C, or a combination thereof" and "one of A, B, C, and a combination thereof" refer to each constituent element, and a combination thereof (e.g., A; B; C; A and B; A and C; B and C; or A, B and C).

As used herein, when specific definition is not otherwise provided, "substituted" refers to replacement of a hydrogen of a compound or a functional group by a halogen atom (F, Br, Cl, or I), a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C20 alkyl group, a C1 to C20 alkoxy group, a C2 to C20 alkenyl group, a C2 to C20 alkynyl group, a C6 to C30 aryl group, a C7 to C30 arylalkyl group, a C2 to C20 heteroaryl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, $=$S, or a combination thereof.

As used herein, when specific definition is not otherwise provided, "hetero" refers to one including 1 to 3 heteroatoms selected from N, O, S, Se, Te, P, and S.

As used herein, "alkyl group" refers to a monovalent linear or branched saturated hydrocarbon group, for example a methyl group, an ethyl group, a propyl group, an isopropyl group, an n-butyl group, an isobutyl group, a t-butyl group, a pentyl group, a hexyl group, and the like.

As used herein, "cycloalkyl group" refers to a monovalent hydrocarbon cyclic group in which the atoms of the cycle are carbon, for example a cyclopropyl group, a cyclobutyl group, a cyclopentyl group, or a cyclohexyl group.

As used herein, "aryl group" refers to a substituent including all element of the functional group having p-orbitals which form conjugation, and may be a monocyclic, polycyclic or fused-ring polycyclic (e.g., rings sharing adjacent pairs of carbon atoms) functional group.

As used herein, when a definition is not otherwise provided, "cyano-containing group" refers to a monovalent group such as a C1 to C30 alkyl group, a C2 to C30 alkenyl group, or a C2 to C30 alkynyl group where at least one hydrogen is substituted with a cyano group. The cyano-containing group also refers to a divalent group such as =CR$^{x'}$—(CR$^x$R$^y$)$_p$—CR$^{y'}$(CN)$_2$ wherein R$^x$, R$^y$, R$^{x'}$, and R$^{y'}$ are independently hydrogen or a C1 to C10 alkyl group and p is an integer of 0 to 10 (or 1 to 10). Specific examples of the cyano-containing group may be a dicyanomethyl group, a dicyanovinyl group, a cyanoethynyl group, and the like. As used herein, the cyano-containing group does not include a functional group including a cyano group (—CN) alone.

As used herein, when a definition is not otherwise provided, "combination thereof" refers to at least two substituents bound to each other by a single bond or a C1 to C10 alkylene group, or at least two fused substituents.

As used herein, "hydrocarbon cyclic group" refers to a fused ring of an aromatic ring (arene ring) and a nonaromatic ring (alicyclic ring) and may include, for example a fused ring which is formed by linking at least one aromatic ring (arene ring) such as a C6 to C30 aryl group, a C6 to C20 aryl group, or a C6 to C10 aryl group with at least one nonaromatic ring (alicyclic ring) such as a C3 to C30 cycloalkyl group, a C3 to C20 cycloalkyl group, or a C3 to C10 cycloalkyl group.

As used herein, "heterocyclic group" refers to a cyclic group including a heteroatom selected from N, O, S, Se, Te, P, and Si instead of 1 to 3 carbon atoms in a cyclic group selected from an arene group (e.g., a C6 to C30 aryl group, a C6 to C20 aryl group, or a C6 to C10 aryl group), an alicyclic hydrocarbon group (e.g., a C3 to C30 cycloalkyl group, a C3 to C20 cycloalkyl group, or a C3 to C10 cycloalkyl group), or a fused ring thereof. At least one carbon atom of the heterocyclic group may also be substituted with a thiocarbonyl group (C=S).

As used herein, "arene group" refers to a hydrocarbon group having an aromatic ring, and includes monocyclic and polycyclic hydrocarbon groups, and the additional ring of the polycyclic hydrocarbon group may be an aromatic ring or a nonaromatic ring. "Heteroarene group" refers to an arene group including 1 to 3 heteroatoms selected from N, O, S, Se, Te, P, and Si in a cyclic group.

As used herein, "C6 to C30 aromatic hydrocarbon group" includes a C6 to C30 aryl group such as a phenyl group, a naphthyl group, a C6 to C30 arylene group, and the like, but is not limited thereto.

As used herein, "aliphatic hydrocarbon group" may include, for example, a C1 to C15 alkyl group such as a methyl group, an ethyl group, a propyl group, and the like, a C1 to C15 alkylene group, a C2 to C15 alkenyl group such as an ethenyl group or a propenyl group, a C2 to C15 alkynyl group such as an ethynyl group or a propynyl group, but is not limited thereto.

As used herein, "aromatic ring" refers to a C5 to C10 cyclic group (e.g., C6 aryl group) having a conjugation structure or a C2 to C10 heterocyclic group (e.g., C2 to C4 heteroaryl group) having a conjugation structure.

When the term "about" is used in this specification in connection with a numerical value, it is intended that the associated numerical value includes a manufacturing or operational tolerance (e.g., ±10%) around the stated numerical value.

Hereinafter, a compound according to an embodiment is described. The compound is represented by Chemical Formula 1.

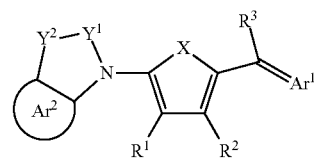

[Chemical Formula 1]

In Chemical Formula 1,

Ar$^1$ is a substituted or unsubstituted C6 to C30 hydrocarbon cyclic group having at least one functional group selected from C=O, C=S, C=Se, and C=Te, a substituted or unsubstituted C6 to C30 heterocyclic group having at least one functional group selected from C=O, C=S, C=Se, and C=Te, or a fused ring thereof, Ar$^2$ is a substituted or unsubstituted C6 to C30 arene group, a substituted or unsubstituted C3 to C30 heteroarene group, or a condensed ring thereof, X is —O—, —S—, —Se—, —Te—, —S(=O)—, —S(=O)$_2$—, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^d$, R$^e$, R$^f$, R$^g$, R$^h$, and R$^i$ are independently hydrogen or a substituted or unsubstituted C1 to C10 alkyl group, and n is an integer of 1 or 2, R$^1$ to R$^3$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ are independently hydrogen or a substituted or unsubstituted C1 to C10 alkyl group), or a combination thereof, and Y$^1$ and Y$^2$ are independently —NR$^{a1}$—, —N=, —O—, —S—, —Se—, —Te—, —(CR$^{a2}$)=, or —(CR$^{a3}$R$^{a4}$)$_n$—, provided that both Y$^1$ and Y$^2$ are not —NR$^{a1}$—, —N=, —O—, —S—, —Se—, or —Te—, or —Y$^1$—Y$^2$— is —(C(R$^{a5}$)=C(R$^{a6}$))—, wherein R$^{a1}$, R$^{a2}$, R$^{a3}$, R$^{a4}$, R$^{a5}$, and R$^{a6}$ are independently hydrogen or a C1 to C10 alkyl group, and n is an integer of 1 or 2.

The compound represented by Chemical Formula 1 includes an N-containing hetero aromatic ring having an asymmetric structure as an electron donor moiety, an X-containing linker, and an electron acceptor moiety represented by Ar$^1$.

In Chemical Formula 1, a fused ring of an Ar$^2$ ring and an N—Y$^1$-Y$^2$-containing ring is an electron donor moiety of an N-containing heteroaromatic ring and Y$^1$ and Y$^2$ do not form a fused ring, thereby providing an asymmetric structure. Such an asymmetric structure improves crystallinity of the compound and provides a planar structure, thereby improving charge mobility.

Ar$^2$ may be a substituted or unsubstituted C6 to C30 arene group, a substituted or unsubstituted C3 to C30 heteroarene group, or a condensed ring thereof, for example, a substituted or unsubstituted C6 to C20 arene group, a substituted or unsubstituted C3 to C20 heteroarene group, or a condensed ring thereof. When Ar$^2$ is a heteroarene group containing at least one hetero atom selected from nitrogen (N), sulfur (S) and selenium (Se), an intramolecular interaction of X of the linker; Z$^1$ and Z$^2$ (O, S, Se, or Te) present in the electron acceptor moiety; and the hetero atom included in $Ar^2$ may be increased and thus absorption intensity at a specific wavelength may be improved.

In an embodiment, the arene group may be a benzene ring, a naphthalene ring, and an anthracene ring. The heteroarene group may be a pyrrole ring, a pyrazole ring, an imidazole ring, an oxazole ring, an isoxazole ring, a thiazole ring, an isothiazole ring, a pyridine ring, a pyridazine ring, a pyrimidine ring, a pyrazine ring, an indole ring, a quinoline ring, an isoquinoline ring, a naphthyridine ring, a cinnoline ring, a quinazoline ring, a phthalazine ring, a benzotriazine ring, a pyridopyrazine ring, a pyridopyrimidine ring, a pyridopyridazine ring, a thiophene ring, a benzothiophene ring, a selenophene ring, or a benzoselenophene ring.

In Chemical Formula 1, the fused ring of the $Ar^2$ ring and the N—$Y^1$-$Y^2$-containing ring may be represented by Chemical Formula 2A or Chemical Formula 2B.

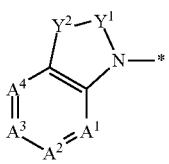

[Chemical Formula 2A]

In Chemical Formula 2A, $Y^1$ and $Y^2$ are independently —$NR^{a1}$—, —N=, —O—, —S—, —Se—, —Te—, —$(CR^{a2})$=, or —$(CR^{a3}R^{a4})_n$—, provided that both $Y^1$ and $Y^2$ are not —$NR^{a1}$—, —N=, —O—, —S—, —Se—, or —Te—, or —$Y^1$—$Y^2$— is —$(C(R^{a5})=C(R^{a6}))$—, wherein $R^{a1}$, $R^{a2}$, $R^{a3}$, $R^{a4}$, $R^{a5}$, and $R^{a6}$ are independently hydrogen or a substituted or an unsubstituted C1 to C10 alkyl group, and n is an integer of 1 or 2, and $A^1$ to $A^4$ are independently N or $CR^x$, wherein $R^x$ is hydrogen, a halogen, a cyano group, or a C1 to C10 alkyl group.

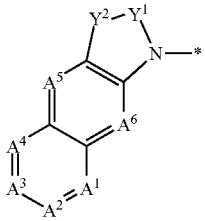

[Chemical Formula 2B]

In Chemical Formula 2B, $Y^1$ and $Y^2$ are independently —$NR^{a1}$—, —N=, —O—, —S—, —Se—, —Te—, —$(CR^{a2})$=, or —$(CR^{a3}R^{a4})_n$—, provided that both $Y^1$ and $Y^2$ are not —$NR^{a1}$—, —N=, —O—, —S—, —Se—, or —Te—, or —$Y^1$—$Y^2$— is —$(C(R^{a5})=C(R^{a6}))$—, wherein $R^{a1}$, $R^{a2}$, $R^{a3}$, $R^{a4}$, $R^{a5}$, and $R^{a6}$ are independently hydrogen or a C1 to C10 alkyl group, and n is an integer of 1 or 2, and $A^1$ to $A^6$ are independently N or $CR^x$, wherein $R^x$ is hydrogen, a halogen, a cyano group, or a substituted or unsubstituted C1 to C10 alkyl group.

In Chemical Formula 2A, at least one of $A^1$ to $A^4$, for example, two may be N.

In Chemical Formula 2A, two of $A^1$ to $A^4$ that are adjacent to each other may be linked to form a fused aromatic ring.

In Chemical Formula 2B, at least one of $A^1$ to $A^6$, for example, two may be N.

In Chemical Formula 2B, two of $A^1$ to $A^4$ that are adjacent to each other may be linked to form a fused aromatic ring.

Chemical Formula 2A may be represented by one of Chemical Formulas 2A-1 to 2A-5.

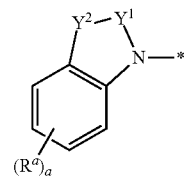

[Chemical Formula 2A-1]

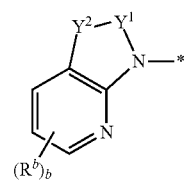

[Chemical Formula 2A-2]

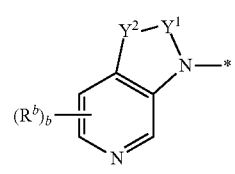

[Chemical Formula 2A-3]

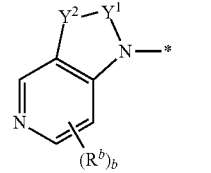

[Chemical Formula 2A-4]

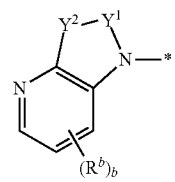

[Chemical Formula 2A-5]

In Chemical Formula 2A-1 to 2A-5, $Y^1$ and $Y^2$ are independently —$NR^{a1}$—, —N=, —O—, —S—, —Se—, —Te—, —$(CR^{a2})$=, or —$(CR^{a3}R^{a4})_n$—, provided that both $Y^1$ and $Y^2$ are not —$NR^{a1}$—, —N=, —O—, —S—, —Se—, or —Te—, or —$Y^1$—$Y^2$— is —$(C(R^{a5})=C(R^{a6}))$—, wherein $R^{a1}$, $R^{a2}$, $R^{a3}$, $R^{a4}$, $R^{a5}$, and $R^{a6}$ are independently hydrogen or a C1 to C10 alkyl group, and n is an integer of 1 or 2, and $R^a$ is hydrogen or a substituted or unsubstituted C1 to C10 alkyl group, a is an integer of 1 to 4, $R^b$ is hydrogen or a substituted or unsubstituted C1 to C10 alkyl group, and b is an integer of 1 to 3.

Chemical Formula 2A may be represented by one of Chemical Formulas 2A-6 to 2A-10.

[Chemical Formula 2A-6]

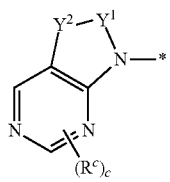

[Chemical Formula 2A-7]

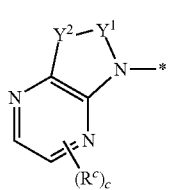

[Chemical Formula 2A-8]

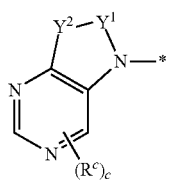

[Chemical Formula 2A-9]

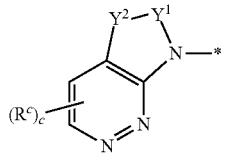

[Chemical Formula 2A-10]

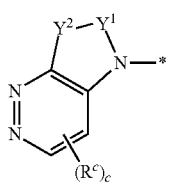

In Chemical Formulas 2A-6 to 2A-10, $Y^1$ and $Y^2$ are independently —$NR^{a1}$—, —N=, —O—, —S—, —Se—, —Te—, —$(CR^{a2})$=, or —$(CR^{a3}R^{a4})_n$—, provided that both $Y^1$ and $Y^2$ are not —$NR^{a1}$—, —N=, —O—, —S—, —Se—, or —Te—, or —$Y^1$—$Y^2$— is —$(C(R^{a5})$=$C(R^{a6}))$—, wherein $R^{a1}$, $R^{a2}$, $R^{a3}$, $R^{a4}$, $R^{a5}$, and $R^{a6}$ are independently hydrogen or a C1 to C10 alkyl group, and n is an integer of 1 or 2, $R^c$ is hydrogen or a substituted or unsubstituted C1 to C10 alkyl group, and c is an integer of 1 or 2.

Chemical Formula 2B may be represented by one of Chemical Formulas 2B-1 to 2B-5.

[Chemical Formula 2B-1]

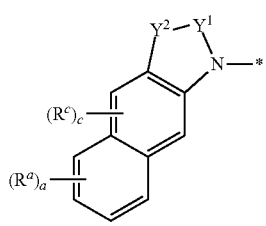

[Chemical Formula 2B-2]

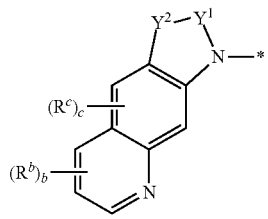

[Chemical Formula 2B-3]

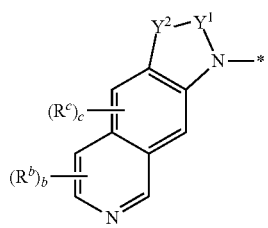

[Chemical Formula 2B-4]

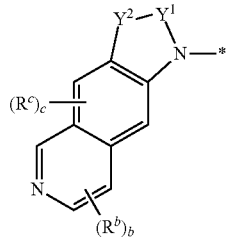

[Chemical Formula 2B-5]

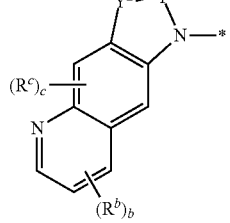

In Chemical Formulas 2B-1 to 2B-5, $Y^1$ and $Y^2$ are independently —$NR^{a1}$—, —N=, —O—, —S—, —Se—, —Te—, —$(CR^{a2})$=, or —$(CR^{a3}R^{a4})_n$—, provided that both $Y^1$ and $Y^2$ are not —$NR^{a1}$—, —N=, —O—, —S—, —Se—, or —Te—, or —$Y^1$—$Y^2$— is —$(C(R^{a5})$=$C(R^{a6}))$—, wherein $R^{a1}$, $R^{a2}$, $R^{a3}$, $R^{a4}$, $R^{a5}$, and $R^{a6}$ are independently hydrogen or a C1 to C10 alkyl group, and n is an integer of 1 or 2, $R^a$ is hydrogen or a substituted or unsubstituted C1 to C10 alkyl group, a is an integer of 1 to 4, $R^b$ is hydrogen or a substituted or unsubstituted C1 to C10 alkyl group, b is an integer of 1 to 3, $R^c$ is hydrogen or a substituted or unsubstituted C1 to C10 alkyl group, and c is an integer of 1 or 2.

Chemical Formula 2B may be represented by one of Chemical Formulas 2B-6 to 2B-10.

[Chemical Formula 2B-6]

[Chemical Formula 2B-7]

[Chemical Formula 2B-8]

[Chemical Formula 2B-9]

[Chemical Formula 2B-10]

In Chemical Formulas 2B-6 to 2B-10,
Y$^1$ and Y$^2$ are independently —NR$^{a1}$—, —N═, —O—, —S—, —Se—, —Te—, —(CR$^{a2}$)═, or —(CR$^{a3}$R$^{a4}$)$_n$—, provided that both Y$^1$ and Y$^2$ are not —NR$^{a1}$—, —N═, —O—, —S—, —Se—, or —Te—, or —Y$^1$—Y$^2$— is —(C(R$^{a5}$)═C(R$^{a6}$))—, wherein R$^{a1}$, R$^{a2}$, R$^{a3}$, R$^{a4}$, R$^{a5}$, and R$^{a6}$ are independently hydrogen or a C1 to C10 alkyl group, and n is an integer of 1 or 2, R$^c$ is hydrogen or a substituted or unsubstituted C1 to C10 alkyl group, c is an integer of 1 or 2, R$^d$ is hydrogen or a substituted or unsubstituted C1 to C10 alkyl group, and d is an integer of 1 or 2.

Chemical Formula 2A-1 may be one of functional groups represented by Chemical Formula 2A-1-1.

[Chemical Formula 2A-1-1]

In Chemical Formula 2A-1-1,
R$^a$, R$^{a1}$, R$^{a2}$, R$^{a3}$, R$^{a4}$, R$^{a5}$, and R$^{a6}$ are independently hydrogen or a C1 to C10 alkyl group, and a is an integer of 1 to 4.

Chemical Formula 2A-2 may be one of functional groups represented by Chemical Formula 2A-2-1.

[Chemical Formula 2A-2-1]

In Chemical Formula 2A-2-1,
R$^b$, R$^{a1}$, R$^{a2}$, R$^{a3}$, R$^{a4}$, R$^{a5}$, and R$^{a6}$ are independently hydrogen or a C1 to C10 alkyl group, and b is an integer of 1 to 3.

Chemical Formula 2A-3 may be one of functional groups represented by Chemical Formula 2A-3-1.

[Chemical Formula 2A-3-1]

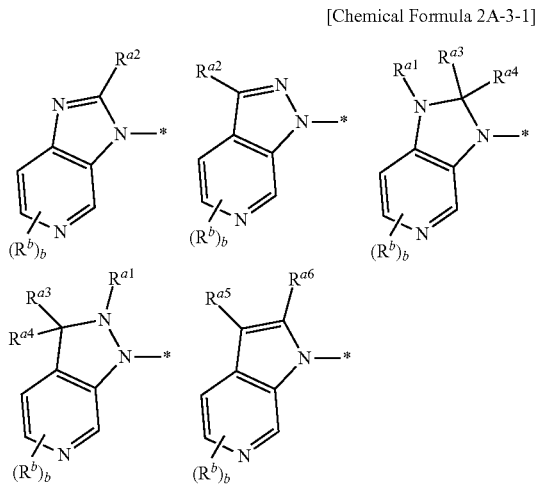

In Chemical Formula 2A-3-1,
$R^b$, $R^{a1}$, $R^{a2}$, $R^{a3}$, $R^{a4}$, $R^{a5}$, and $R^{a6}$ are independently hydrogen or a C1 to C10 alkyl group, and
b is an integer of 1 to 3.

Chemical Formula 2A-4 may be one of functional groups represented by Chemical Formula 2A-4-1.

[Chemical Formula 2A-4-1]

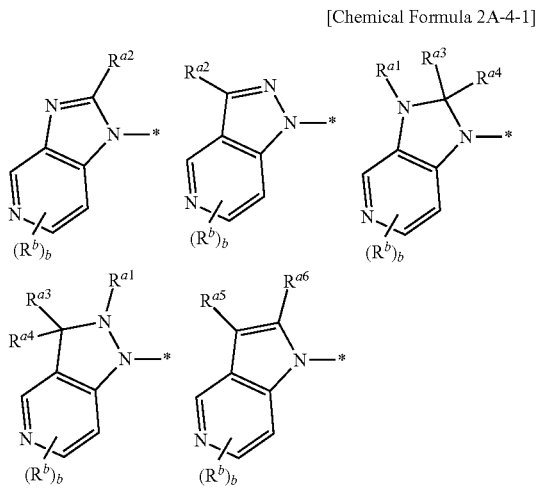

In Chemical Formula 2A-4-1,
$R^b$, $R^{a1}$, $R^{a2}$, $R^{a3}$, $R^{a4}$, $R^{a5}$, and $R^{a6}$ are independently hydrogen or a C1 to C10 alkyl group, and
b is an integer of 1 to 3.

Chemical Formula 2A-5 may be one of functional groups represented by Chemical Formula 2A-5-1.

[Chemical Formula 2A-5-1]

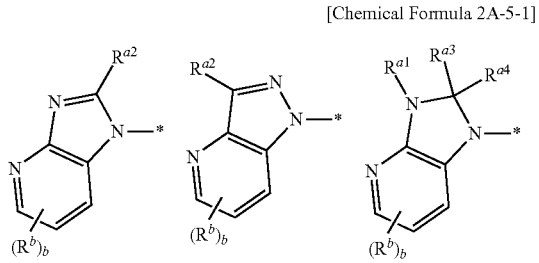
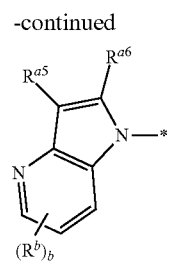

In Chemical Formula 2A-5-1,
$R^b$, $R^{a1}$, $R^{a2}$, $R^{a3}$, $R^{a4}$, $R^{a5}$, and $R^{a6}$ are independently hydrogen or a C1 to C10 alkyl group, and
b is an integer of 1 to 3.

Chemical Formula 2A-6 may be one of functional groups represented by Chemical Formula 2A-6-1.

[Chemical Formula 2A-6-1]

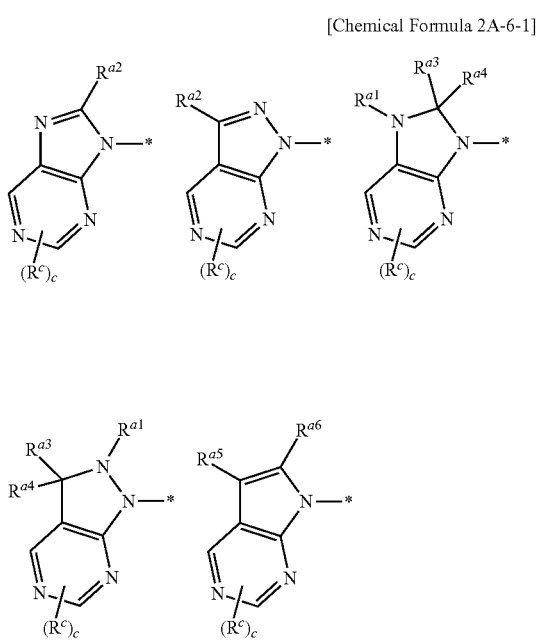

In Chemical Formula 2A-6-1,
$R^c$, $R^{a1}$, $R^{a2}$, $R^{a3}$, $R^{a4}$, $R^{a5}$, and $R^{a6}$ are independently hydrogen or a C1 to C10 alkyl group, and
c is an integer of 1 or 2.

Chemical Formula 2A-7 may be one of functional groups represented by Chemical Formula 2A-7-1.

[Chemical Formula 2A-7-1]

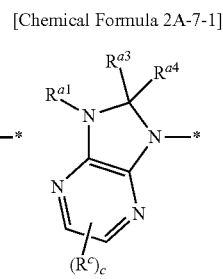

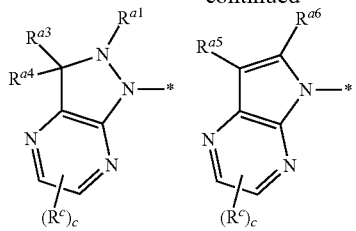

In Chemical Formula 2A-7-1,
$R^c$, $R^{a1}$, $R^{a2}$, $R^{a3}$, $R^{a4}$, $R^{a5}$, and $R^{a6}$ are independently hydrogen or a C1 to C10 alkyl group, and c is an integer of 1 or 2.

Chemical Formula 2A-8 may be one of functional groups represented by Chemical Formula 2A-8-1.

[Chemical Formula 2A-8-1]

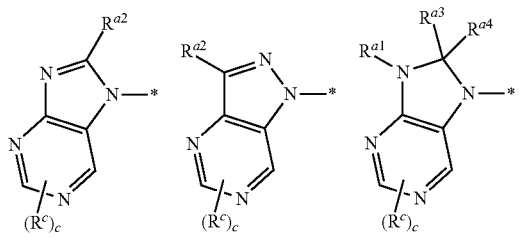

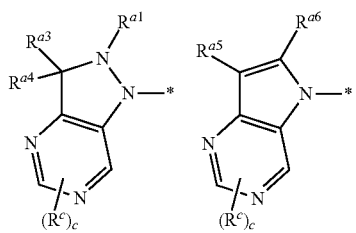

In Chemical Formula 2A-8-1,
$R^c$, $R^{a1}$, $R^{a2}$, $R^{a3}$, $R^{a4}$, $R^{a5}$, and $R^{a6}$ are independently hydrogen or a C1 to C10 alkyl group, and c is an integer of 1 or 2.

Chemical Formula 2A-9 may be one of functional groups represented by Chemical Formula 2A-9-1.

[Chemical Formula 2A-9-1]

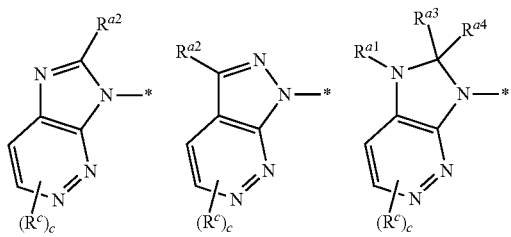

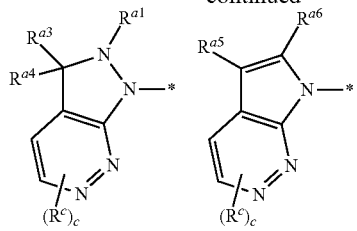

In Chemical Formula 2A-9-1,
$R^c$, $R^{a1}$, $R^{a2}$, $R^{a3}$, $R^{a4}$, $R^{a5}$, and $R^{a6}$ are independently hydrogen or a C1 to C10 alkyl group, and c is an integer of 1 or 2.

Chemical Formula 2A-10 may be one of functional groups represented by Chemical Formula 2A-10-1.

[Chemical Formula 2A-10-1]

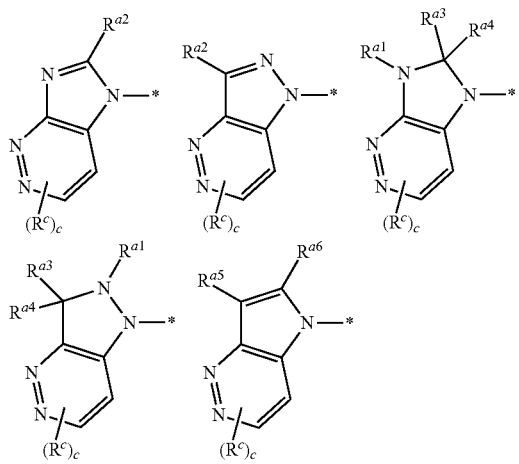

In Chemical Formula 2A-10-1,
$R^c$, $R^{a1}$, $R^{a2}$, $R^{a3}$, $R^{a4}$, $R^{a5}$, and $R^{a6}$ are independently hydrogen or a C1 to C10 alkyl group, and c is an integer of 1 or 2.

In the above, specific examples of Chemical Formulas 2A-1 to 2A-10 have been described in Chemical Formulas 2A-1-1 to 2A-10-1, but Chemical Formulas 2B-1 to 2B-10 may also be provided by the same manner.

In Chemical Formula 1, the cyclic group represented by $Ar^1$ includes at least one functional group of C=O, C=S, C=Se, and C=Te as an electron acceptor moiety.

$Ar^1$ may be a substituted or unsubstituted C6 to C30 hydrocarbon cyclic group having at least one functional group selected from C=O, C=S, C=Se, and C=Te, a substituted or unsubstituted C6 to C30 heterocyclic group having at least one functional group selected from C=O, C=S, C=Se, and C=Te, or a fused ring thereof.

In an embodiment, $Ar^1$ may be a substituted or unsubstituted 5-membered aromatic ring having at least one functional group selected from C=O, C=S, C=Se, and C=Te, a substituted or unsubstituted 6-membered aromatic rings having at least one functional group selected from C=O, C=S, C=Se, and C=Te, or a condensed ring of two or more.

In Chemical Formula 1, $Ar^1$ may be represented by Chemical Formula 3.

[Chemical Formula 3]

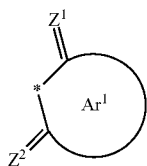

In Chemical Formula 3,
Ar$^1$ is a substituted or unsubstituted C6 to C30 aryl group or a substituted or unsubstituted C3 to C30 heteroaryl group,
Z$^1$ is O, S, Se, or Te, and
Z$^2$ is O, S, Se, Te, or CR$^a$R$^b$, wherein R$^a$ and R$^b$ are independently hydrogen, a substituted or unsubstituted C1 to C10 alkyl group, a cyano group or a cyano-containing group, provided that when Z$^2$ is CR$^a$R$^b$, at least one of R$^a$ and R$^b$ is a cyano group or a cyano-containing group.

In Chemical Formula 1, Ar$^1$ may be a cyclic group represented by one of Chemical Formula 4A to Chemical Formula 4F.

[Chemical Formula 4A]

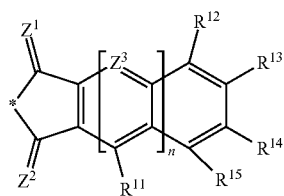

In Chemical Formula 4A,
Z$^1$ is O, S, Se, or Te,
Z$^2$ is O, S, Se, Te, or CR$^a$R$^b$, wherein R$^a$ and R$^b$ are independently hydrogen, a substituted or unsubstituted C1 to C10 alkyl group, a cyano group or a cyano-containing group, provided that when Z$^2$ is CR$^a$R$^b$, at least one of R$^a$ and R$^b$ is a cyano group or a cyano-containing group,
Z$^3$ is N or CR$^c$, wherein R$^c$ is hydrogen, deuterium, or a substituted or unsubstituted C1 to C10 alkyl group,
R$^{11}$, R$^{12}$, R$^{13}$, R$^{14}$, and R$^{15}$ are the same or different and are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof or R$^{12}$ and R$^{13}$ and R$^{14}$ and R$^{15}$ are independently present and are linked to each other to provide a fused aromatic ring,
n is 0 or 1, and
* is a linking point.

[Chemical Formula 4B]

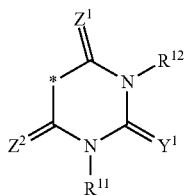

In Chemical Formula 4B,
Z$^1$ is O, S, Se, or Te,
Z$^2$ is O, S, Se, Te, or CR$^a$R$^b$, wherein R$^a$ and R$^b$ are independently hydrogen, a substituted or unsubstituted C1 to C10 alkyl group, a cyano group or a cyano-containing group, provided that when Z$^2$ is CR$^a$R$^b$, at least one of R$^a$ and R$^b$ is a cyano group or a cyano-containing group,
Y$^1$ is O, S, Se, Te, or C(R$^a$)(CN), wherein R$^a$ is hydrogen, a cyano group (—CN), or a C1 to C10 alkyl group,
R$^{11}$ and R$^{12}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and
* is a linking point.

[Chemical Formula 4C]

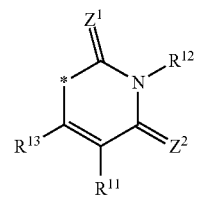

In Chemical Formula 4C,
Z$^1$ is O, S, Se, or Te,
Z$^2$ is O, S, Se, Te, or CR$^a$R$^b$, wherein R$^a$ and R$^b$ are independently hydrogen, a substituted or unsubstituted C1 to C10 alkyl group, a cyano group or a cyano-containing group, provided that when Z$^2$ is CR$^a$R$^b$, at least one of R$^a$ and R$^b$ is a cyano group or a cyano-containing group,
R$^{11}$, R$^{12}$, and R$^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and
* is a linking point.

[Chemical Formula 4D]

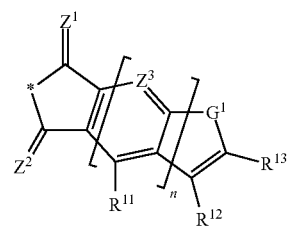

In Chemical Formula 4D,
Z$^1$ is O, S, Se, or Te,
Z$^2$ is O, S, Se, Te, or CR$^a$R$^b$, wherein R$^a$ and R$^b$ are independently hydrogen, a substituted or unsubstituted C1 to C10 alkyl group, a cyano group or a cyano-containing group, provided that when Z$^2$ is CR$^a$R$^b$, at least one of R$^a$ and R$^b$ is a cyano group or a cyano-containing group, $Z^3$ is N or $CR^c$, wherein $R^c$ is hydrogen or a substituted or unsubstituted C1 to C10 alkyl group, $G^1$ is —O—, —S—, —Se—, —Te—, —SiR$^x$R$^y$—, or —GeR$^z$R$^w$—, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group, $R^{11}$, $R^{12}$, and $R^{13}$, are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, $R^{12}$ and $R^{13}$ may independently be present or may be linked to each other to provide a fused aromatic ring, n is 0 or 1, and

* is a linking point.

[Chemical Formula 4E]

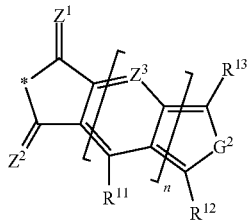

In Chemical Formula 4E, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group or a cyano-containing group, provided that when $Z^2$ is $CR^aR^b$, at least one of $R^a$ and $R^b$ is a cyano group or a cyano-containing group, $Z^3$ is N or $CR^c$, wherein $R^c$ is hydrogen or a substituted or unsubstituted C1 to C10 alkyl group, $G^2$ is —O—, —S—, —Se—, —Te—, —SiR$^x$R$^y$—, or —GeR$^z$R$^w$—, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group, $R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, n is 0 or 1, and

* is a linking point.

[Chemical Formula 4F]

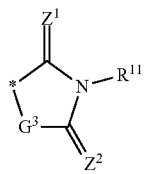

In Chemical Formula 4F, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group or a cyano-containing group, provided that when $Z^2$ is $CR^aR^b$, at least one of $R^a$ and $R^b$ is a cyano group or a cyano-containing group, $R^{11}$ is hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and $G^3$ is —O—, —S—, —Se—, —Te—, —SiR$^x$R$^y$—, or —GeR$^z$R$^w$—, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group.

The cyclic group represented by Chemical Formula 4A may be a cyclic group represented by Chemical Formula 4A-1 or Chemical Formula 4A-2.

[Chemical Formula 4A-1]

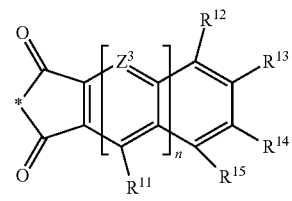

[Chemical Formula 4A-2]

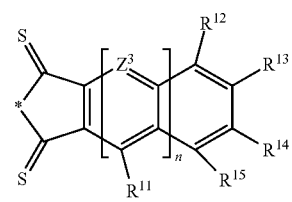

In Chemical Formulas 4A-1 and 4A-2, $Z^3$, $R^{11}$, n, $R^{11}$, $R^{12}$, $R^{13}$, $R^{14}$, and $R^{15}$ are the same as in Chemical Formula 4A.

The cyclic group represented by Chemical Formula 4A may be a cyclic group represented by Chemical Formula 4A-3 when $R^{12}$ and $R^{13}$ and/or $R^{14}$ and $R^{15}$ are independently linked to form a fused aromatic ring.

[Chemical Formula 4A-3]

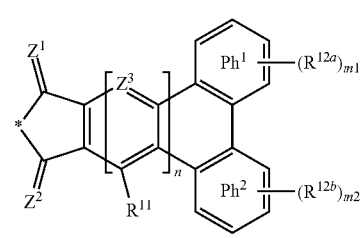

In Chemical Formula 4A-3, $Z^1$, $Z^2$, $Z^3$, $R^{14}$, and n are the same as in Chemical Formula 2A, $R^{12a}$ and $R^{12b}$ are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, m1 and m2 are independently an integer of 0 to 4, and Ph1 and Ph2 refer to fused phenylene rings and one of Ph1 and Ph2 may be optionally omitted.

The cyclic group represented by Chemical Formula 4B may be, for example, a cyclic group represented by Chemical Formula 4B-1, 4B-2, or 4B-3.

[Chemical Formula 4B-1]

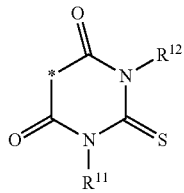

[Chemical Formula 4B-2]

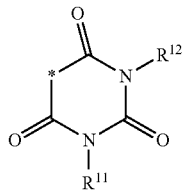

[Chemical Formula 4B-3]

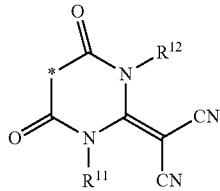

In Chemical Formulas 4B-1, 4B-2, and 4B-3, $R^{11}$ and $R^{12}$ are the same as in Chemical Formula 4B.

The cyclic group represented by Chemical Formula 4C may be, for example, a cyclic group represented by Chemical Formula 4C-1 or 4C-3.

[Chemical Formula 4C-1]

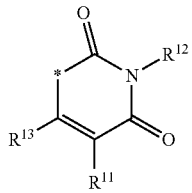

[Chemical Formula 4C-2]

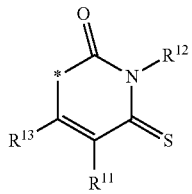

In Chemical Formulas 4C-1 and 4C-2, $R^{11}$ to $R^{13}$ are the same as in Chemical Formula 4C.

In Chemical Formula 1, X of the linker and $Z^1$ and $Z^2$ (O, S, Se, or Te) present in the electron acceptor moiety may increase an intramolecular interaction to improve absorption intensity at desired and/or alternatively predetermined wavelengths.

In an embodiment, $R^1$ and $R^2$ may be linked to each other to form a ring, and in this case, the X-containing linker may be represented by Chemical Formula 5A or 5B.

[Chemical Formula 5A]

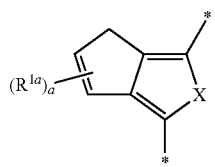

[Chemical Formula 5B]

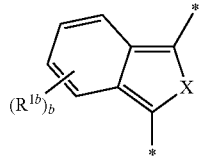

In Chemical Formulas 5A and 5B, $R^{1a}$ and $R^{1b}$ are hydrogen, a C1 to C10 alkyl group, a C6 to C10 aryl group, a C2 to C10 heteroaryl group, or a halogen, and a and b are independently an integer of 1 to 4.

Specific examples of the compound of Chemical Formula 1 include compounds of Chemical Formula 6A, Chemical Formula 6B, Chemical Formula 6C, Chemical Formula 6D, Chemical Formula 6E, and Chemical Formula 6F, but are not limited thereto.

[Chemical Formula 6A]

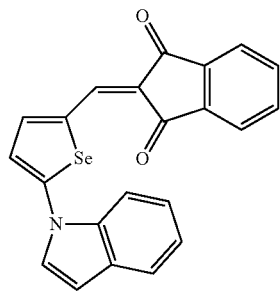

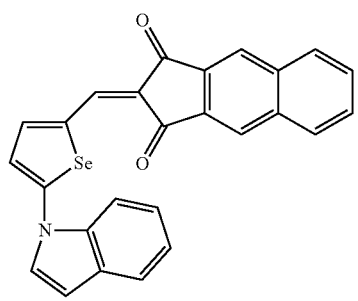

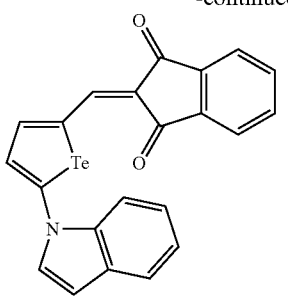
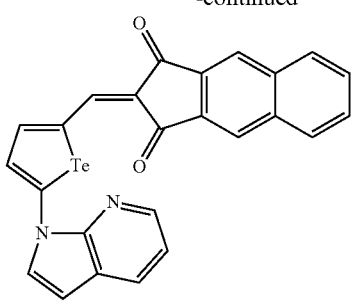
10-3
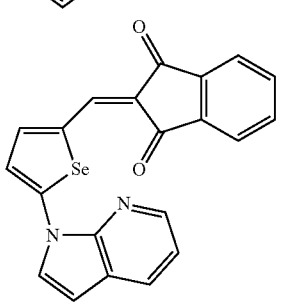
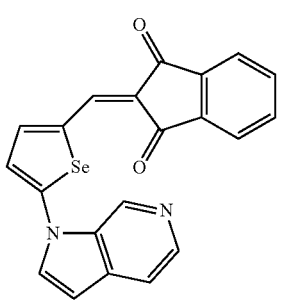
10-2
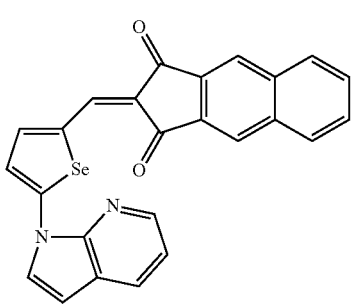
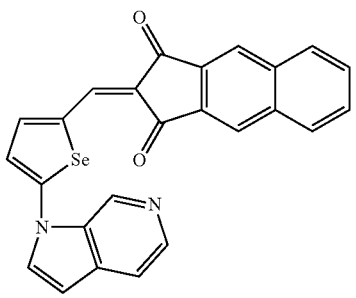
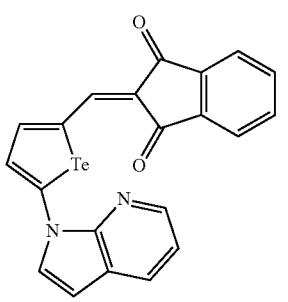
10-2
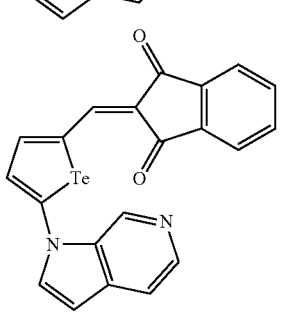

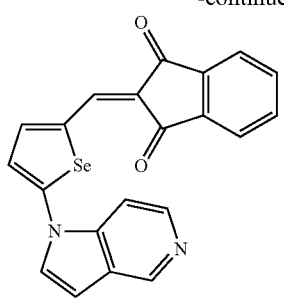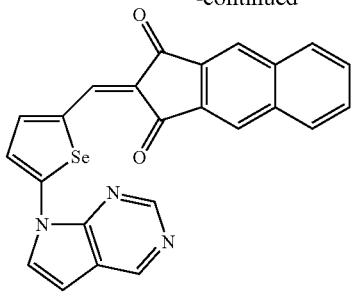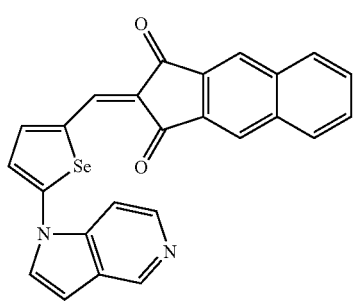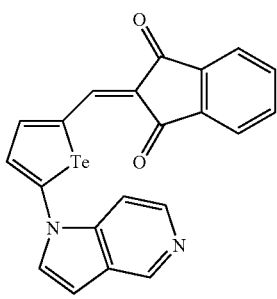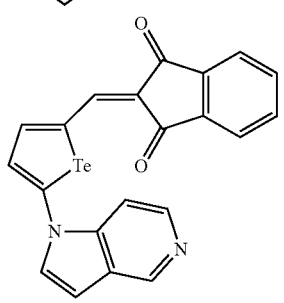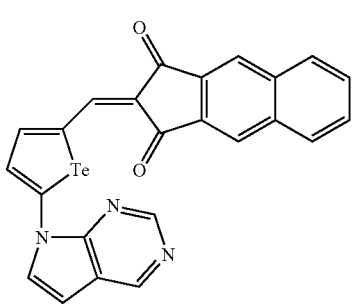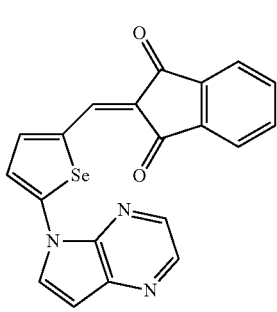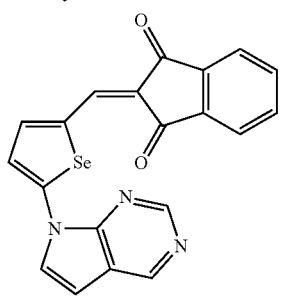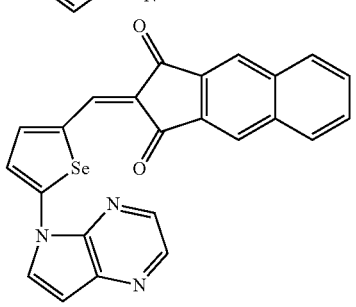

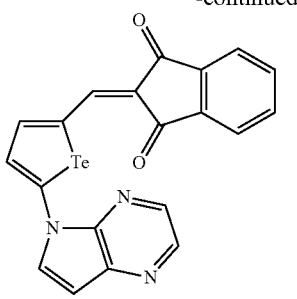

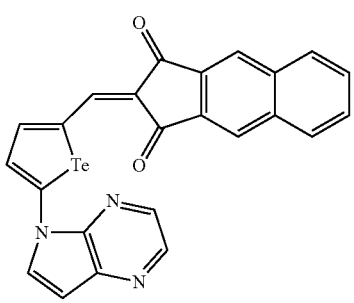

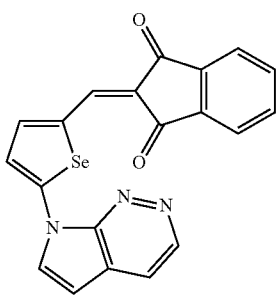

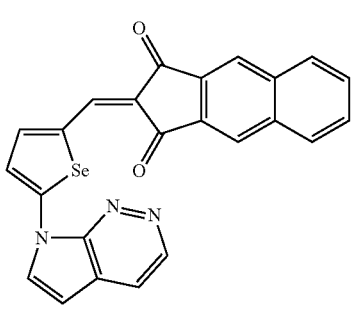

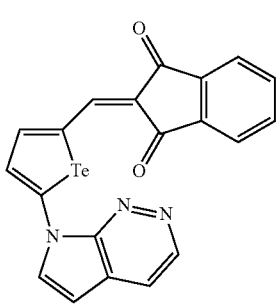

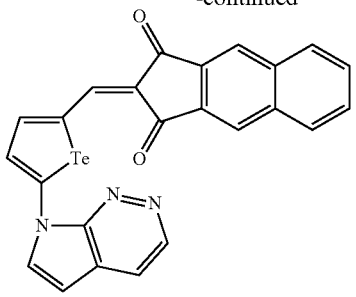

In Chemical Formula 6A,
hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

[Chemical Formula 6B]

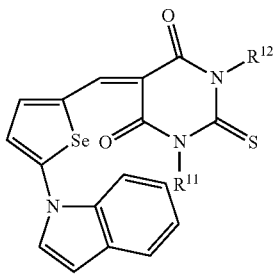

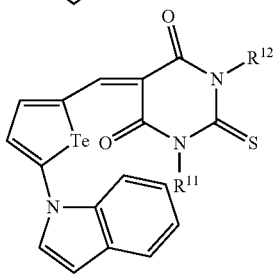

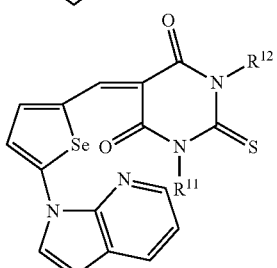

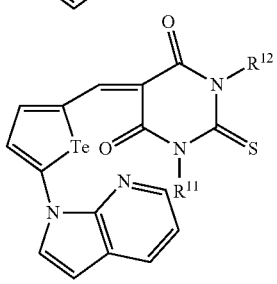

-continued
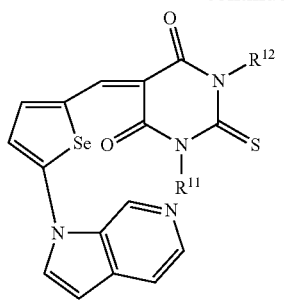
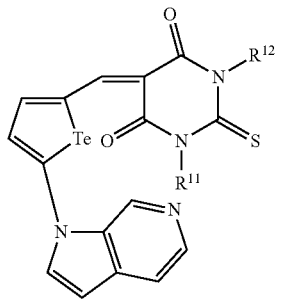
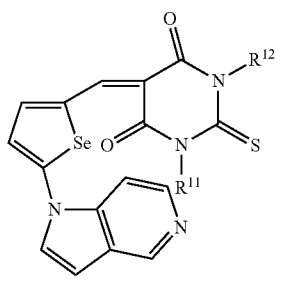
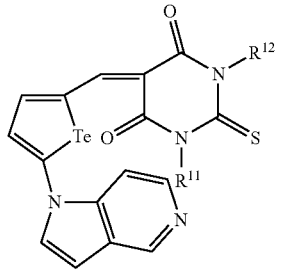
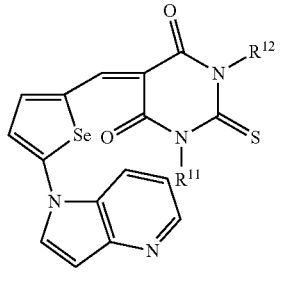
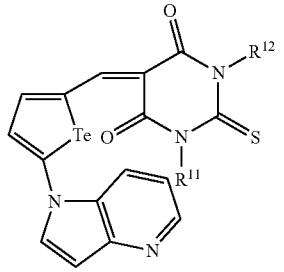
-continued
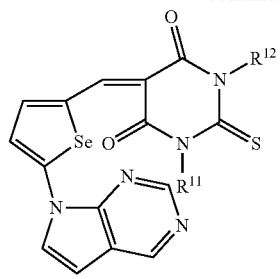
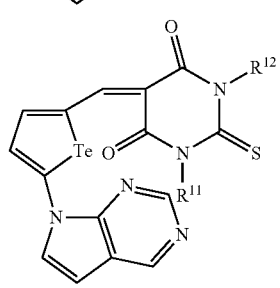
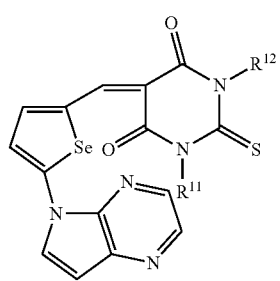
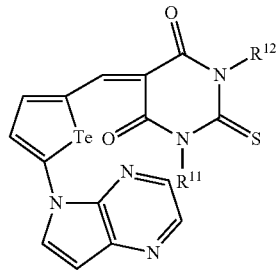
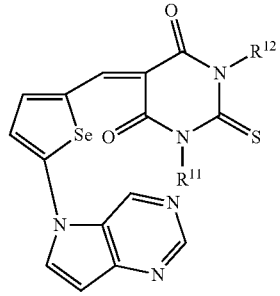
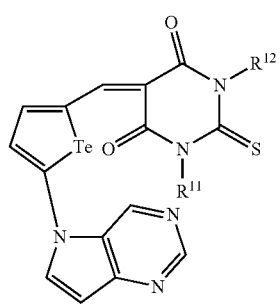

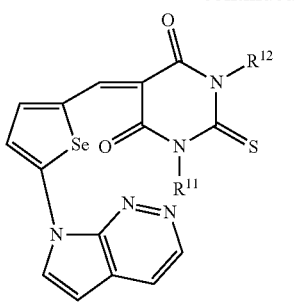

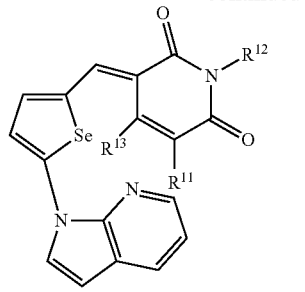

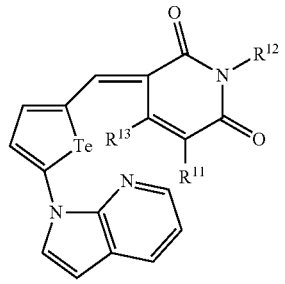

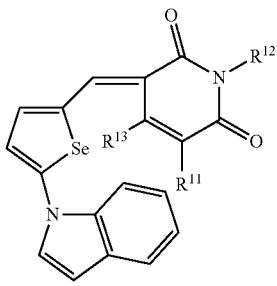

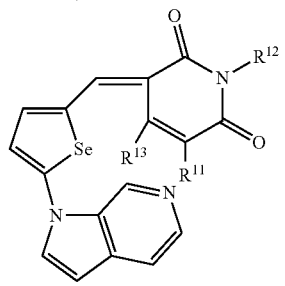

In Chemical Formula 6B,

R[11] and R[12] are the same as in Chemical Formula 4B, hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

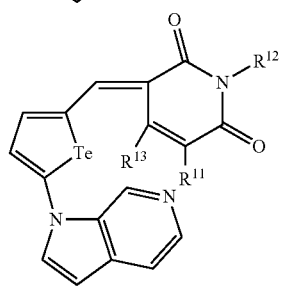

[Chemical Formula 6C]

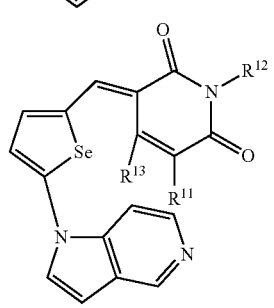

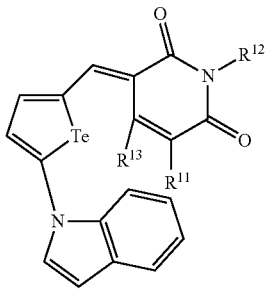

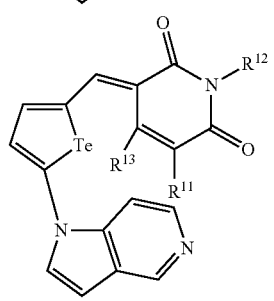

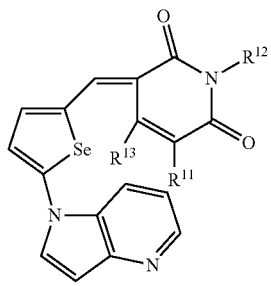
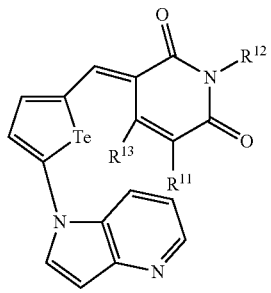
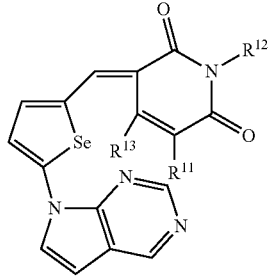
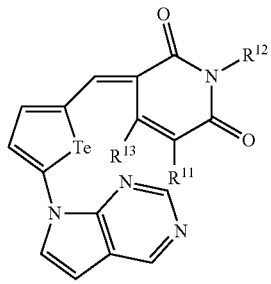
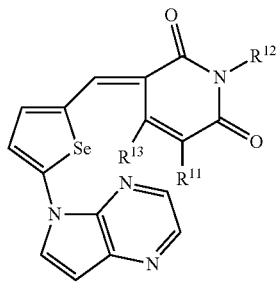
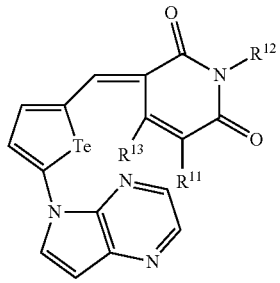

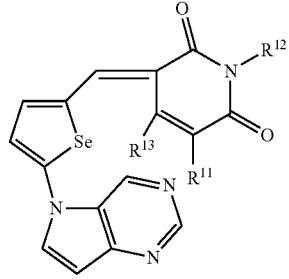
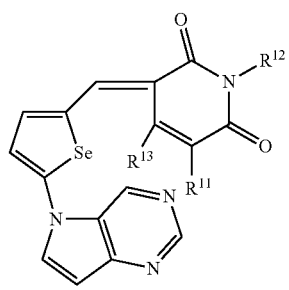
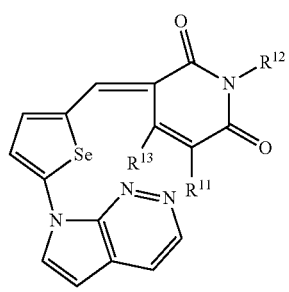
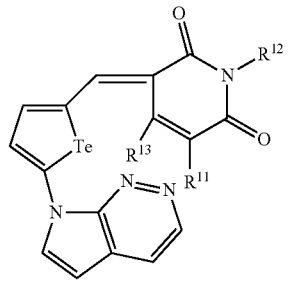

In Chemical Formula 6C, $R^{11}$ to $R^{13}$ are the same as in Chemical Formula 4C, hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

[Chemical Formula 6D]
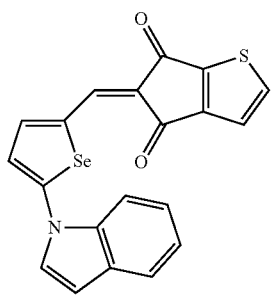
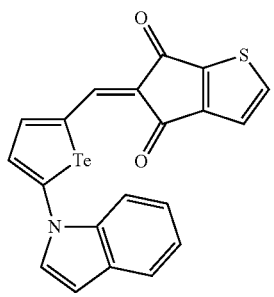
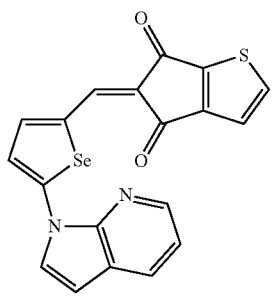
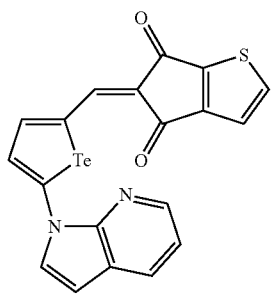
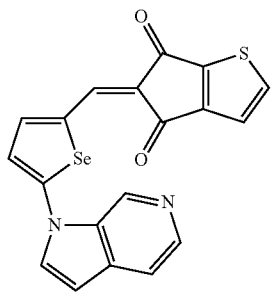
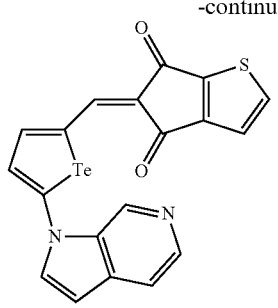
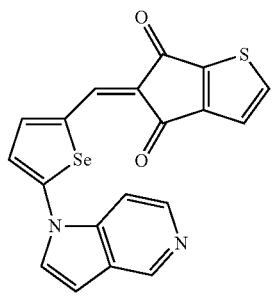
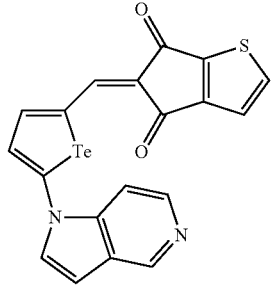
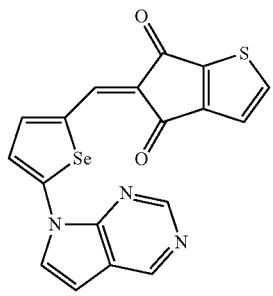
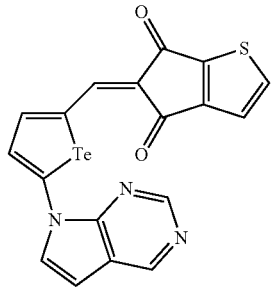

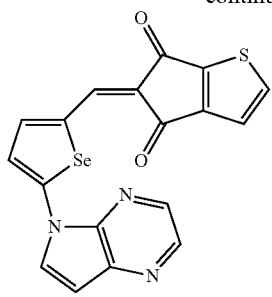
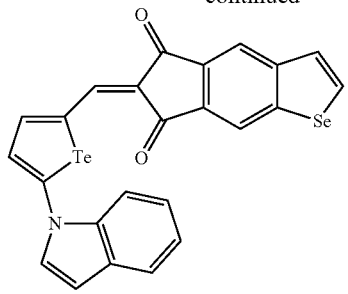
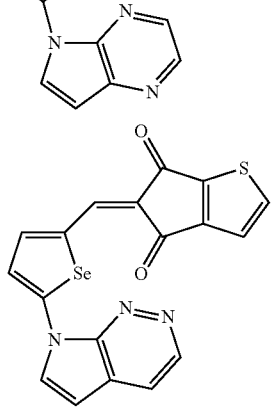
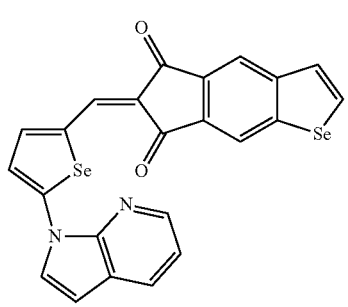
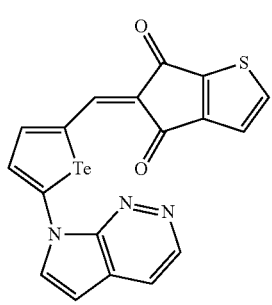
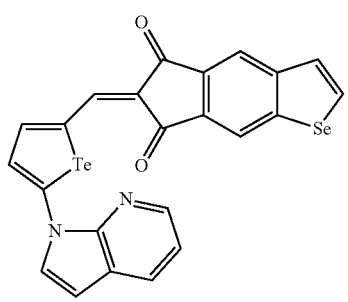
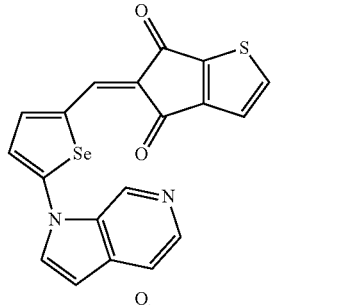
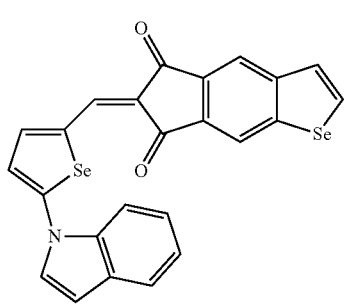
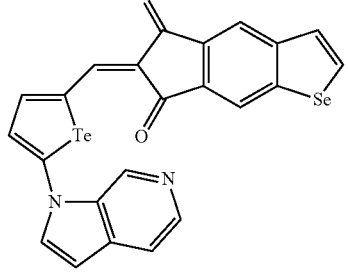

-continued

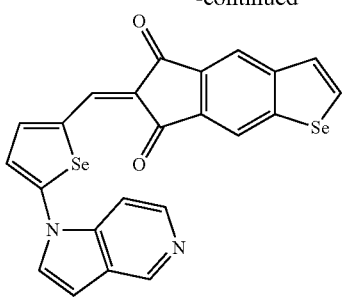

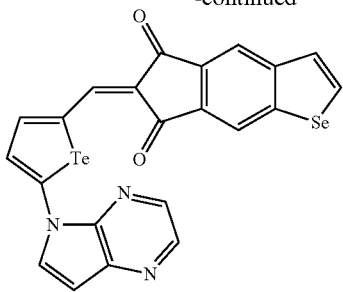

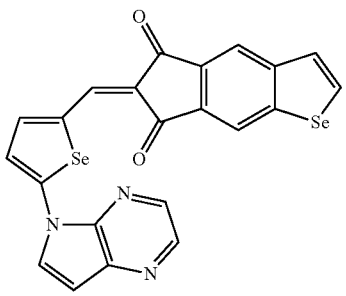

In Chemical Formula 6D, hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—ON), a cyano-containing group, and a combination thereof.

[Chemical Formula 6E]

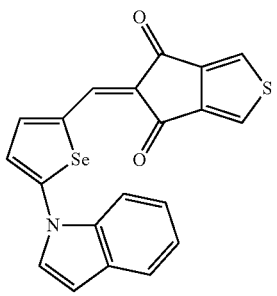

49
-continued
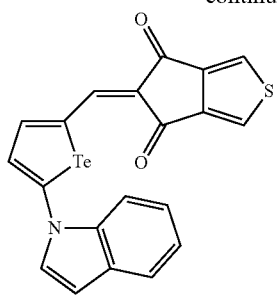
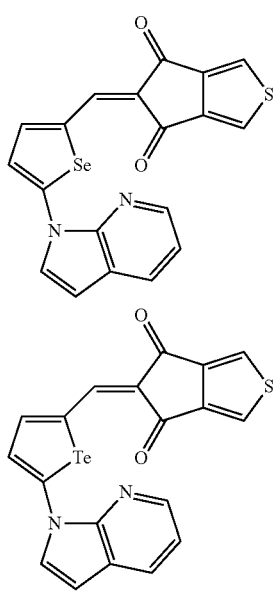
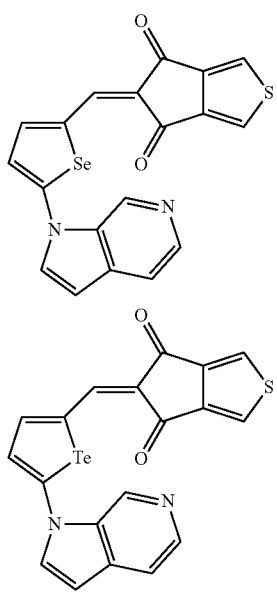
50
-continued
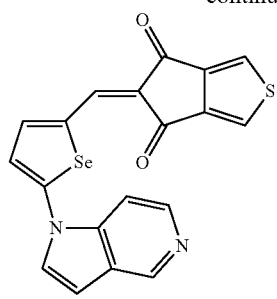
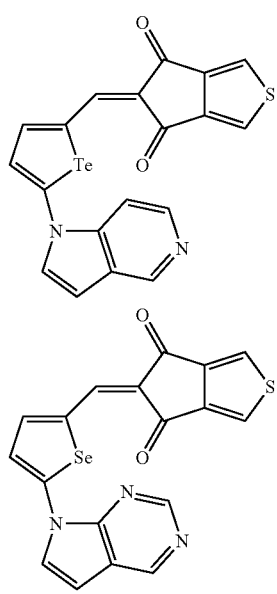
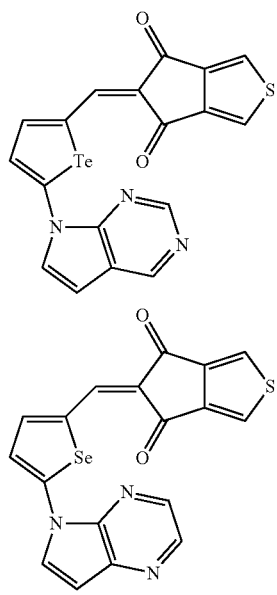

51
-continued
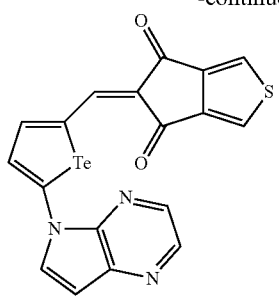
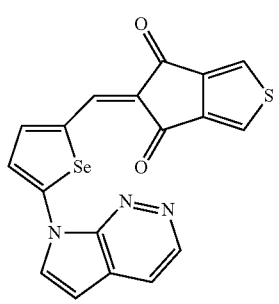
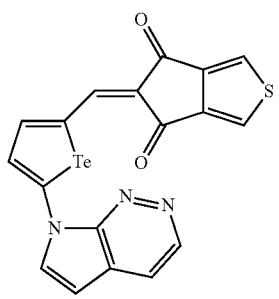
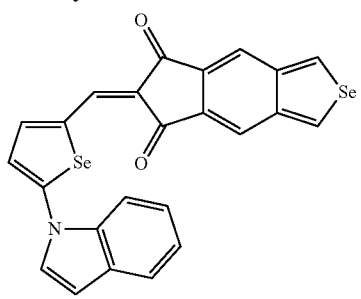
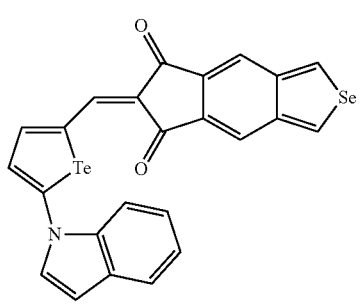
52
-continued
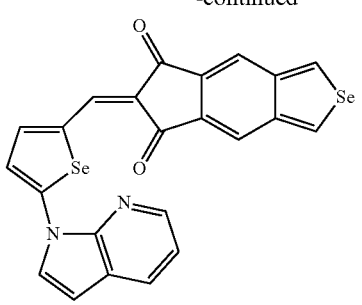
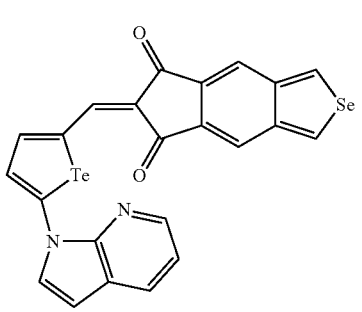
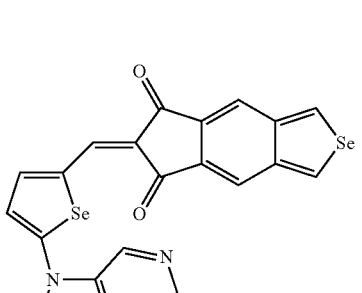
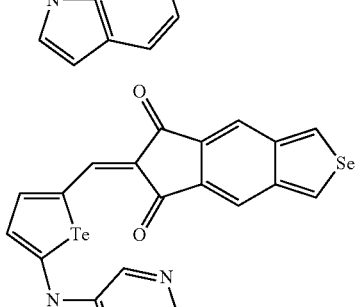
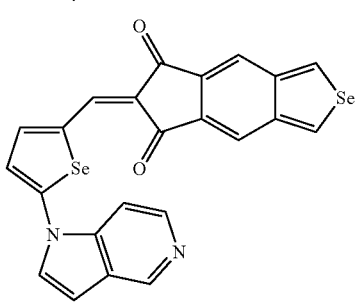

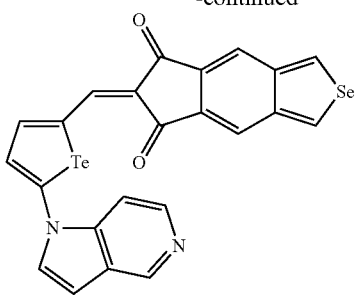

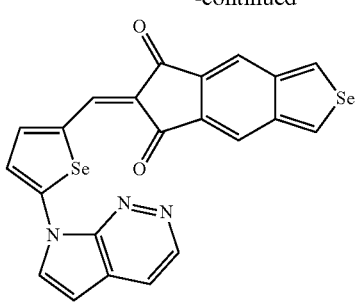

In Chemical Formula 6E, hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

[Chemical Formula 6F]

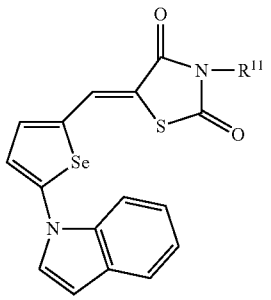

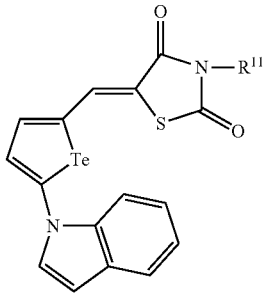

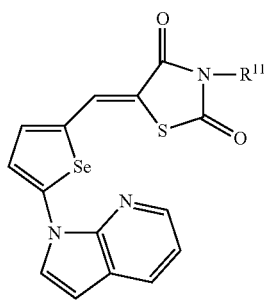
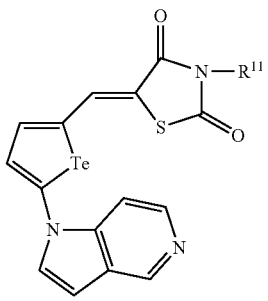
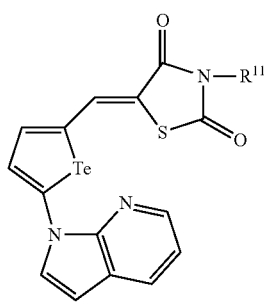
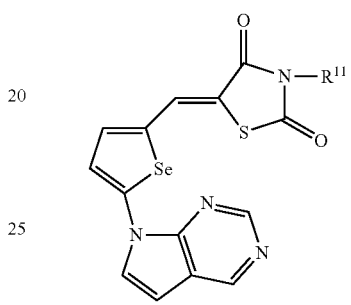
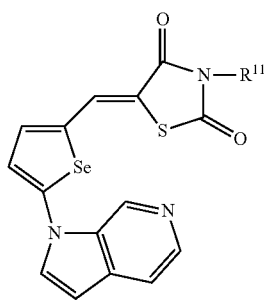
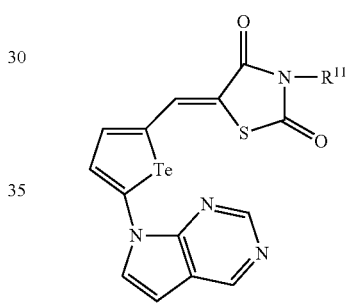
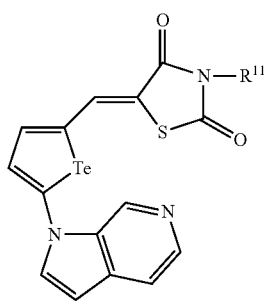
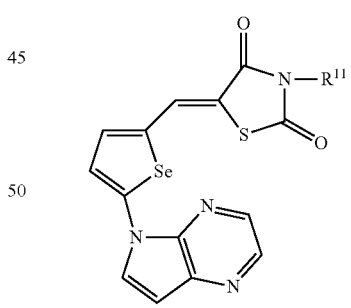
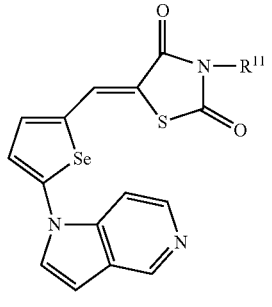
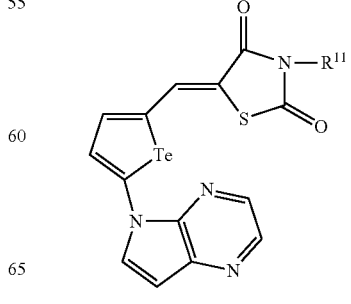

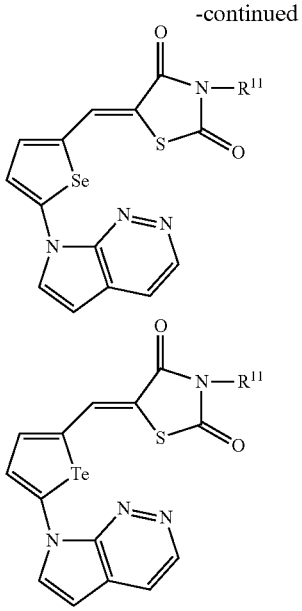

In Chemical Formula 6F,

R[11] is the same as in Chemical Formula 4F, and hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

The compound is a compound configured to selectively absorb light in a green wavelength region, and may have a maximum absorption wavelength (λmax) in a wavelength region of greater than or equal to about 500 nm, for example greater than or equal to about 520 nm, or greater than or equal to about 530 nm and less than or equal to about 600 nm, for example less than or equal to about 590 nm, less than or equal to about 580 nm, less than or equal to about 570 nm, less than or equal to about 560 nm, less than or equal to about 555 nm, or less than or equal to about 550 nm, in a thin film state.

The compound may exhibit a light absorption curve having a full width at half maximum (FWHM) of about 50 nm to about 120 nm, for example about 50 nm to about 110 nm or about 50 nm to about 100 nm, in a thin film state. Herein, the FWHM is a width of a wavelength corresponding to half of a maximum absorption point. As used herein, when specific definition is not otherwise provided, it may be defined by absorbance measured by UV-Vis spectroscopy. When the full width at half maximum (FWHM) is within the range, selectivity in a green wavelength region may be increased. The thin film may be a thin film deposited under a vacuum condition.

The compound may be formed into a thin film by vapor deposition. The deposition method may provide a uniform thin film and have small inclusion possibility of impurities into the thin film, but when the compound has a lower melting point than a temperature for the deposition, a product decomposed from the compound may be deposited and thus performance of a device may be deteriorated. Accordingly, the compound desirably has a higher melting point than the deposition temperature. In this respect, the compound has a melting point higher than the deposition temperature. Because a difference between the melting point and the deposition temperature may be for example greater than or equal to about 10° C., greater than or equal to about 20° C., the compound may be desirably used in the deposition process.

In more detail, the donor-acceptor type material represented by Chemical Formula 1 may be thermally decomposed at the melting point ($T_m$) of the material because the melting point ($T_m$) is similar to the decomposition temperature ($T_d$). If the temperature (sublimation temperature, deposition temperature, $T_s$) at which a film is formed by vacuum deposition is higher than $T_m$, decomposition occurs more preferentially than sublimation (deposition), and thus a normal device cannot be manufactured. Because it is impossible to produce a stable image sensor with such materials, $T_m$ is required to be higher than $T_s$. In an embodiment, ($T_m-T_s$) may be in the range of ($T_m-T_s$)≥10° C. and for example ($T_m-T_s$)≥20° C.

In addition, a micro lens array (MLA) needs to be formed to concentrate light after manufacturing an organic photoelectric device during manufacture of an image sensor. Formation of his micro lens array requires a relatively high temperature (greater than or equal to about 160° C., for example greater than or equal to about 170° C., greater than or equal to about 180° C., or greater than or equal to about 190° C.). The performance of the photoelectric devices (e.g., organic photoelectric devices) is required not to be deteriorated in these heat-treatment processes. The performance deterioration of the organic photoelectric device during the heat treatment of MLA may be caused not by chemical decomposition of an organic material but its morphology change. The morphology change is in general caused, when a material starts a thermal agitation due to a heat treatment, but even a material having a firm molecule structure may not have the thermal agitation and be limited and/or prevented from the deterioration by the heat treatment. The compound may be suppressed from the thermal vibration of molecules due to a conjugation structure (G-containing linkage structure of Chemical Formula 1) in the donor moiety and thus may be stably maintained during the MLA heat treatment and secure process stability.

The compound may be a p-type semiconductor compound.

Since the compound works as a p-type semiconductor, the compound may be appropriately used, as long as it has a higher LUMO level than an n-type semiconductor. For example, when the compound is mixed with an n-type material such as fullerene, the compound desirably has a higher LUMO level than 4.2 eV than the fullerene having a LUMO level of 4.2 eV. As for the appropriate HOMO-LUMO level of the compound, when the compound has a HOMO level ranging from about 5.2 eV to about 5.8 eV, and an energy bandgap ranging from about 1.4 eV to about 2.6 eV, the LUMO level of the compound is in a range of about 3.8 eV to about 3.2 eV. The compound having a HOMO level, an LUMO level, and an energy bandgap within the ranges may be used as a p-type semiconductor compound effectively absorbing light in a green wavelength region, and thus has high external quantum efficiency (EQE) and resultantly improves photoelectric conversion efficiency.

In example embodiments, in view of a thin film formation, a stably depositable compound is desirable and thus the compound has a molecular weight of about 300 g/mol to about 1500 g/mol. However, even though the compound has a molecular weight out of the range, a depositable compound may be used without limitation. In addition, when the compound is formed to form a thin film using a coating process, a compound that is dissolved in a solvent and coated may be used without limitation.

Hereinafter, a photoelectric device including the compound according to an embodiment is described with reference to drawings.

FIG. 1 is a cross-sectional view showing a photoelectric device according to an embodiment.

Referring to FIG. 1, a photoelectric device 100 according to an example embodiment includes a first electrode 10 and a second electrode 20, and an active layer 30 between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor such as indium tin oxide (ITO) or indium zinc oxide (IZO), or a metal thin layer of a thin single layer or multilayer. The metal thin layer may include a metal alloy in some embodiments When one of the first electrode 10 and the second electrode 20 is a non-light-transmitting electrode, it may be made of, for example, an opaque conductor such as aluminum (Al).

The active layer 30 includes a p-type semiconductor and an n-type semiconductor to form a pn junction and absorbs external light to generate excitons and then separates the generated excitons into holes and electrons.

The active layer 30 includes the compound represented by Chemical Formula 1. The compound may act as a p-type semiconductor compound in the active layer 30.

The compound is a compound configured to selectively absorb light in a green wavelength region, and the active layer 30 including the compound may have a maximum absorption wavelength (λmax) in a wavelength region of greater than or equal to about 500 nm, for example greater than or equal to about 520 nm, or greater than or equal to about 530 nm and less than or equal to about 600 nm, for example less than or equal to about 590 nm, less than or equal to about 580 nm, less than or equal to about 570 nm, less than or equal to about 560 nm, less than or equal to about 555 nm, or less than or equal to about 550 nm.

The active layer 30 may exhibit a light absorption curve having a relatively narrow full width at half maximum (FWHM) of about 50 nm to about 120 nm, for example about 50 nm to about 110 nm or about 50 nm to about 100 nm. Accordingly, the active layer 30 has high selectivity for light in a green wavelength region.

The active layer may have an absorption coefficient of greater than or equal to about $6.0 \times 10^4$ cm$^{-1}$, for example greater than or equal to about $6.5 \times 10^4$ cm$^{-1}$, or greater than or equal to about $7.0 \times 10^4$ cm$^{-1}$ when including the compound Chemical Formula 1 and C60 in a volume ratio of about 0.9:1 to about 1.1:1, for example about 1:1.

The active layer 30 may further include an n-type semiconductor compound for forming pn junction.

The n-type semiconductor compound may be sub-phthalocyanine or a sub-phthalocyanine derivative, fullerene or a fullerene derivative, thiophene or a thiophene derivative, or a combination thereof.

The fullerene may include C60, C70, C76, C78, C80, C82, C84, C90, C96, C240, C540, a mixture thereof, a fullerene nanotube, and the like. The fullerene derivative may refer to compounds of these fullerenes having a substituent thereof. The fullerene derivative may include a substituent such as an alkyl group (e.g., C1 to C30 alkyl group), an aryl group (e.g., C6 to C30 aryl group), a heterocyclic group (e.g., C3 to C30 cycloalkyl group), and the like. Examples of the aryl groups and heterocyclic groups may be are a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, an xanthene ring, a phenoxazine ring, a phenoxathin ring, a phenothiazine ring, or a phenazine ring.

The sub-phthalocyanine or the sub-phthalocyanine derivative may be represented by Chemical Formula 7.

[Chemical Formula 7]

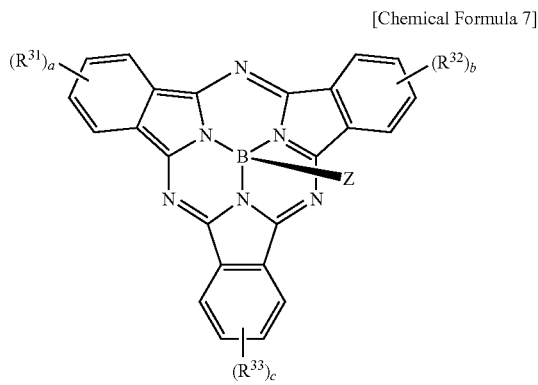

In Chemical Formula 7, $R^{31}$ to $R^{33}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a halogen-containing group, or a combination thereof, a, b, and c are integers ranging from 1 to 3, and Z is a monovalent substituent.

For example, Z may be a halogen or a halogen-containing group, for example F, Cl, an F-containing group, or a Cl-containing group.

The halogen refers to F, Cl, Br, or I and the halogen-containing group refers to alkyl group (C1 to C30 alkyl group) where at least one of hydrogen is replaced by F, Cl, Br, or I.

The thiophene derivative may be for example represented by Chemical Formula 8 or Chemical Formula 9, but is not limited thereto.

[Chemical Formula 8]

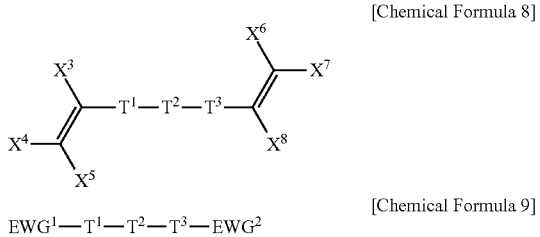

[Chemical Formula 9]

EWG$^1$—T$^1$—T$^2$—T$^3$—EWG$^2$

In Chemical Formulas 8 and 9,

T$^1$, T$^2$, and T$^3$ are aromatic rings including substituted or unsubstituted thiophene moieties, T$^1$, T$^2$, and T$^3$ are independently present or are fused to each other, X$^3$ to X$^8$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a cyano group, or a combination thereof, and EWG$^1$ and EWG$^2$ are independently electron withdrawing groups.

For example, in Chemical Formula 8, at least one of X$^3$ to X$^8$ may be an electron withdrawing group, for example a cyano-containing group.

The active layer 30 may further include a second p-type semiconductor compound configured to selectively absorb green light. The second p-type semiconductor compound may be a compound represented by Chemical Formula 10.

[Chemical Formula 10]

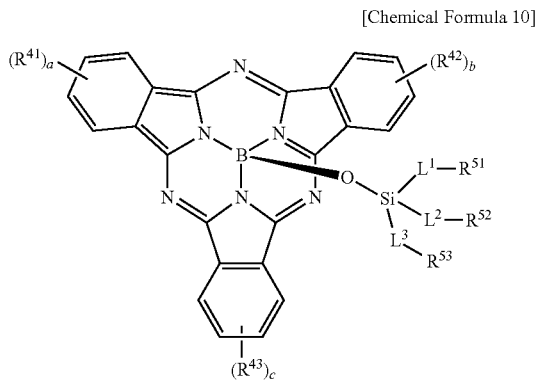

In Chemical Formula 10,

R$^{41}$ to R$^{43}$ are independently hydrogen, a substituted or unsubstituted C1 to C30 aliphatic hydrocarbon group, a substituted or unsubstituted C6 to C30 aromatic hydrocarbon group, a substituted or unsubstituted C1 to C30 aliphatic heterocyclic group, a substituted or unsubstituted C2 to C30 aromatic heterocyclic group, a substituted or unsubstituted C1 to C30 alkoxy group, a substituted or unsubstituted C6 to C30 aryloxy group, a thiol group, a substituted or unsubstituted C1 to C30 alkylthio group, a substituted or unsubstituted C6 to C30 arylthio group, a cyano group, a cyano-containing group, a halogen, a halogen-containing group, a substituted or unsubstituted sulfonyl group (e.g., a substituted or unsubstituted C0 to C30 aminosulfonyl group, a substituted or unsubstituted C1 to C30 alkylsulfonyl group or a substituted or unsubstituted C6 to C30 arylsulfonyl group), or a combination thereof, or two adjacent groups of R$^{41}$ to R$^{43}$ are linked to each other to provide a fused ring, L$^1$ to L$^3$ are independently a single bond, a substituted or unsubstituted C1 to C30 alkylene group, a substituted or unsubstituted C6 to C30 arylene group, divalent substituted or unsubstituted C3 to C30 heterocyclic group, or a combination thereof, R$^{51}$ to R$^{53}$ are independently a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted C1 to C30 alkoxy group, a substituted or unsubstituted amine group (e.g., a substituted or unsubstituted C1 to C30 alkylamine group or a substituted or unsubstituted C6 to C30 arylamine group), a substituted or unsubstituted silyl group, or a combination thereof, and a to c are independently an integer ranging from 0 to 4.

The second p-type semiconductor compound configured to selectively absorb green light may be included in an amount of about 500 to about 1500 parts by weight based on 100 parts by weight of the compound represented by Chemical Formula 1.

The active layer 30 may be a single layer or a multilayer. The active layer 30 may be, for example, an intrinsic layer (1 layer), a p-type layer/1 layer, an 1 layer/n-type layer, a p-type layer/1 layer/n-type layer, a p-type layer/n-type layer, and the like.

The intrinsic layer (1 layer) may include the compound of Chemical Formula 1 and the n-type semiconductor compound in a ratio of about 1:100 to about 100:1. The compound of Chemical Formula 1 and the n-type semiconductor compound may be included in a ratio ranging from about 1:50 to about 50:1 within the range, specifically, about 1:10 to about 10:1, and more specifically, about 1:1. When the compound of Chemical Formula 1 and the n-type semiconductor compound have a composition ratio within the range, an exciton may be effectively produced, and a pn junction may be effectively formed.

The p-type layer may include the semiconductor compound of Chemical Formula 1, and the n-type layer may include the n-type semiconductor compound.

The active layer 30 may have a thickness of about 1 nm to about 500 nm and specifically, about 5 nm to about 300 nm. When the active layer 30 has a thickness within the range, the active layer may effectively absorb light, effectively separate holes from electrons, and deliver them, thereby effectively improving photoelectric conversion efficiency. A desirable thickness of the active layer 30 may be, for example, determined by an absorption coefficient of the active layer 30, and may be, for example, a thickness being capable of absorbing light of at least about 70% or more, for example about 80% or more, and for another example about 90%.

In the photoelectric device 100, when light enters from the first electrode 10 and/or second electrode 20, and when the active layer 30 absorbs light in a desired and/or alternatively predetermined wavelength region, excitons may be produced from the inside. The excitons are separated into holes and electrons in the active layer 30, and the separated holes are transported to an anode that is one of the first electrode 10 and the second electrode 20 and the separated electrons are transported to the cathode that is the other of and the first electrode 10 and the second electrode 20 so as to flow a current in the photoelectric device.

Hereinafter, a photoelectric device according to another embodiment is described with reference to FIG. 2.

Figure 2:
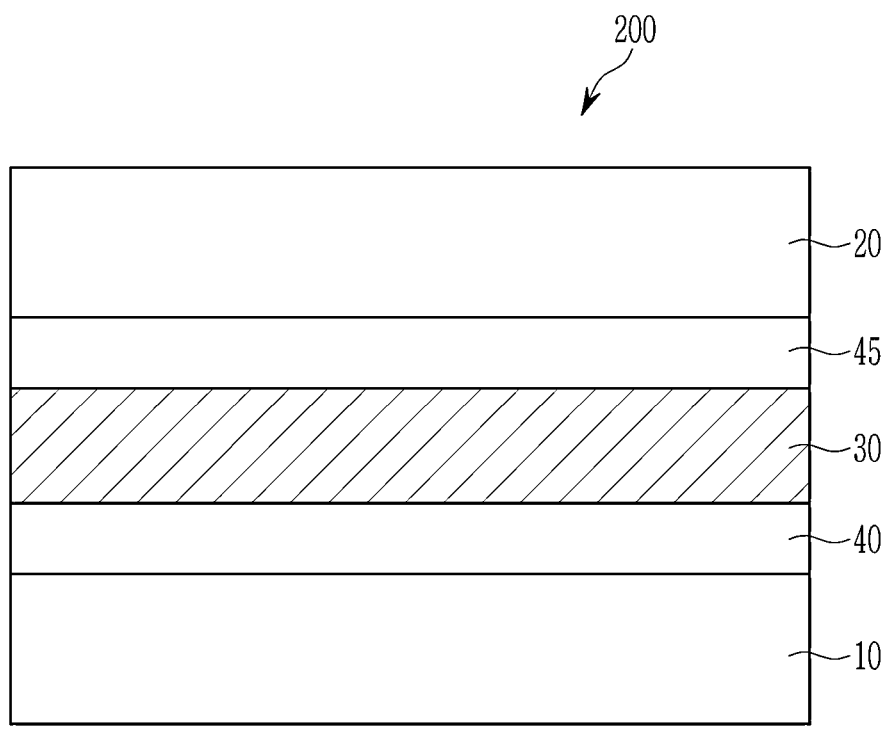
FIG. 2 is a cross-sectional view showing a photoelectric device according to another embodiment.

FIG. 2 is a cross-sectional view showing a photoelectric device according to another example embodiment.

Referring to FIG. 2, a photoelectric device 200 according to the present embodiment includes a first electrode 10 and a second electrode 20 facing each other, and an active layer 30 between the first electrode 10 and the second electrode 20, like the above embodiment.

However, the photoelectric device 200 according to the present embodiment further includes charge auxiliary layers 40 and 45 between the first electrode 10 and the active layer 30, and the second electrode 20 and the active layer 30, unlike the above embodiment. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for limiting and/or preventing electron transport, an electron injection layer (EIL) for facilitating electron injection, an electron transport layer (ETL) for facilitating electron transport, and a hole blocking layer (HBL) for limiting and/or preventing hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, and the like.

The hole transport layer (HTL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 45 may be omitted.

Referring to FIGS. 1 and 2, in some embodiments, the photoelectric devices 100 and 200 may be manufactured by forming the first electrode 10 on a substrate (not shown), such as a glass substrate or a semiconductor substrate (e.g., silicon substrate). The first electrode 10 may be formed on the substrate using a sputtering process. For example, the first electrode 10 may be formed by sputtering a transparent conductor such as indium tin oxide (ITO) or indium zinc oxide (IZO), or a metal thin layer of a thin single layer or multilayer, on the substrate.

After forming the first electrode 10 on the substrate, the active layer 30 may be formed on the first electrode 10 by depositing a p-type semiconductor over the first electrode 10. An n-type semiconductor may be deposited over the first electrode 10. The p-type semiconductor and the n-type semiconductor may be codeposited or separately deposited. The p-type semiconductor may include at least one compound represented by Chemical Formula 1, including the examples of the compound of Chemical Formula 1 in Chemical Formulas 6A to 6E discussed below. The n-type semiconductor may include sub-phthalocyanine or a sub-phthalocyanine derivative, fullerene or a fullerene derivative, thiophene or a thiophene derivative, or a combination thereof.

After forming the active layer 30 over the first electrode 10, the second electrode 20 may be formed over the active layer 30. For example, the second electrode 20 may be formed by sputtering a transparent conductor, such as indium tin oxide (ITO) or indium zinc oxide (IZO), or a metal layer over the active layer 30.

In some embodiments, the method of manufacturing the photoelectric device 200 in FIG. 2 may further include forming (e.g., coating) a charge auxiliary layer 40 on the first electrode 10 before forming the active layer 30 over the first electrode 10. In some embodiments, the method of manufacturing the photoelectric device 200 may further include forming (e.g., coating) a charge auxiliary layer 45 on the active layer 30 after forming the active layer 30 and before forming the second electrode 20 over the active layer 30.

The photoelectric device may be applied to various fields, for example a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
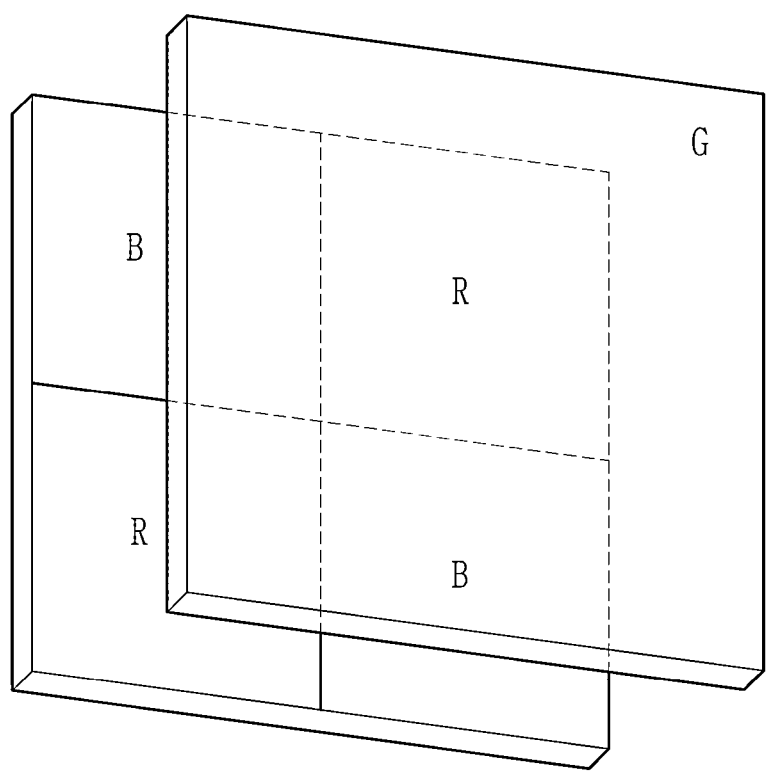
FIG. 3 is a schematic top plan view showing an organic CMOS image sensor according to an embodiment.
Figure 4:
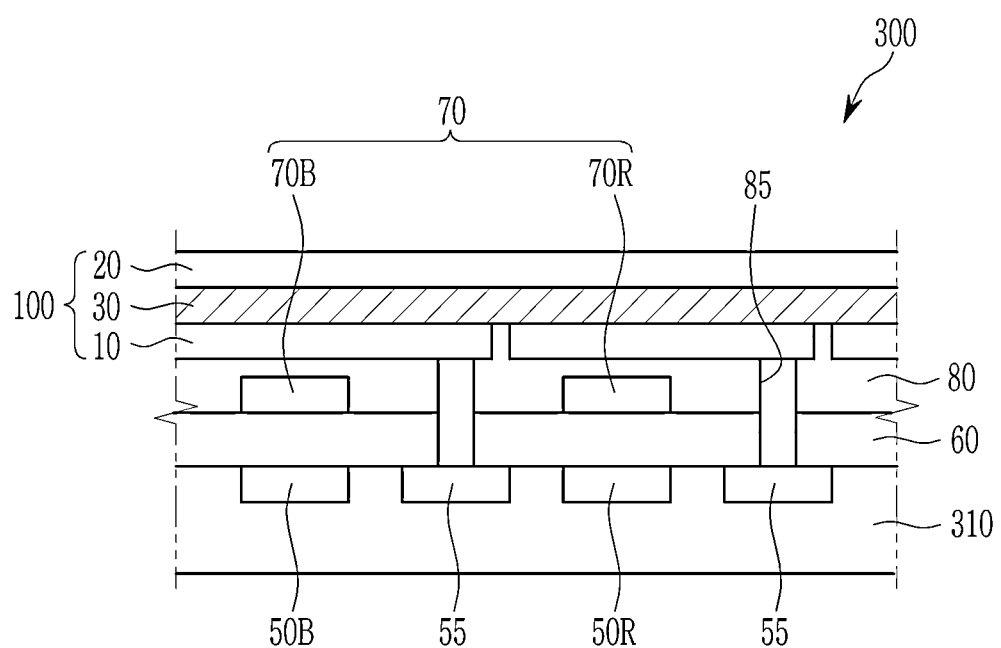
FIG. 4 is a cross-sectional view showing the organic CMOS image sensor of FIG. 3.

FIG. 3 is a schematic top plan view showing an organic CMOS image sensor according to an example embodiment, and FIG. 4 is a cross-sectional view showing the organic CMOS image sensor of FIG. 3.

Referring to FIGS. 3 and 4, an organic CMOS image sensor 300 according to an example embodiment includes a semiconductor substrate 310 integrated with photo-sensing devices 50B and 50R, a transmission transistor (not shown), a charge storage 55, a lower insulation layer 60, a color filter layer 70, an upper insulation layer 80, and a photoelectric device 100.

The semiconductor substrate 310 may be a silicon substrate, and is integrated with the photo-sensing device 50, the transmission transistor (not shown), and the charge storage 55. The photo-sensing devices 50R and 50B may be photodiodes.

The photo-sensing devices 50B and 50R, the transmission transistor, and/or the charge storage 55 may be integrated in each pixel, and as shown in the drawing, the photo-sensing devices 50B and 50R may be respectively included in a blue pixel and a red pixel and the charge storage 55 may be included in a green pixel.

The photo-sensing devices 50B and 50R sense light, the information sensed by the photo-sensing devices may be transferred by the transmission transistor, the charge storage 55 is electrically connected to the photoelectric device 100, and the information of the charge storage 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 310. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70B formed in the blue pixel and configured to selectively transmit blue light and a red filter 70R formed in the red pixel and configured to selectively transmit red light. In an embodiment, a cyan filter 70C and a yellow filter 70Y may be disposed instead of the blue filter 70B and red filter 70R. In the present embodiment, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The aforementioned photoelectric device 100 is formed on the upper insulation layer 80. The photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs and/or senses light in a green wavelength region and replaces a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in the photo-sensing devices 50B and 50R.

As described above, the photoelectric devices configured to selectively absorb light in a green wavelength region are stacked and thereby a size of an image sensor may be decreased and a down-sized image sensor may be realized.

As described above, the compound represented by the Chemical Formula 1 may be used as a semiconductor compound, aggregation between compounds in a thin film state is inhibited, and thereby light absorption characteristics depending on a wavelength may be maintained. Thereby, green wavelength selectivity may be maintained, crosstalk caused by unnecessary absorption of other light except a green wavelength region may be decreased and sensitivity may be increased.

In an embodiment, in FIG. 4, additional color filters may be further disposed on the photoelectric device 100. The additional color filters may include a blue filter 70B and a red filter 70R or a cyan filter 70C and a yellow filter 70Y.

Figure 5:
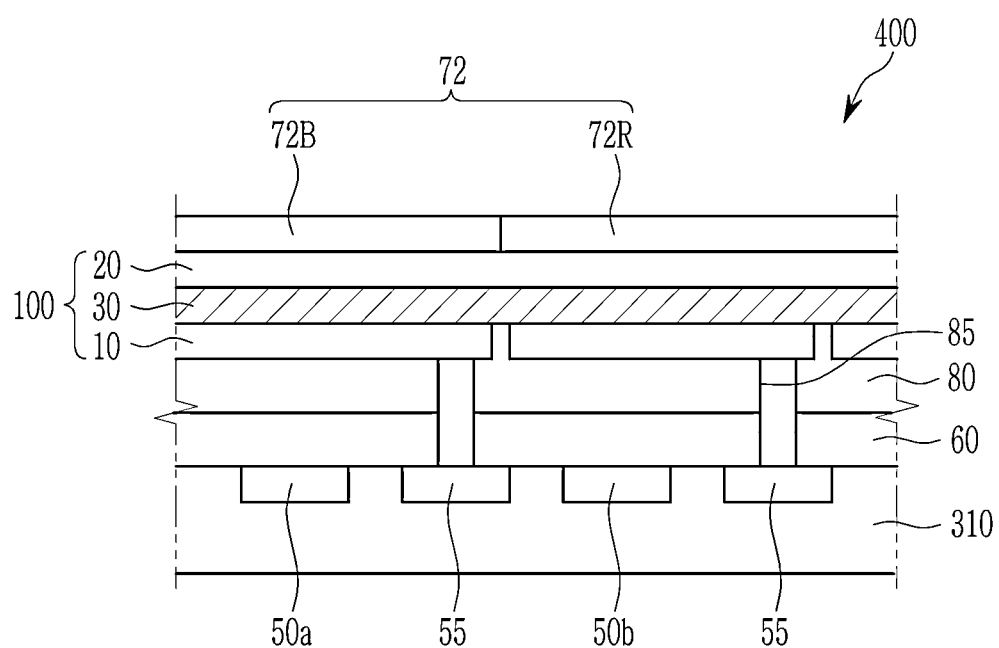
FIG. 5 is a schematic cross-sectional view showing an organic CMOS image sensor according to another embodiment.

The organic CMOS image sensor with the color filters disposed on the photoelectric device is shown in FIG. 5. FIG. 5 is a schematic cross-sectional view showing an organic CMOS image sensor according to an embodiment. Referring to FIG. 5, an organic CMOS image sensor 400 has the same structure as FIG. 4 except that a color filter layer 72 including the blue filter 72B and the red filter 72R is disposed on the photoelectric device 100. Instead of the blue filter 72B and the red filter 72R, the cyan filter 72C and the yellow filter 72Y may be disposed respectively.

Figure 6:
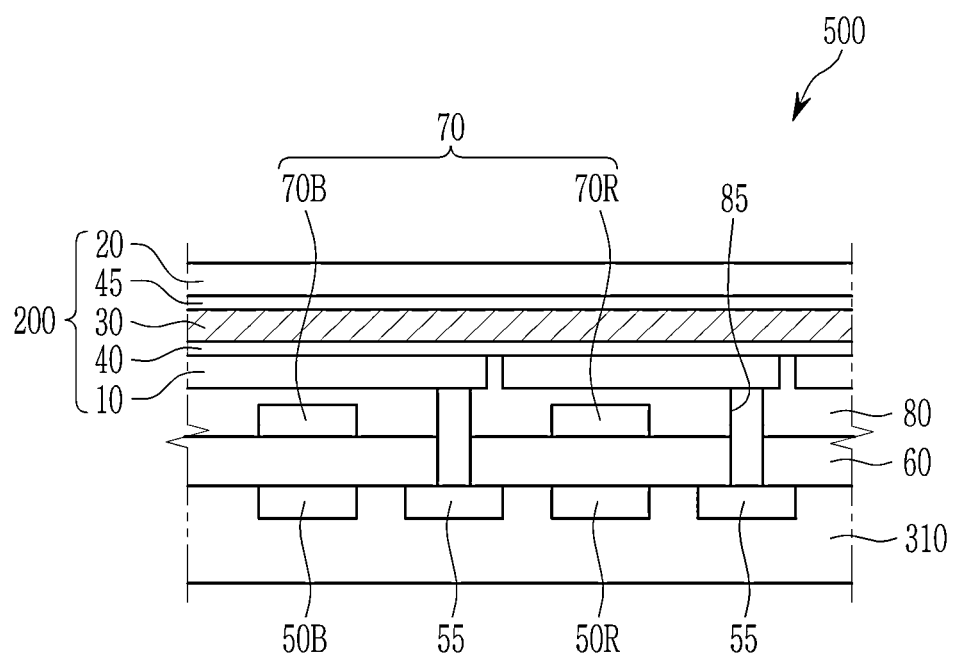
FIG. 6 is a schematic cross-sectional view showing an organic CMOS image sensor according to another embodiment.

In FIGS. 4 and 5, the photoelectric device 100 of FIG. 1 is included, but it is not limited thereto, and thus the photoelectric device 200 of FIG. 2 may be applied in the same manner. FIG. 6 is a cross-sectional view showing an organic CMOS image sensor 500 to which the photoelectric device 200 is applied.

Figure 7:
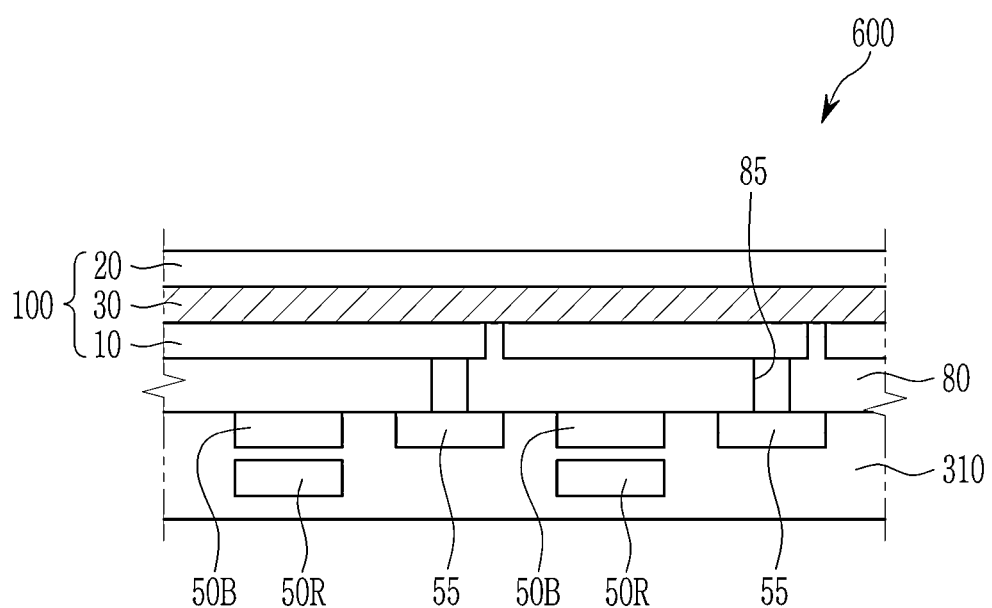
FIG. 7 is a schematic view showing an organic CMOS image sensor according to another embodiment.

FIG. 7 is a schematic view showing an organic CMOS image sensor according to another embodiment.

Referring to FIG. 7, the organic CMOS image sensor 600 includes a semiconductor substrate 310 integrated with photo-sensing devices 50B and 50R, a transmission transistor (not shown), a charge storage 55, an insulation layer 80, and a photoelectric device 100, like the example embodiment illustrated in FIG. 5.

However, the organic CMOS image sensor 600 according to the embodiment includes the blue photo-sensing device 50B and the red photo-sensing device 50R that are stacked and does not include a color filter layer 70, unlike the aforementioned embodiments. The blue photo-sensing device 50B and the red photo-sensing device 50R are electrically connected with the charge storage 55, and the information of the charge storage 55 may be transferred by the transmission transistor (not shown). The blue photo-sensing device 50B and the red photo-sensing device 50R may selectively absorb light in each wavelength region depending on a stack depth.

As described above, the photoelectric devices configured to selectively absorb light in a green wavelength region are stacked and the red photo-sensing device and the blue photo-sensing device are stacked, and thereby a size of an image sensor may be decreased and a down-sized image sensor may be realized. As described above, the photoelectric device 100 has improved green wavelength selectivity, and crosstalk caused by unnecessary absorption light in a wavelength region except green may be decreased while increasing sensitivity.

In FIG. 7, the photoelectric device 100 of FIG. 1 is included, but it is not limited thereto, and thus the photoelectric device 200 of FIG. 2 may be applied in the same manner.

Figure 8:
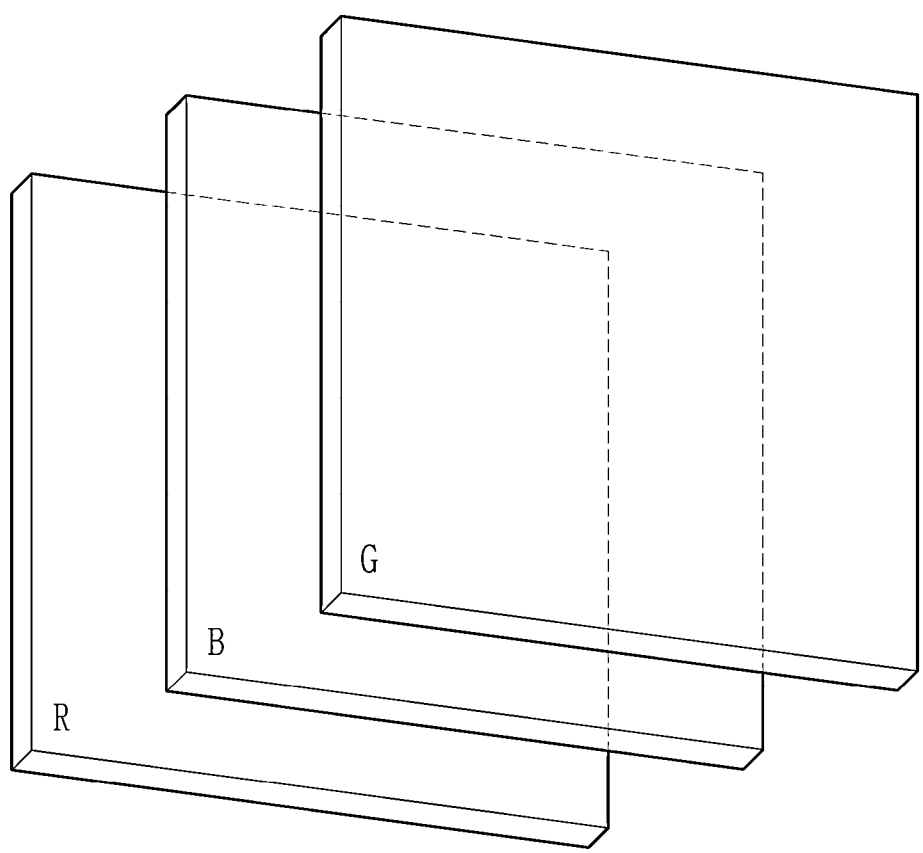
FIG. 8 is a schematic view showing an organic CMOS image sensor according to another embodiment.

FIG. 8 is a schematic view showing an organic CMOS image sensor according to another example embodiment.

Referring to FIG. 8, the organic CMOS image sensor according to the present embodiment includes a green photoelectric device (G) configured to selectively absorb light in a green wavelength region, a blue photoelectric device (B) configured to selectively absorb light in a blue wavelength region, and a red photoelectric device configured to selectively absorb light in a red wavelength region that are stacked.

In the drawing, the red photoelectric device, the green photoelectric device, and the blue photoelectric device are sequentially stacked, but the stack order may be changed without limitation.

The green photoelectric device may be the aforementioned photoelectric device 100 or photoelectric device 200, the blue photoelectric device may include electrodes facing each other and an active layer interposed therebetween and including an organic material configured to selectively absorb light in a blue wavelength region, and the red photoelectric device may include electrodes facing each other and an active layer interposed therebetween and including an organic material configured to selectively absorb light in a red wavelength region.

As described above, the green photoelectric device (G) configured to selectively absorb light in a green wavelength region, the blue photoelectric device (B) configured to selectively absorb light in a red wavelength region, and the red photoelectric device (R) configured to selectively absorb light in a blue wavelength region are stacked, and thereby a size of an image sensor may be decreased and a down-sized image sensor may be realized.

The image sensor absorbs light in an appropriate wavelength region and may show all improved sensitivity (YSNR10) and color reproducibility (ΔE*ab) despite a stack structure.

Herein, the YSNR10 indicates sensitivity of the image sensor, which is measured in a method described in Juha Alakarhu's "Image Sensors and Image Quality in Mobile Phones" printed in 2007 International Image Sensor Workshop (Ogunquit Maine, USA) but minimum illuminance expressed by lux at a ratio of 10 between signal and noise. Accordingly, the smaller the YSNR10 is, the higher sensitivity is.

On the other hand, the color reproducibility (ΔE*ab) shows a difference from standard colors in an X-Rite chart, and the ΔE*ab is defined as a distance between two points on a L*a*b* color space by CIE (Commission International de L' Eclairage) in 1976. For example, the color difference may be calculated according to Equation 1.

$$\Delta E = \sqrt{(\Delta L^*)^2 + (\Delta a^*)^2 + (\Delta b^*)^2} \quad \text{[Equation 1]}$$

In Equation 1,
ΔL* denotes a change of a color coordinate L* compared with the color coordinate L* at room temperature (about 20° C. to about 25° C.),
Δa* denotes a change of a color coordinate a* compared with the color coordinate a*at room temperature, and
Δb* denotes a change of a color coordinate b* compared with the color coordinate b*at room temperature.

In order to manufacture an image sensor having high sensitivity and high color reproducibility, YSNR10≤100 lux at ΔE*ab≤3, and herein, the compound may realize YSNR105100 lux of sensitivity and color reproducibility at ΔE*ab≤3.

The image sensor may be applied to various electronic devices, for example, a mobile phone, a digital camera, and the like but is not limited thereto.

Figure 9:
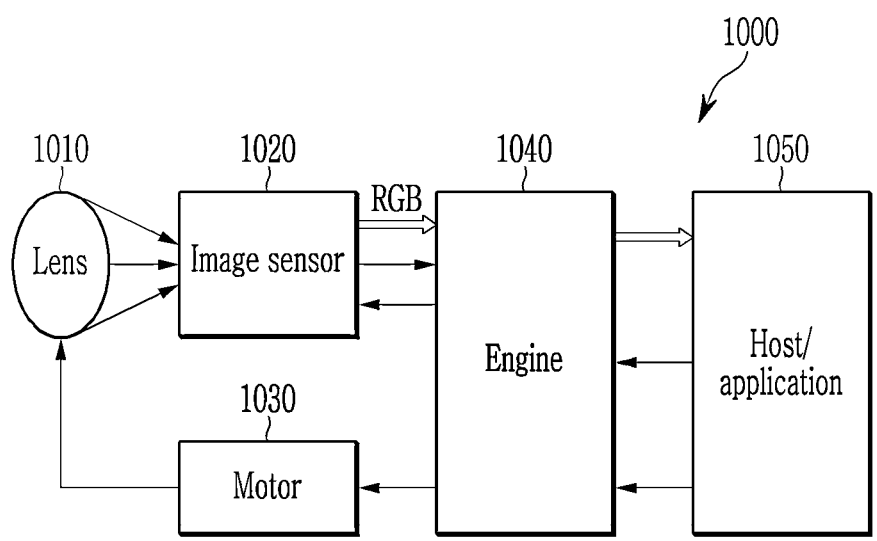
FIG. 9 is a block diagram of a digital camera including an image sensor according to an embodiment.

FIG. 9 is a block diagram of a digital camera including an image sensor according to an embodiment.

Referring to FIG. 9, a digital camera 1000 includes a lens 1010, an image sensor 1020, a motor unit 1030, and an engine unit 1040. The image sensor 1020 may be one of image sensors according to embodiments shown in FIGS. 3 to 8.

The lens 1010 concentrates incident light on the image sensor 1020. The image sensor 1020 generates RGB data for received light through the lens 1010.

In some embodiments, the image sensor 1020 may interface with the engine 1040.

The motor 1030 may adjust the focus of the lens 1010 or perform shuttering in response to a control signal received from the engine 1040. The engine 1040 may control the image sensor 1020 and the motor unit 1030.

The engine 1040 may be connected to a host/application 1050.

Figure 10:
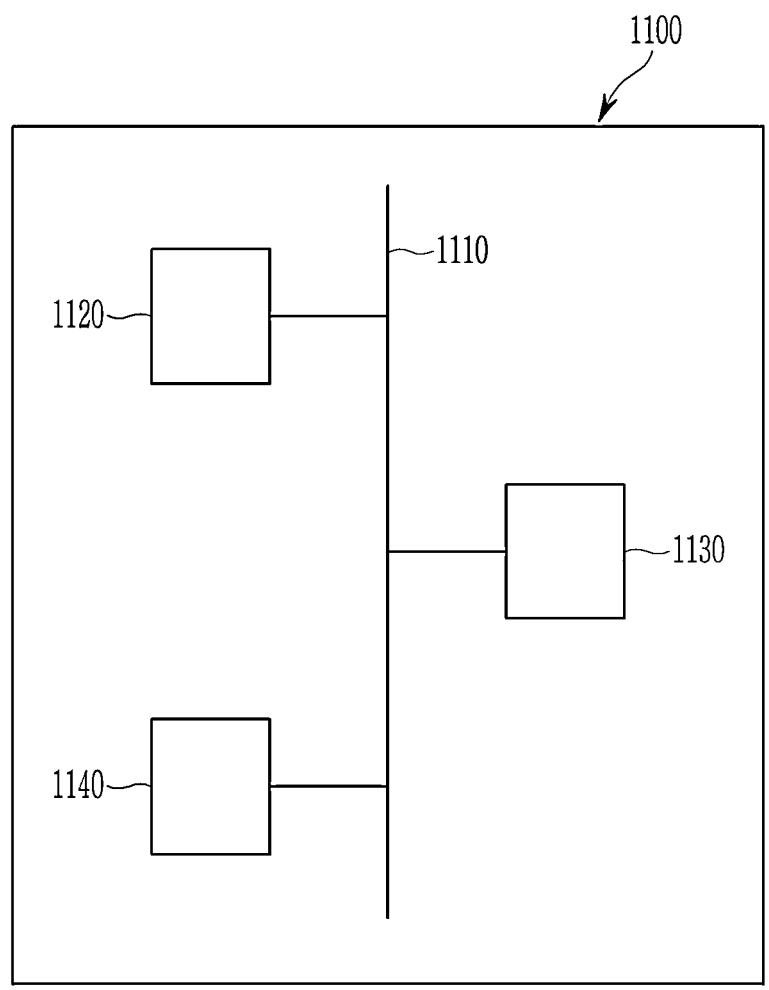
FIG. 10 is a schematic diagram showing an electronic device according to some embodiments.

FIG. 10 is a schematic diagram showing an electronic device according to some embodiments. Referring to FIG. 10, an electronic device 1100 may include a processor 1120, a memory 1130, and an image sensor 1140 that are electrically coupled together via a bus 1110. The image sensor 1140 may be one according to one of the aforementioned embodiments. The memory 1130, which may be a non-transitory computer readable medium and may store a program of instructions. The memory 1130 may be a non-volatile memory, such as a flash memory, a phase-change random access memory (PRAM), a magneto-resistive RAM (MRAM), a resistive RAM (ReRAM), or a ferro-electric RAM (FRAM), or a volatile memory, such as a static RAM (SRAM), a dynamic RAM (DRAM), or a synchronous DRAM (SDRAM). The processor 1120 may execute the stored program of instructions to perform one or more functions. For example, the processor 1120 may be configured to process electrical signals generated by the organic sensor 1140. The processor 1120 may include processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc. The processor 1120 may be configured to generate an output (e.g., an image to be displayed on a display interface) based on such processing.

Hereinafter, the embodiments are illustrated in more detail with reference to examples. However, these examples are non-limiting, and inventive concepts are not limited thereto.

Synthesis Example 1: Synthesis of Compound Represented by Chemical Formula 1-1

[Chemical Formula 1-1]

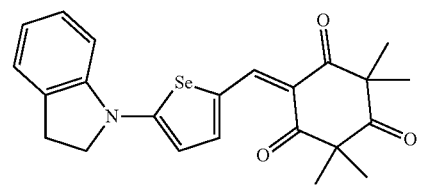

-continued
[Reaction Scheme 1-1]

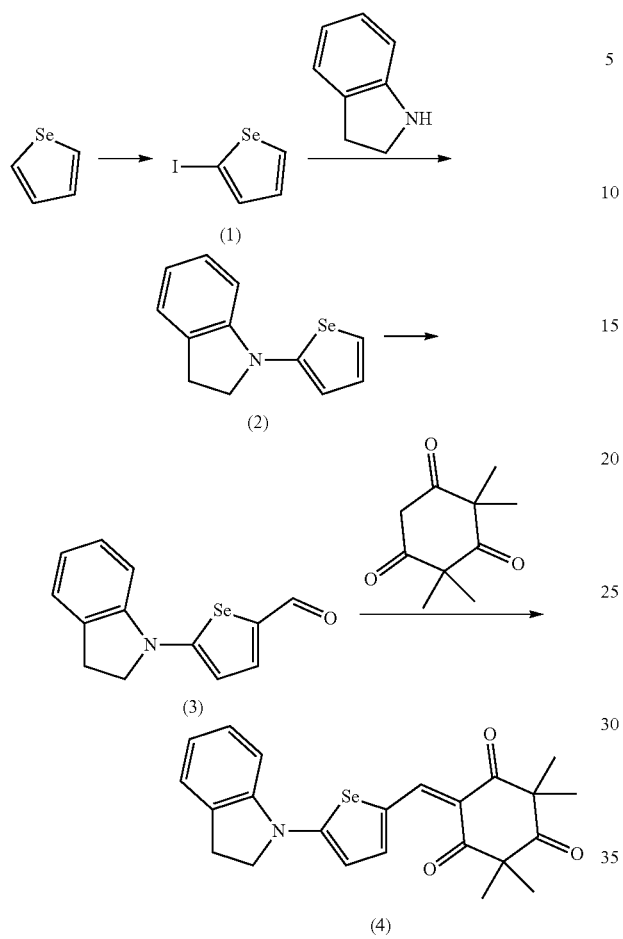

(i) Synthesis of Compound (1)

2-iodoselenophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

10.0 g (38.9 mmol) of 2-iodoselenophene and 4.22 g (35.4 mmol) of indoline are heated and refluxed in 100 ml of anhydrous toluene under the presence of 1.77 mmol of Pd(dba)$_2$, 1.77 mmol of P(tBu)$_3$, and 10.2 g (106.15 mmol) of NaOtBu for 2 hours. A product obtained therefrom is separated and purified through silica gel column chromatography (toluene:hexane=1:4 in a volume ratio) to obtain 5.21 g (Yield=59.3%) of 1-(selenophen-2-yl)indoline.

(iii) Synthesis of Compound (3)

10.2 ml of phosphoryl chloride is added in a dropwise fashion to 20.0 ml of N,N-dimethylformamide at −15° C. and then, stirred at room temperature (24° C.) for 2 hours. The obtained resultant is slowly added in a dropwise fashion to a mixture of 160 ml of dichloromethane and 5.0 g of Compound (2) at −15° C. and then, stirred at room temperature for 30 minutes and concentrated under a reduced pressure.

Subsequently, 200 ml of water is added thereto, and an aqueous sodium hydroxide solution is added thereto until pH becomes 14 and then, stirred at room temperature (24° C.) for 2 hours. An organic layer extracted with dichloromethane therefrom is washed with an aqueous sodium chloride solution and then, dried by adding magnesium sulfate anhydrous thereto. A product obtained therefrom is separated and purified through silica gel column chromatography (hexane:ethylacetate=4:1 in a volume ratio) to obtain 3.52 g (Yield: 63.2%) of 5-(indolin-1-yl)selenophene-2-carbaldehyde.

(iv) Synthesis of Compound (4) Represented by Chemical Formula 1-1

3.00 g (9.56 mmol) of Compound (3) is suspended in ethanol, and 1.92 g (10.5 mmol) of 2,2,4,4-tetramethylcyclohexane-1,3,5-trione is added thereto and then, reacted at 50° C. for 2 hours to obtain 2.98 g (Yield: 70.8%) of a final compound represented by Chemical Formula 1-1. The compound is sublimed and purified up to purity of 99.9%.

$^1$H-NMR (500 MHz, Methylene Chloride-d$_2$): δ 8.32 (s, 1H), 8.04 (d, 1H), 7.67 (d, 1H), 7.43 (t, 1H), 7.40 (d, 1H), 7.36 (t, 1H), 6.83 (d, 1H), 4.27 (t, 2H), 3.38 (t, 2H), 1.38 (d, 12H).

Synthesis Example 2: Synthesis of Compound Represented by Chemical Formula 1-2

[Chemical Formula 1-2]

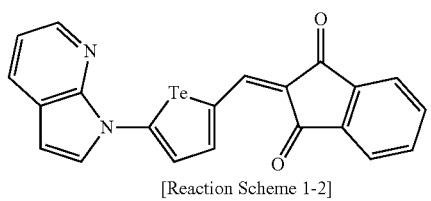

[Reaction Scheme 1-2]

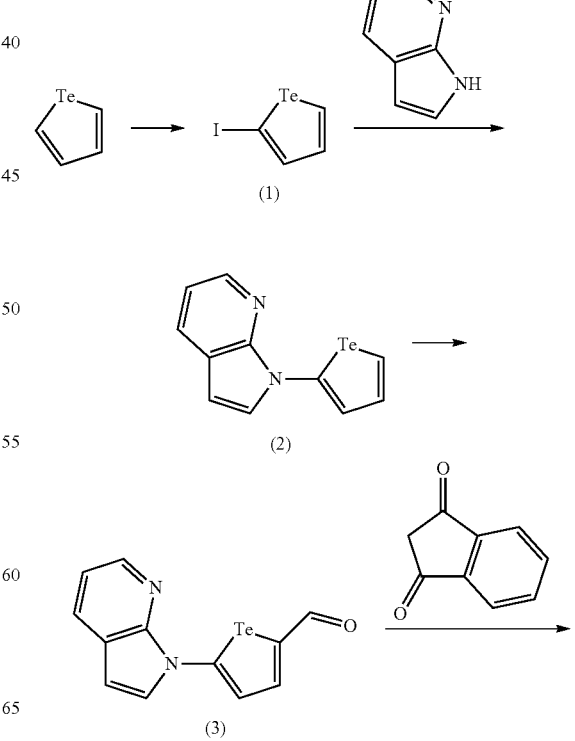

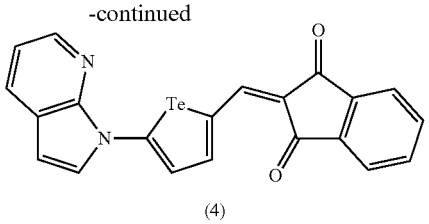

(4)

(i) Synthesis of Compound (1)

2-iodotellurophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

10.0 g (32.7 mmol) of 2-iodotellurophene and 3.5 g (32.7 mmol) of 1H-pyrrolo[2,3-b]pyridine are heated and refluxed in 100 ml of anhydrous toluene under the presence of 1.64 mmol of Pd(dba)$_2$, 1.64 mmol of P(tBu)$_3$, and 8.6 g (96.1 mmol) of NaOtBu for 6 hours. The obtained product is separated and purified through silica gel column chromatography (toluene:hexane=1:4 in a volume ratio) to obtain 5.2 g (Yield=59.4%) of 1-(tellurophene-2-yl)-1H-pyrrolo[2,3-b]pyridine.

(iii) Synthesis of Compound (3)

10.0 ml of N,N-dimethylformamide is added in a dropwise fashion to 4.9 ml of phosphoryl chloride at −15° C. and then, stirred at room temperature (24° C.) for 2 hours. The obtained resultant is slowly added to a mixture of 100 ml of dichloromethane and 2.0 g of Compound (2) at −15° C. and then, stirred at room temperature for 30 minutes and concentrated under a reduced pressure. Subsequently, 200 ml of water is added thereto, and an aqueous sodium hydroxide solution is added thereto until pH becomes 14 and then, stirred at room temperature (24° C.) for 2 hours. An organic layer extracted with dichloromethane therefrom is washed with an aqueous sodium chloride solution and then, dried by adding magnesium sulfate anhydrous thereto. A product obtained therefrom is separated and purified through silica gel column chromatography (hexane:ethylacetate=4:1 in a volume ratio) to obtain 1.4 g (Yield: 63.9%) of 5-(1H-pyrrolo[2,3-b]pyridine-1-yl)tellurophene-2-carbaldehyde).

(iv) Synthesis of Compound (4) Represented by Chemical Formula 1-2

1.4 g (3.80 mmol) of Compound (3) is suspended in ethanol, and 0.61 g (4.18 mmol) of 1H-indene-1,3(2H)-dione is added thereto and then, reacted at 50° C. for 2 hours to obtain 1.08 g (Yield: 62.8%) of a final compound represented by Chemical Formula 1-2. The compound is sublimed and purified up to purity of 99.9%.

$^1$H-NMR (500 MHz, Methylene Chloride-d$_2$): δ 8.67 (d, 1H), 8.60 (d, 1H), 8.18 (s, 1H), 8.09 (d, 1H), 7.98 (d, 1H), 7.92 (m, 1H), 7.88 (m, 1H), 7.83 (d, 1H), 7.76 (m, 2H), 7.35 (m, 1H), 6.83 (d, 1H)

Synthesis Example 3: Synthesis of Compound Represented by Chemical Formula 1-3

[Chemical Formula 1-3]

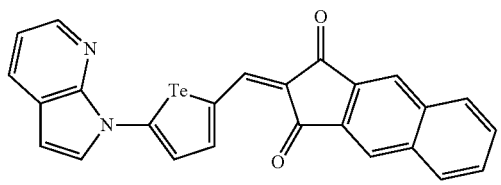

[Reaction Scheme 1-3]

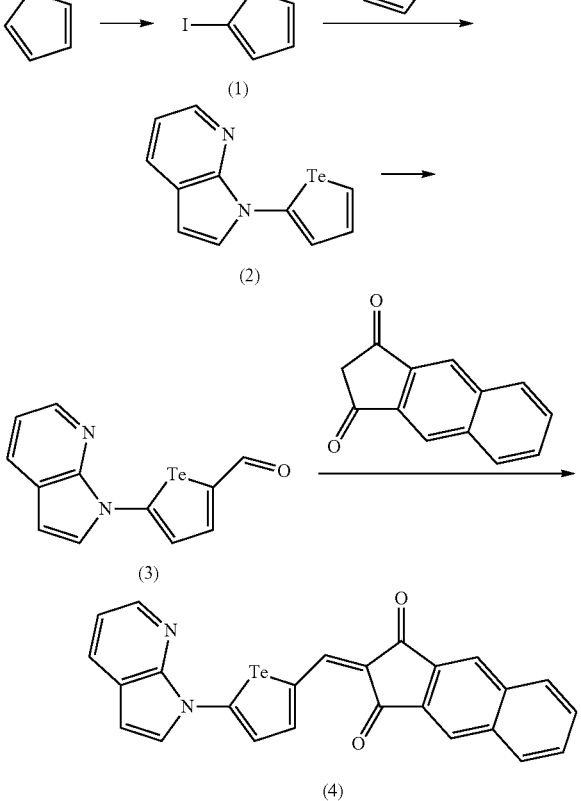

(i) Synthesis of Compound (1)

2-iodotellurophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

10.0 g (32.7 mmol) of 2-iodotellurophene and 3.5 g (32.7 mmol) of 1H-pyrrolo[2,3-b]pyridine is heated and refluxed in 100 ml of anhydrous toluene under the presence of 1.64 mmol of Pd(dba)$_2$, 1.64 mmol pf P(tBu)$_3$, and 8.6 g (96.1 mmol) of NaOtBu for 6 hours. The obtained product is separated and purified through silica gel column chromatography (toluene:hexane=1:4 in a volume ratio) to obtain 5.2 g (Yield: 59.4%) of 1-(tellurophene-2-yl)-1H-pyrrolo[2,3-b]pyridine.

(iii) Synthesis of Compound (3)

4.9 ml of phosphoryl chloride is added in a dropwise fashion to 10.0 ml of N,N-dimethylformamide at −15° C. and then, stirred at room temperature (24° C.) for 2 hours. The obtained resultant is slowly added in a dropwise fashion to a mixture of 100 ml of dichloromethane and 2.0 g of Compound (2) at −15° C. and then, stirred at room temperature for 30 minutes and concentrated under a reduced pressure. Subsequently, 200 ml of water is added thereto, and an aqueous sodium hydroxide solution is added thereto until pH becomes 14 and then, stirred at room temperature (24° C.) for 2 hours. An organic layer extracted with dichloromethane therefrom is washed with an aqueous sodium chloride solution and then, dried by adding magnesium sulfate anhydrous thereto. A product obtained therefrom is separated and purified through silica gel column chromatography (hexane:ethylacetate=4:1 in a volume ratio) to obtain 1.4 g (Yield: 63.9%) of 5-(1H-pyrrolo[2,3-b]pyridine-1-yl)tellurophene-2-carbaldehyde).

(iv) Synthesis of Compound (4) Represented by Chemical Formula 1-3 1.4 g (3.80 mmol) of Compound (3) is suspended in ethanol, and 0.82 g (4.18 mmol) of 1H-cyclopenta[b]naphthalene-1,3(2H)-dione is added thereto and then, reacted at 50° C. for 2 hours to obtain 1.12 g (Yield: 58.7%) of a final compound represented by Chemical Formula 1-3. The compound is sublimed and purified up to purity of 99.9%.

Synthesis Example 4: Synthesis of Compound Represented by Chemical Formula 1-4

[Chemical Formula 1-4]

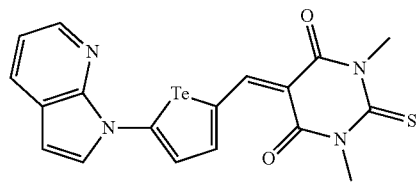 [SMILES: CC1(C)C(=O)C(=Cc2ccc(N3CCc4ccccc43)[se]2)C(=O)C(C)(C)C1=O]

[Reaction Scheme 1-4]

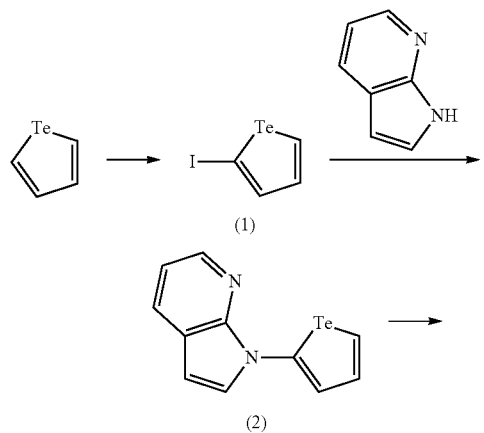

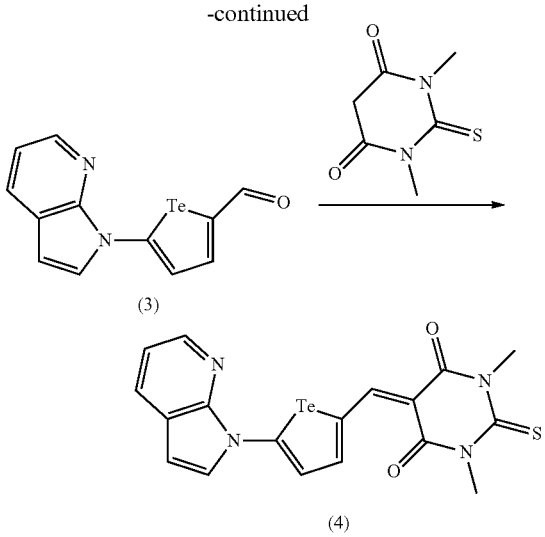

(i) Synthesis of Compound (1)

2-iodotellurophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

10.0 g (32.7 mmol) of 2-iodotellurophene and 3.5 g (32.7 mmol) of 1H-pyrrolo[2,3-b]pyridine are heated and refluxed in 100 ml of anhydrous toluene under the presence of 1.64 mmol of $Pd(dba)_2$, 1.64 mmol of $P(tBu)_3$, and 8.6 g (96.1 mmol) of NaOtBu for 6 hours. The obtained product is separated and purified through silica gel column chromatography (toluene:hexane=1:4 in a volume ratio) to obtain 5.2 g (Yield: 59.4%) of 1-(tellurophene-2-yl)-1H-pyrrolo[2,3-b]pyridine.

(iii) Synthesis of Compound (3)

4.9 ml of phosphoryl chloride is added in a dropwise fashion to 10.0 ml of N,N-dimethylformamide at −15° C. and then, stirred at room temperature (24° C.) for 2 hours. The obtained resultant is slowly added in a dropwise fashion to a mixture of 100 ml of dichloromethane and 2.0 g of Compound (2) at −15° C. and then, stirred at room temperature for 30 minutes and concentrated under a reduced pressure. Subsequently, 200 ml of water is added thereto, and an aqueous sodium hydroxide solution is added thereto until pH becomes 14 and then, stirred at room temperature (24° C.) for 2 hours. An organic layer extracted with dichloromethane therefrom is washed with an aqueous sodium chloride solution and then, dried by adding magnesium sulfate anhydrous thereto. A product obtained therefrom is separated and purified through silica gel column chromatography (hexane:ethylacetate=4:1 in a volume ratio) to obtain 1.4 g (Yield: 63.9%) of 5-(1H-pyrrolo[2,3-b]pyridine-1-yl)tellurophene-2-carbaldehyde).

(iv) Synthesis of Compound (4) Represented by Chemical Formula 1-4

1.4 g (3.80 mmol) of Compound (3) is suspended in ethanol, and 0.72 g (4.18 mmol) of 1,3-dimethyl-2-thioxo-dihydropurimidine-4,6(1H,5H)-dione is added thereto and then, reacted at 50° C. for 2 hours to obtain 1.10 g (Yield: 60.5%) of a final compound represented by Chemical Formula 1-4. The compound is sublimed and purified up to purity of 99.9%.

Synthesis Example 5: Synthesis of Compound Represented by Chemical Formula 1-5

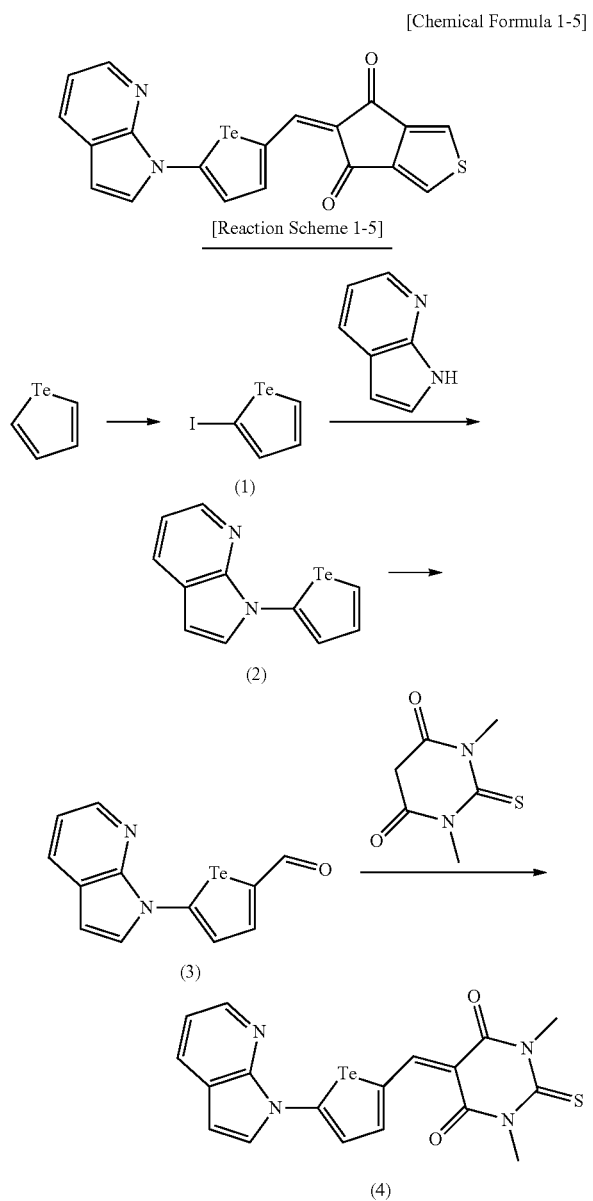

[Chemical Formula 1-5]

[Reaction Scheme 1-5]

(i) Synthesis of Compound (1)

2-iodotellurophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

10.0 g (32.7 mmol) of 2-iodotellurophene and 3.5 g (32.7 mmol) of 1H-pyrrolo[2,3-b]pyridine are heated and refluxed in 100 ml of anhydrous toluene under the presence of 1.64 mmol of Pd(dba)$_2$, 1.64 mmol of P(tBu)$_3$, and 8.6 g (96.1 mmol) of NaOtBu for 6 hours. The obtained product is separated and purified through silica gel column chromatography (toluene:hexane=1:4 in a volume ratio) to obtain 5.2 g (Yield: 59.4%) of 1-(tellurophene-2-yl)-1H-pyrrolo[2,3-b]pyridine.

(iii) Synthesis of Compound (3)

4.9 ml of phosphoryl chloride is added in a dropwise fashion to 10.0 ml of N,N-dimethylformamide at −15° C. and then, stirred at room temperature (24° C.) for 2 hours. The obtained resultant is slowly added in a dropwise fashion to a mixture of 100 ml of dichloromethane and 2.0 g of Compound (2) at −15° C. and then, stirred at room temperature for 30 minutes and concentrated under a reduced pressure. Subsequently, 200 ml of water is added thereto, and an aqueous sodium hydroxide solution is added thereto until pH becomes 14 and then, stirred at room temperature (24° C.) for 2 hours. Then, an organic layer extracted with dichloromethane therefrom is washed with an aqueous sodium chloride solution and then, dried by adding magnesium sulfate anhydrous thereto. A product obtained therefrom is separated and purified through silica gel column chromatography (hexane:ethylacetate=4:1 in a volume ratio) to obtain 1.4 g (Yield: 63.9%) of 5-(1H-pyrrolo[2,3-b]pyridine-1-yl)tellurophene-2-carbaldehyde).

(iv) Synthesis of Compound (4) Represented by Chemical Formula 1-5

1.4 g (3.80 mmol) of Compound (3) is suspended in ethanol, and 0.64 g (4.18 mmol) of 4H-cyclopenta[c]thiophene-4,6(5H)dione is added thereto and then, reacted at 50° C. for 2 hours to obtain 1.13 g (Yield: 64.9%) of a final compound represented by Chemical Formula 1-5. The obtained compound is sublimed and purified up to purity of 99.9%.

Reference Synthesis Example 1: Synthesis of Compound Represented by Chemical Formula 2-1

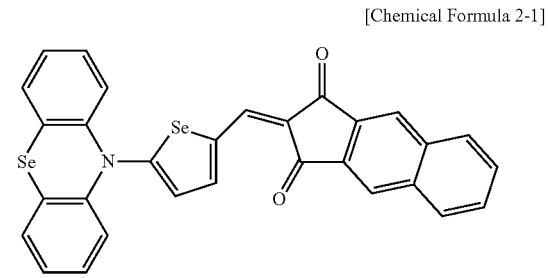

[Chemical Formula 2-1]

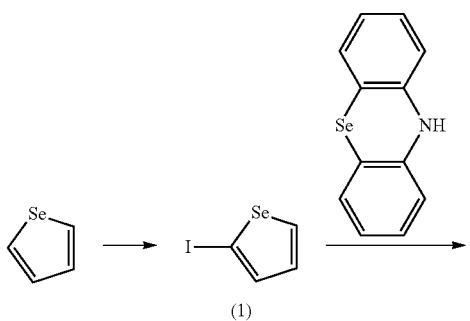

[Reaction Scheme 2-1]

-continued

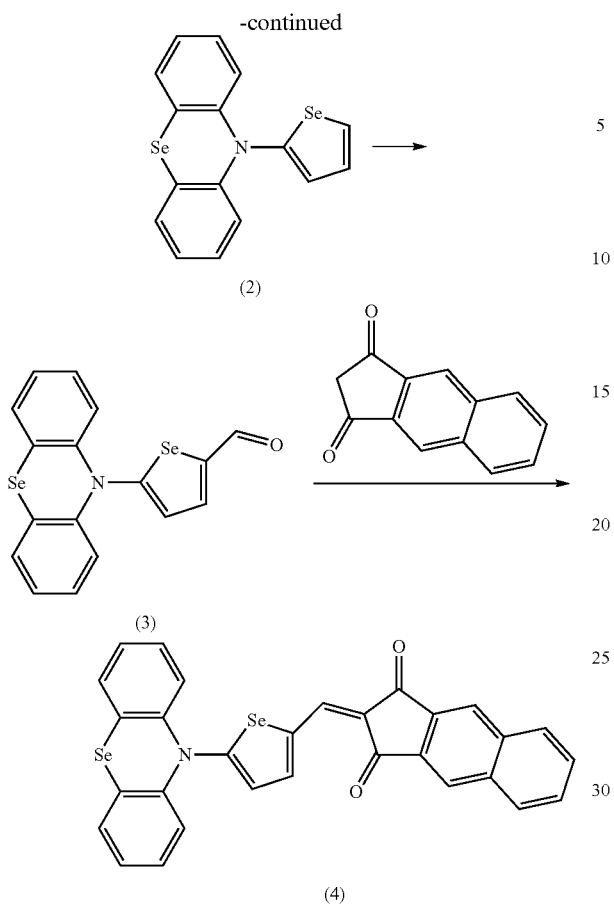

(i) Synthesis of Compound (1)
2-iodoselenophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)
10.0 g (38.9 mmol) of 2-iodoselenophene and 8.71 g (35.4 mmol) of 10H-phenoselenazine are heated and refluxed in 100 ml of anhydrous toluene under the presence of 1.77 mmol of $Pd(dba)_2$, 1.77 mmol of $P(tBu)_3$, and 10.2 g (106.15 mmol) of NaOtBu for 2 hours. The obtained product is separated and purified through silica gel column chromatography (toluene:hexane=1:4 in a volume ratio) to obtain 8.2 g (Yield: 54.7%) of 10-(selenophen-2-yl)-10H-phenoselenazine.

(iii) Synthesis of Compound (3)
8.0 ml of phosphoryl chloride is added in a dropwise fashion to 30.0 ml of N,N-dimethylformamide at −15° C. and then, stirred at room temperature (24° C.) for 2 hours. The obtained resultant is slowly added in a dropwise fashion to a mixture of 180 ml of dichloromethane and 8.2 g of Compound (2) at −15° C. and then, stirred at room temperature for 30 minutes and concentrated under a reduced pressure. Subsequently, 200 ml of water is added thereto, and an aqueous sodium hydroxide solution is added thereto until pH becomes 14 and then, stirred at room temperature (24° C.) for 2 hours. An organic layer extracted with dichloromethane therefrom is washed with an aqueous sodium chloride solution and then, dried by adding magnesium sulfate anhydrous thereto. A product obtained therefrom is separated and purified through silica gel column chromatography (hexane:ethylacetate=4:1 in a volume ratio) to obtain 4.5 g (Yield: 51.1%) of 5-(10H-phenoselenazin-10-yl)selenophene-2-carbaldehyde.

(iv) Synthesis of Compound (4) Represented by Chemical Formula 2-1
2.00 g (5.33 mmol) of Compound (3) is suspended in ethanol, and 1.10 g (5.60 mmol) of 1H-cyclopenta[b]naphthalene-1,3(2H)-dione is added thereto and then, reacted at 50° C. for 2 hours to obtain 2.38 g (Yield: 75.2%) of a final compound represented by Chemical Formula 2-1. The compound is sublimed and purified up to purity of 99.9%.

Reference Synthesis Example 2: Synthesis of Compound Represented by Chemical Formula 2-2

[Chemical Formula 2-2]

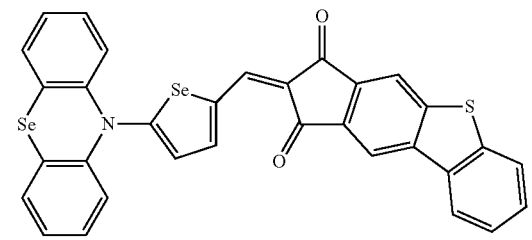

[Reaction Scheme 2-2]

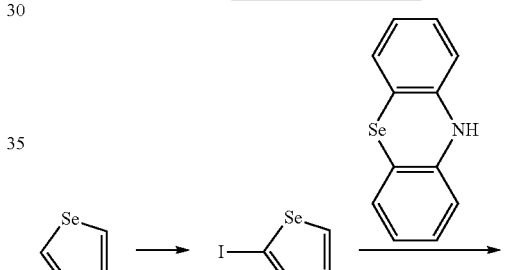

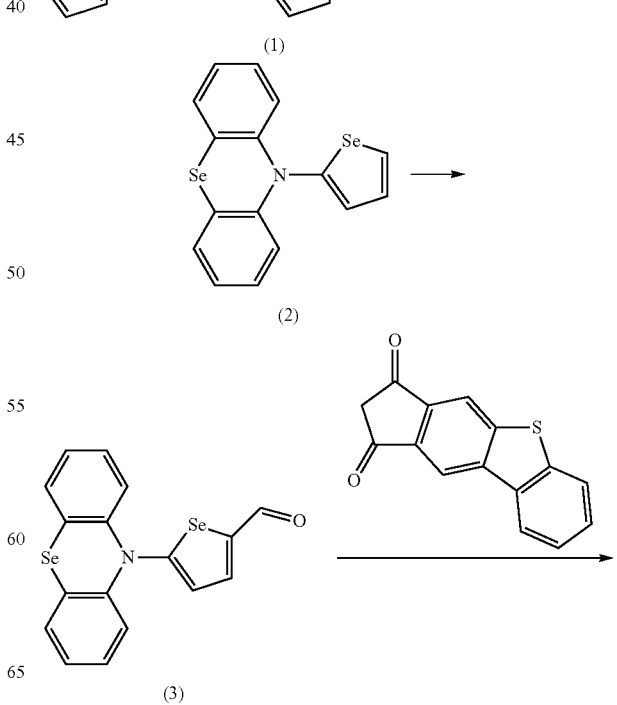

-continued

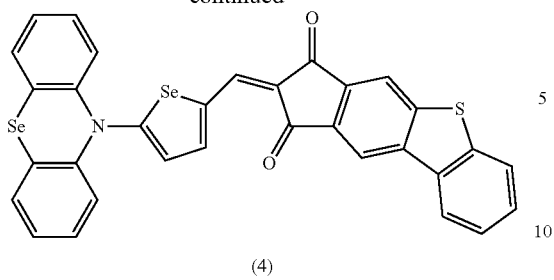

(4)

(i) Synthesis of Compound (1)

2-iodoselenophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

10.0 g (38.9 mmol) of 2-iodoselenophene and 8.71 g (35.4 mmol) of 10H-phenoselenazine are heated and refluxed in 100 ml of anhydrous toluene under the presence of 1.77 mmol of Pd(dba)$_2$, 1.77 mmol of P(tBu)$_3$, and 10.2 g (106.15 mmol) of NaOtBu for 2 hours. The obtained product is separated and purified through silica gel column chromatography (toluene:hexane=1:4 in a volume ratio) to obtain 8.2 g (Yield: 54.7%) of 10-(selenophen-2-yl)-10H-phenoselenazine.

(iii) Synthesis of Compound (3)

8.0 ml of phosphoryl chloride is added in a dropwise fashion to 30.0 ml of N,N-dimethylformamide at −15° C. and then, stirred at room temperature (24° C.) for 2 hours. The obtained resultant is slowly added in a dropwise fashion to a mixture of 180 ml of dichloromethane and 8.2 g of Compound (2) at −15° C. and then, stirred at room temperature for 30 minutes and concentrated under a reduced pressure. Subsequently, 200 ml of water is added thereto, and an aqueous sodium hydroxide solution is added thereto until pH becomes 14 and then, stirred at room temperature (24° C.) for 2 hours. An organic layer extracted with dichloromethane is washed with an aqueous sodium chloride solution and then, dried by adding magnesium sulfate anhydrous thereto. A product obtained therefrom is separated and purified through silica gel column chromatography (hexane: ethylacetate=4:1 in a volume ratio) to obtain 4.5 g (Yield: 51.1%) of 5-(10H-phenoselenazin-10-yl) selenophene-2-carbaldehyde.

(iv) Synthesis of Compound (4) Represented by Chemical Formula 2-2

2.00 g (5.33 mmol) of Compound (3) is suspended in ethanol, and 1.41 g (5.60 mmol) of 1H-benzo[b]indeno[5,6-d]thiophene-1,3(2H)-dione is added thereto and then, reacted at 50° C. for 2 hours to obtain 2.17 g (Yield: 63.9%) of a final compound represented by Chemical Formula 2-2. The compound is sublimed and purified up to purity of 99.9%.

Reference Synthesis Example 3: Synthesis of Compound Represented by Chemical Formula 2-3

[Chemical Formula 2-3]

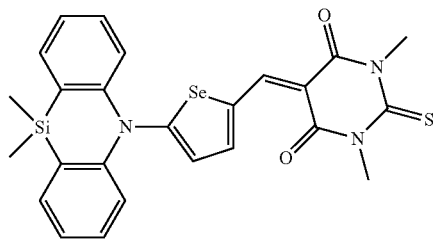

[Reaction Scheme 2-3]

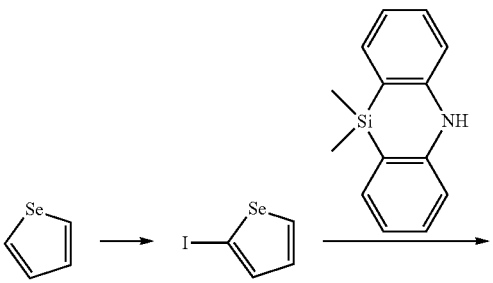

(1)

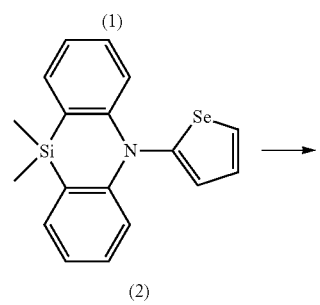

(2)

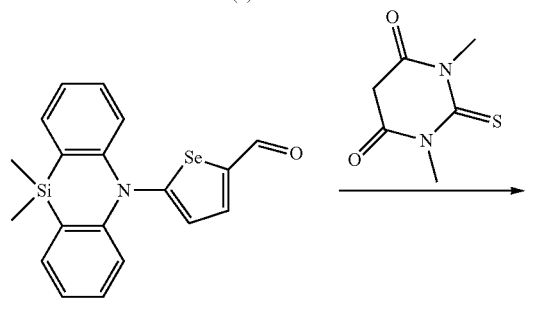

(3)

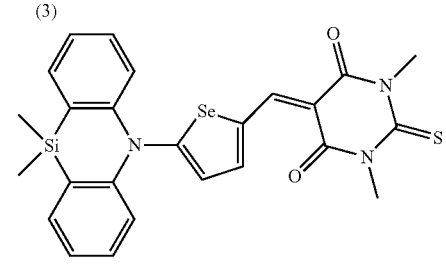

(4)

(i) Synthesis of Compound (1)

2-iodoselenophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

15.0 g (58.4 mmol) of 2-iodoselenophene and 11.9 g (58.4 mmol) of 10,10-dimethyl-5,10-dihydrodibenzo[b,e][1,4]azasiline are heated and refluxed in 200 ml of anhydrous toluene under the presence of 2.92 mmol of Pd(dba)$_2$, 2.92 mmol of P(tBu)$_3$, and 15.3 g (159.22 mmol) of NaOtBu for 2 hours. A product obtained therefrom is separated and purified through silica gel column chromatography (toluene:hexane=1:4 in a volume ratio) to obtain 11.2 g of 10,10-dimethyl-5-(selenophen-2-yl)-5,10-dihydrodibenzo[b,e][1,4]azasiline (Yield: 49.0%).

(iii) Synthesis of Compound (3)

8.2 ml of phosphoryl chloride is added in a dropwise fashion to 38.0 ml of N,N-dimethylformamide at −15° C. and then, stirred at room temperature (24° C.) for 2 hours. The obtained resultant is slowly added in a dropwise fashion to 300 ml of dichloromethane and 11.2 g of Compound 2 at −15° C. and then, stirred at room temperature for 30 minutes and concentrated under a reduced pressure. Subsequently, 300 ml of water is added thereto, and an aqueous sodium hydroxide solution is added thereto until pH becomes 14 and then, stirred at room temperature (24° C.) for 2 hours. An organic layer extracted with dichloromethane is washed with an aqueous sodium chloride solution and then, washed by adding magnesium sulfate anhydrous thereto. A product obtained therefrom is separated and purified through silica gel column chromatography (hexane:ethylacetate=4:1 in a volume ratio) to obtain 6.82 g (Yield: 54.0%) of 5-(10,10-dimethyldibenzo[b,e][1,4]azasilin-5(10H)-yl)selenophene-2-carbaldehyde.

(iv) Synthesis of Compound 4 represented by Chemical Formula 2-3

3.00 g (7.85 mmol) of Compound (3) is suspended in ethanol, and 1.62 g (9.41 mmol) of 1,3-dimethyl-2-thiobabituric acid is added thereto and then, reacted at 50° C. for 2 hours to obtain 3.15 g (Yield: 74.8%) of a final compound represented by Chemical Formula 2-3. The compound is sublimed and purified up to purity of 99.9%.

$^1$H-NMR (500 MHz, Methylene Chloride-d$_2$): δ 8.46 (s, 1H), 8.26 (d, 1H), 7.80 (d, 2H), 7.71 (d, 2H), 7.56 (t, 2H), 7.50 (t, 2H), 6.93 (d, 1H), 3.68 (d, 6H), 0.45 (s, 6H).

Reference Synthesis Example 4: Synthesis of Compound Represented by Chemical Formula 2-4

[Chemical Formula 2-4]

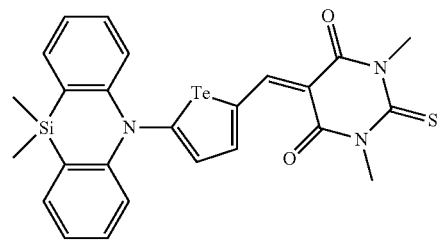

[Reaction Scheme 2-4]

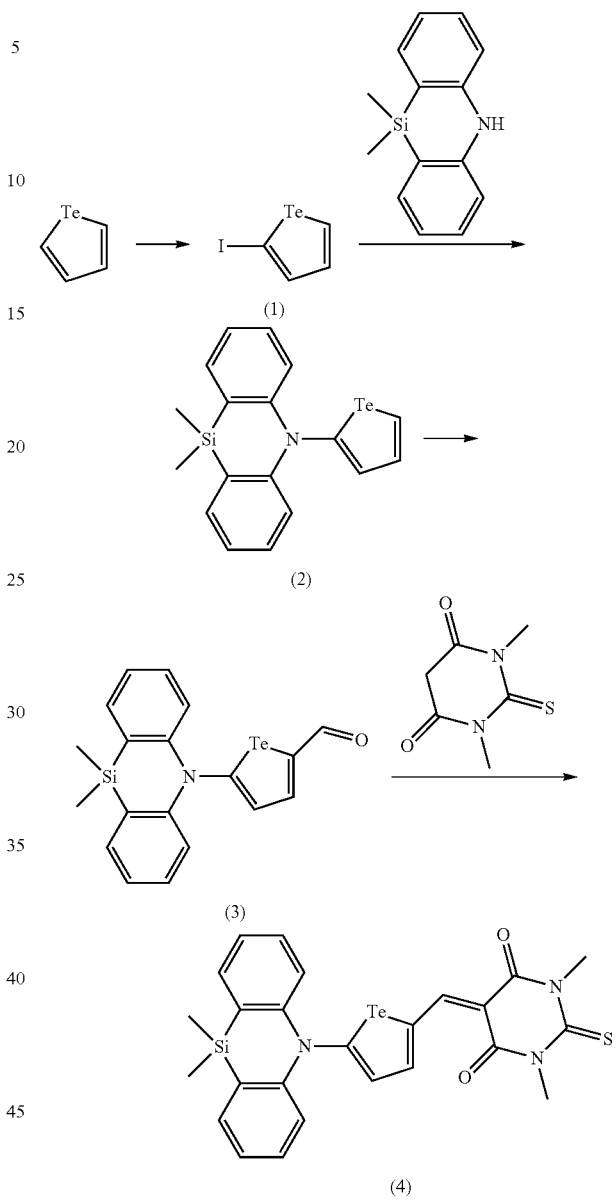

(i) Synthesis of Compound (1)

2-iodotellurophene is synthesized referring to the method disclosed in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (2)

15.0 g (49.1 mmol) of 2-iodotellurophene and 10.0 g (44.6 mmol) of 10,10-dimethyl-5,10-dihydrodibenzo[b,e][1,4]azasiline are heated and refluxed for 2 hours in 200 ml of anhydrous toluene in the presence of 2.23 mmol of Pd(dba)$_2$, 2.23 mmol of P(tBu)$_3$, and 12.9 g (133.9 mmol) of NaOtBu. A product obtained therefrom is separated and purified through silica gel column chromatography (toluene:hexane=1:4 in a volume ratio) to obtain 6.8 g of 10,10-dimethyl-5-(tellurophen-2-yl)-5,10-dihydrodibenzo[b,e][1,4]azasiline (Yield: 37.8%).

(iii) Synthesis of Compound (3)

6.2 ml of phosphoryl chloride is added in a dropwise fashion to 30.0 ml of N,N-dimethylformamide at −15° C., and the mixture is stirred at room temperature (24° C.) for 2 hours. The resultant therefrom is slowly added in a dropwise fashion to a mixture of 300 ml of dichloromethane and 6.8 g of Compound (2) at −15° C., and the obtained mixture is stirred at room temperature for 30 minutes and concentrated under a reduced pressure. 300 ml of water is added thereto, an aqueous sodium hydroxide solution is added thereto until pH becomes 14, and the obtained mixture is stirred at room temperature (24° C.) for 2 hours. An organic layer extracted therefrom by using dichloromethane is washed with an aqueous sodium chloride solution and then, dried by adding magnesium sulfate anhydrous thereto. A product obtained therefrom is separated and purified through silica gel column chromatography (hexane:ethylacetate=4:1 in a volume ratio) to obtain 2.82 g (Yield: 38.8%) of 5-(10,10-dimethyldibenzo[b,e][1,4]azasilin-5(10H)-yl) tellurophene-2-carbaldehyde.

(iv) Synthesis of Compound (4) Represented by Chemical Formula 2-4

2.82 g (6.54 mmol) of Compound (3) is suspended in ethanol, 1.35 g (7.85 mmol) of 1,3-dimethyl-2-thiobarbituric acid synthesized according to a method described in J. Pharmacol., 1944, 82, 292, p. 4417 is added thereto, and the mixture is reacted at 50° C. for 2 hours to obtain 2.98 g of the compound represented by Chemical Formula 2-4 (Yield: 77.8%). The obtained compound is sublimed and purified up to purity of 99.9%.

$^1$H-NMR (500 MHz, Methylene Chloride-$d_2$): δ 8.46 (s, 1H), 8.26 (d, 1H), 7.80 (d, 2H), 7.71 (d, 2H), 7.54 (t, 2H), 7.42 (t, 2H), 6.93 (d, 1H), 3.68 (d, 6H), 0.45 (s, 6H).

Evaluation 1: Light Absorption Characteristics of Compounds

Light absorption characteristics (maximum absorption wavelength and full width at half maximum (FWHM)) of the compounds according to Synthesis Examples 1 to 5 are evaluated. Each compound according to Synthesis Examples 1 to 5 and C60 are codeposited in a volume ratio of 1:1 to provide each thin film. Light absorption characteristics of each film are evaluated by using an ultraviolet (UV)-visible ray (UV-Vis) with Cary 5000 UV Spectroscopy (Varian Medical Systems). The results are shown in Table 1.

TABLE 1

| Compounds | Chemical Formula | $\lambda_{max}$ (nm) | FWHM (nm) |
|---|---|---|---|
| Synthesis Example 1 | | 536 | 78 |
| Synthesis Example 2 | | 550 | 99 |
| Synthesis Example 3 | | 550 | 112 |

TABLE 1-continued

| Compounds | Chemical Formula | $\lambda_{max}$ (nm) | FWHM (nm) |
|---|---|---|---|
| Synthesis Example 4 | (structure) | 550 | 98 |
| Synthesis Example 5 | (structure) | 538 | 108 |

Referring to Table 1, maximum absorption wavelengths of the compounds according to Synthesis Examples 1 to 5 are in a green wavelength region and full widths at half maximum (FWHM) thereof are narrow. Accordingly, the compounds according to Synthesis Examples 1 to 5 exhibit improved absorption selectivity in the green wavelength region.

Evaluation 2: Thermal Stability of Compounds

In order to evaluate thermal stability of the compounds according to Synthesis Examples 1 to 5, a deposition temperature (Ts10) where 10 wt % of each compound at 10 Pa is decomposed and a deposition temperature (Ts50) where 50 wt % of each compound at 10 Pa is decomposed are measured. The deposition temperatures are measured using a thermal gravimetric analysis (TGA) method. The results are shown in Table 2.

TABLE 2

| | Chemical Formula Nos. | Tm (° C.) | $T_{S10}$ (10 wt %, 10 Pa) (° C.) | $T_{S50}$ (50 wt %, 10 Pa) (°C) | ΔT (Tm-$T_{S10}$) (° C.) |
|---|---|---|---|---|---|
| Synthesis Example 1 | Chemical Formula 1-1 | 211 | 184 | 208 | 27 |
| Synthesis Example 2 | Chemical Formula 1-2 | 298 | 221 | 248 | 77 |
| Synthesis Example 3 | Chemical Formula 1-3 | 362 | 270 | 305 | 92 |
| Synthesis Example 4 | Chemical Formula 1-4 | 350 | 247 | 275 | 103 |
| Synthesis Example 5 | Chemical Formula 1-5 | 322 | 231 | 262 | 91 |

When a compound has a lower melting point than a deposition temperature during the vacuum deposition, the compound may decompose and simultaneously gasify, and thus may fail to form into a film. Accordingly, the melting point of a compound desirably may be higher than the deposition temperature. Referring to Table 2, the compounds according to Synthesis Examples 1 to 5 exhibit a higher melting point than a deposition temperature by greater than or equal to 27° C. Accordingly, the compounds according to Synthesis Examples 1 to 5 have a large difference between the melting point and the deposition temperature and thus may secure process stability.

Example 1: Manufacture of Photoelectric Device

An about 150 nm-thick anode is formed by sputtering ITO on a glass substrate, and a 100 nm-thick active layer is formed thereon by codepositing a compound represented by Chemical Formula 1-1 according to Synthesis Example 1 (p-type semiconductor compound) and C60 (n-type semiconductor compound) in a volume ratio of 1:1. Subsequently, a 10 nm-thick molybdenum oxide ($MoO_x$, 0<x≤3) thin film is formed thereon as a charge auxiliary layer. On the molybdenum oxide thin film, a 7 nm-thick cathode is formed by sputtering ITO, manufacturing an organic photoelectric device.

Examples 2 to 5: Manufacture of Photoelectric Device

Photoelectric devices according to Examples 2 to 5 are manufactured according to the same method as Example 1 except that the compounds according to Synthesis Examples 2 to 5 are used respectively instead of the compound according to Synthesis Example 1.

Reference Examples 1 to 4: Manufacture of Photoelectric Device

Photoelectric devices according to Reference Examples 1 to 4 are manufactured according to the same method as Example 1 except that the compounds according to Reference Synthesis Example 1 to 4 are used respectively instead of the compound according to Synthesis Example 1.

Evaluation 3: Light Absorption Characteristics of Photoelectric Device

Light absorption characteristics in an ultraviolet (UV)-visible (UV-Vis) region of each photoelectric device according to Examples 1 to 5 are evaluated using Cary 5000 UV Spectroscopy (Varian Medical Systems). The results of Examples 1, 3, and 5 are shown in Table 3.

TABLE 3

| Example | $\lambda_{max}$ (nm) | FWHM (nm) |
|---|---|---|
| Example 1 | 545 | 78 |
| Example 3 | 550 | 112 |
| Example 5 | 540 | 108 |

Referring to Table 3, the photoelectric devices according to Examples 1, 3, and 5 exhibit maximum absorption wavelength (Amax) at greater than or equal to 540 nm and a low full width at half maximum (FWHM). Accordingly, the photoelectric devices according to Examples 1, 3, and 5 exhibit high wavelength selectivity in a green wavelength region.

Evaluation 4: EQE of Photoelectric Device

External quantum efficiency of the photoelectric devices according to Example 1 to 5 is evaluated. The external quantum efficiency (EQE) is measured by using an IPCE measurement system (McScience Inc., Korea). The EQE is measured at a wavelength ranging from about 350 nm to about 750 nm by calibrating IPCE measurement system with the Si photodiode (Hamamatsu Photonics K.K., Japan) and respectively mounting the organic photoelectric devices according to Examples 1 to 5. In Table 3, the external quantum efficiency is measured at a maximum light absorption wavelength when a −3V voltage is applied thereto. In addition, the photoelectric devices according to Examples 1 to 5 are annealed at 160° C. for 3 days and then, measured with respect to EQE in the same method. The results of Examples 3 and 5 are shown in Table 4.

TABLE 4

| Examples | EQE (%) at −3 V | EQE (%) at −3 V (160° C., 3 h) |
|---|---|---|
| Example 3 | 48 | 53 |
| Example 5 | 49 | 58 |

Referring to Table 4, the photoelectric devices according to Examples 3 and 5 exhibit excellent EQE at room temperature and also, excellent EQE after the annealing at 160° C. Accordingly, the photoelectric devices exhibit excellent thermal stability.

Evaluation 5: Mobility of Photoelectric Device

Mobility of the photoelectric devices according to Examples 1 to 5 and Reference Examples 1 to 4 is evaluated by radiating light of 550 nm (a laser pulse (pulse width: 6 nm) thereinto and applying a bias (V) voltage thereto and then, measuring photocurrents thereof. Subsequently, time (t) when the photocurrents are maximized is measured and put in Equation 2 to calculate the mobility (p).

$$\mu = \frac{T^2}{t \times V}$$ [Equation 2]

In Equation 2, T denotes a thickness of an active layer, t denotes time when a photocurrent is maximized, and V is a voltage applied thereto.

The results of Examples 3 and 5 are shown in Table 5.

TABLE 5

| Example | Mobility (cm$^2$/V · sec) |
|---|---|
| Example 3 | $5.00 \times 10^{-6}$ |
| Example 5 | $2.00 \times 10^{-6}$ |

Referring to Table 5, the photoelectric devices according to Examples 3 and 5 have excellent mobility.

While this disclosure has been described in connection with what is presently considered to be practical example embodiments, it is to be understood that inventive concepts are not limited to the disclosed embodiments, but, on the contrary, are intended to cover various modifications and equivalent arrangements included within the spirit and scope of the appended claims.

DESCRIPTION OF SYMBOLS

| | |
|---|---|
| 10: first electrode | 20: second electrode |
| 30: active layer | 40, 45: charge auxiliary layer |
| 100, 200: photoelectric device | |
| 300, 400, 500, 600: organic CMOS image sensor | |
| 310: semiconductor substrate | |
| 70B, 72B: blue filter 70R, 72R: red filter | |
| 70, 72: color filter layer | 85: through-hole |
| 60: lower insulation layer | 80: upper insulation layer |
| 50B, 50R: photo-sensing device | 55: charge storage |

What is claimed is:

1. A compound represented by Chemical Formula 1:

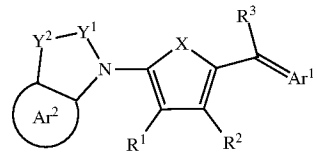

[Chemical Formula 1]

wherein, in Chemical Formula 1,

Ar$^1$ is a substituted or unsubstituted C6 to C30 hydrocarbon cyclic group having at least one functional group selected from C═O, C═S, C═Se, and C═Te, a substituted or unsubstituted C6 to C30 heterocyclic group having at least one functional group selected from C═O, C═S, C═Se, and C═Te, or a fused ring thereof, Ar² is a substituted or unsubstituted C6 to C30 arene group, a substituted or unsubstituted C3 to C30 heteroarene group, or a condensed ring thereof, X is —O—, —S—, —Se—, —Te—, —S(=O)—, —S(=O)₂—, —NRᵃ—, —SiRᵇRᶜ—, —GeRᵈRᵉ—, —(CRᶠRᵍ)—, or —(C(Rʰ)=C(Rⁱ))—, wherein Rᵃ, Rᵇ, Rᶜ, Rᵈ, Rᵉ, Rᵈ, Rᵉ, Rᶠ, Rᵍ, Rʰ, and Rⁱ are independently hydrogen or a substituted or unsubstituted C1 to C10 alkyl group, and n is an integer of 1 or 2, R¹ to R³ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —SiRᵃRᵇRᶜ (wherein Rᵃ, Rᵇ and Rᶜ are independently hydrogen or a substituted or unsubstituted C1 to C10 alkyl group), or a combination thereof, and Y¹ and Y² are independently —NRᵃ¹—, —N=, —O—, —S—, —Se—, —Te—, —(CRᵃ²)=, or —(CRᵃ³Rᵃ⁴)ₙ—, provided that both Y¹ and Y² are not —NRᵃ¹—, —N=, —O—, —S—, —Se—, or —Te—, or —Y¹-Y²— is —(C(Rᵃ⁵)=C(Rᵃ⁶))—, wherein Rᵃ¹, Rᵃ², Rᵃ³, Rᵃ⁴, Rᵃ⁵, and Rᵃ⁶ are independently hydrogen or a C1 to C10 alkyl group, and n is an integer of 1 or 2.

2. The compound of claim 1, wherein in Chemical Formula 1, the fused ring of the Ar² ring and the N—Y¹-Y²-containing ring is represented by Chemical Formula 2A:

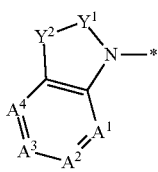

[Chemical Formula 2A]

wherein, in Chemical Formula 2A,

Y¹ and Y² are independently —NRᵃ¹—, —N=, —O—, —S—, —Se—, —Te—, —(CRᵃ²)=, or —(CRᵃ³Rᵃ⁴)ₙ—, provided that both Y¹ and Y² are not —NRᵃ¹—, —N=, —O—, —S—, —Se—, or —Te—, or —Y¹-Y²— is —(C(Rᵃ⁵)=C(Rᵃ⁶))—, wherein Rᵃ¹, Rᵃ², Rᵃ³, Rᵃ⁴, Rᵃ⁵, and Rᵃ⁶ are independently hydrogen or a C1 to C10 alkyl group, and n is an integer of 1 or 2, and A¹ to A⁴ are independently N or CRˣ, wherein Rˣ is hydrogen, a halogen, a cyano group, or a substituted or an unsubstituted C1 to C10 alkyl group.

3. The compound of claim 2, wherein at least one of A¹ to A⁴ in Chemical Formula 2A is N.

4. The compound of claim 2, wherein in Chemical Formula 2A, two of A¹ to A⁴ that are adjacent to each other are linked to each other to provide a fused aromatic ring.

5. The compound of claim 2, wherein Chemical Formula 2A is represented by one of Chemical Formulas 2A-1 to 2A-5:

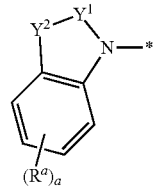

[Chemical Formula 2A-1]

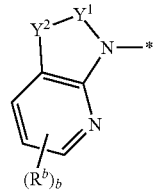

[Chemical Formula 2A-2]

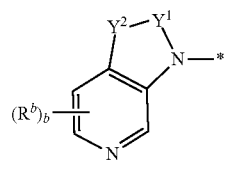

[Chemical Formula 2A-3]

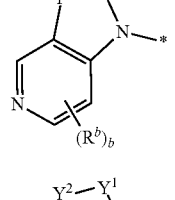

[Chemical Formula 2A-4]

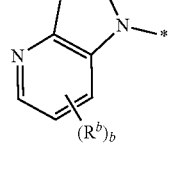

[Chemical Formula 2A-5]

wherein, in Chemical Formulas 2A-1 to 2A-5,

Y¹ and Y² are independently —NRᵃ¹—, —N=, —O—, —S—, —Se—, —Te—, —(CRᵃ²)=, or —(CRᵃ³Rᵃ⁴)ₙ—, provided that both Y¹ and Y² are not —NRᵃ¹—, —N=, —O—, —S—, —Se—, or —Te—, or —Y¹-Y²— is —(C(Rᵃ⁵)=C(Rᵃ⁶))—, wherein Rᵃ¹, Rᵃ², Rᵃ³, Rᵃ⁴, Rᵃ⁵, and Rᵃ⁶ are independently hydrogen or a C1 to C10 alkyl group, and n is an integer of 1 or 2, and Rᵃ is hydrogen or a substituted or unsubstituted C1 to C10 alkyl group, a is an integer of 1 to 4, Rᵇ is hydrogen or a substituted or unsubstituted C1 to C10 alkyl group, and b is an integer of 1 to 3.

6. The compound of claim 2, wherein Chemical Formula 2A is represented by one of Chemical Formulas 2A-6 to 2A-10:

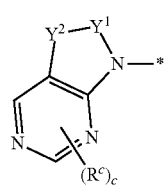

[Chemical Formula 2A-6]

-continued

[Chemical Formula 2A-7]

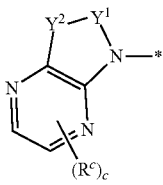

[Chemical Formula 2A-8]

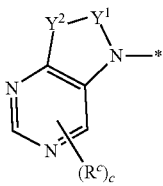

[Chemical Formula 2A-9]

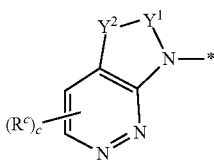

[Chemical Formula 2A-10]

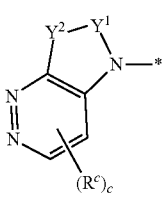

wherein, in Chemical Formulas 2A-6 to 2A-10, $Y^1$ and $Y^2$ are independently —$NR^{a1}$—, —N═, —O—, —S—, —Se—, —Te—, —($CR^{a2}$)═, or —($CR^{a3}R^{a4}$)$_n$—, provided that both $Y^1$ and $Y^2$ are not —$NR^{a1}$—, —N═, —O—, —S—, —Se—, or —Te—, or —$Y^1$-$Y^2$— is —(C($R^{a5}$)═C($R^{a6}$))—, wherein $R^{a1}$, $R^{a2}$, $R^{a3}$, $R^{a4}$, $R^{a5}$, and $R^{a6}$ are independently hydrogen or a C1 to C10 alkyl group, and n is an integer of 1 or 2, and $R^c$ is hydrogen or a substituted or unsubstituted C1 to C10 alkyl group, and c is an integer of 1 or 2.

7. The compound of claim 1, wherein in Chemical Formula 1, the fused ring of the $Ar^2$ ring and the N—$Y^1$-$Y^2$-containing ring is represented by Chemical Formula 2B:

[Chemical Formula 2B]

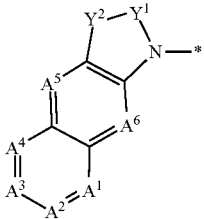

wherein, in Chemical Formula 2B, $Y^1$ and $Y^2$ are independently —$NR^{a1}$—, —N═, —O—, —S—, —Se—, —Te—, —($CR^{a2}$)═, or —($CR^{a3}R^{a4}$)$_n$—, provided that both $Y^1$ and $Y^2$ are not —$NR^{a1}$—, —N═, —O—, —S—, —Se—, or —Te—, or —$Y^1$-$Y^2$— is —(C($R^{a5}$)═C($R^{a6}$))—, wherein $R^{a1}$, $R^{a2}$, $R^{a3}$, $R^{a4}$, $R^{a5}$, and $R^{a6}$ are independently hydrogen or a C1 to C10 alkyl group, and n is an integer of 1 or 2, and $A^1$ to $A^6$ are independently N or $CR^x$, wherein $R^x$ is hydrogen, a halogen, a cyano group, or a substituted or an unsubstituted C1 to C10 alkyl group.

8. The compound of claim 7, wherein at least one of $A^1$ to $A^6$ in Chemical Formula 2B is N.

9. The compound of claim 7, wherein in Chemical Formula 2B, two of $A^1$ to $A^4$ that are adjacent to each other are linked to each other to provide a fused aromatic ring.

10. The compound of claim 7, wherein Chemical Formula 2B is represented by one of Chemical Formulas 2B-1 to 2B-5:

[Chemical Formula 2B-1]

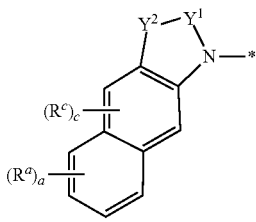

[Chemical Formula 2B-2]

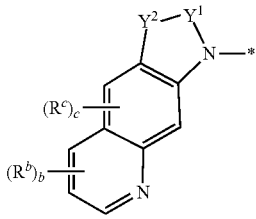

[Chemical Formula 2B-3]

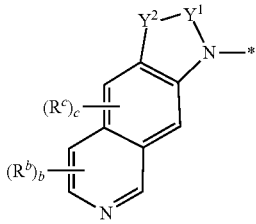

[Chemical Formula 2B-4]

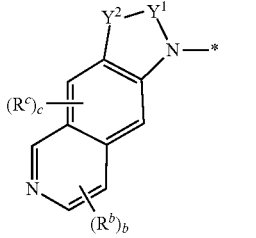

[Chemical Formula 2B-5]

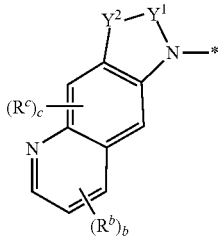

wherein, in Chemical Formulas 2B-1 to 2B-5, $Y^1$ and $Y^2$ are independently —$NR^{a1}$—, —N═, —O—, —S—, —Se—, —Te—, —($CR^{a2}$)═, or —($CR^{a3}R^{a4}$)$_n$—, provided that both $Y^1$ and $Y^2$ are not —$NR^{a1}$—, —N═, —O—, —S—, —Se—, or —Te—, or —$Y^1$-$Y^2$— is —(C($R^{a5}$)═C($R^{a6}$))—, wherein $R^{a1}$, $R^{a2}$, $R^{a3}$, $R^{a4}$, $R^{a5}$, and $R^{a6}$ are independently hydrogen or a C1 to C10 alkyl group, and n is an integer of 1 or 2, and
$R^a$ is hydrogen or a substituted or unsubstituted C1 to C10 alkyl group,
a is an integer of 1 to 4,
$R^b$ is hydrogen or a substituted or unsubstituted C1 to C10 alkyl group,
b is an integer of 1 to 3,
$R^c$ is hydrogen or a substituted or unsubstituted C1 to C10 alkyl group, and
c is an integer of 1 or 2.

11. The compound of claim 7, wherein Chemical Formula 2B is represented by one of Chemical Formulas 2B-6 to 2B-10:

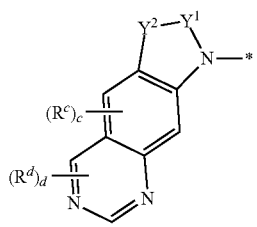

[Chemical Formula 2B-6]

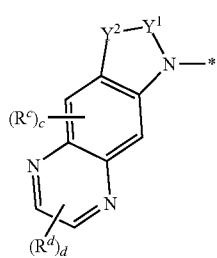

[Chemical Formula 2B-7]

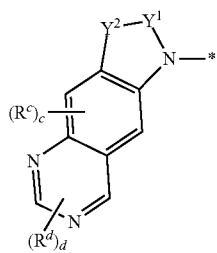

[Chemical Formula 2B-8]

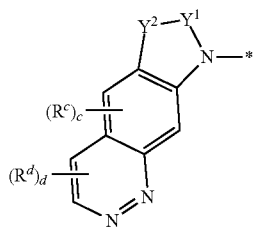

[Chemical Formula 2B-9]

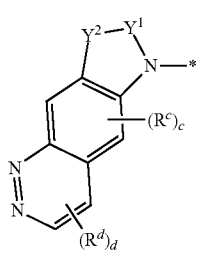

[Chemical Formula 2B-10]

wherein, in Chemical Formulas 2B-6 to 2B-10,
$Y^1$ and $Y^2$ are independently —$NR^{a1}$—, —N=, —O—, —S—, —Se—, —Te—, —$(CR^{a2})$=, or —$(CR^{a3}R^{a4})_n$—, provided that both $Y^1$ and $Y^2$ are not —$NR^{a1}$—, —N=, —O—, —S—, —Se—, or —Te—, or —$Y^1$-$Y^2$— is —$(C(R^{a5})=C(R^{a6}))$—, wherein $R^{a1}$, $R^{a2}$, $R^{a3}$, $R^{a4}$, $R^{a5}$, and $R^{a6}$ are independently hydrogen or a C1 to C10 alkyl group, and n is an integer of 1 or 2, and
$R^c$ is hydrogen or a substituted or unsubstituted C1 to C10 alkyl group,
c is an integer of 1 or 2,
$R^d$ is hydrogen or a substituted or unsubstituted C1 to C10 alkyl group, and
d is an integer of 1 or 2.

12. The compound of claim 1, wherein $Ar^1$ is a cyclic group represented by Chemical Formula 3:

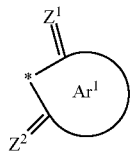

[Chemical Formula 3]

wherein, in Chemical Formula 3,
$Ar^1$ is a substituted or unsubstituted C6 to C30 aryl group or a substituted or unsubstituted C3 to C30 heteroaryl group,
$Z^1$ is O, S, Se, or Te, and
$Z^2$ is O, S, Se, Te, or $CR^aR^b$, wherein $R^a$ and $R^b$ are independently hydrogen, a substituted or unsubstituted C1 to C10 alkyl group, a cyano group or a cyano-containing group, provided that when $Z^2$ is $CR^aR^b$, at least one of $R^a$ and $R^b$ is a cyano group or a cyano-containing group.

13. The compound of claim 1, wherein in Chemical Formula 1, $Ar^1$ is a cyclic group represented by one of Chemical Formula 4A to Chemical Formula 4F:

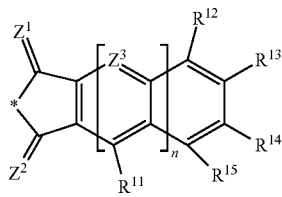

[Chemical Formula 4A]

wherein, in Chemical Formula 4A,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group or a cyano-containing group, provided that when $Z^2$ is $CR^aR^b$, at least one of $R^a$ and $R^b$ is a cyano group or a cyano-containing group,
$Z^3$ is N or $CR^c$, wherein $R^c$ is hydrogen, deuterium, or a substituted or unsubstituted C1 to C10 alkyl group,
$R^{11}$, $R^{12}$, $R^{13}$, $R^{14}$, and $R^{15}$ are the same or different and are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, or $R^{12}$ and $R^{13}$ and $R^{14}$ and $R^{15}$ are independently present and are linked to each other to provide a fused aromatic ring, n is 0 or 1, and

* is a linking point,

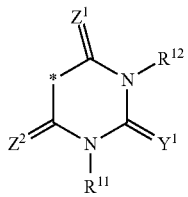

[Chemical Formula 4B]

wherein, in Chemical Formula 4B, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group or a cyano-containing group, provided that when $Z^2$ is $CR^aR^b$, at least one of $R^a$ and $R^b$ is a cyano group or a cyano-containing group, $Y^1$ is O, S, Se, Te, or $C(R^a)(CN)$, wherein $R^a$ is hydrogen, a cyano group (—CN), or a C1 to C10 alkyl group, $R^{11}$ and $R^{12}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking point,

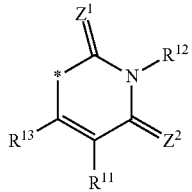

[Chemical Formula 4C]

wherein, in Chemical Formula 4C, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group or a cyano-containing group, provided that when $Z^2$ is $CR^aR^b$, at least one of $R^a$ and $R^b$ is a cyano group or a cyano-containing group, $R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking point,

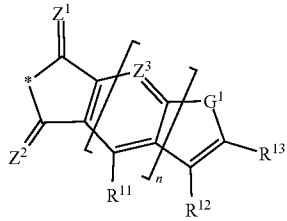

[Chemical Formula 4D]

wherein, in Chemical Formula 4D, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group or a cyano-containing group, provided that when $Z^2$ is $CR^aR^b$, at least one of $R^a$ and $R^b$ is a cyano group or a cyano-containing group, $Z^3$ is N or $CR^c$, wherein $R^c$ is hydrogen or a substituted or unsubstituted C1 to C10 alkyl group, $G^1$ is —O—, —S—, —Se—, —Te—, —$SiR^xR^y$—, or —$GeR^zR^w$—, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group, $R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, wherein $R^{12}$ and $R^{13}$ independently are present or are linked to each other to provide a fused aromatic ring, n is 0 or 1, and

* is a linking point,

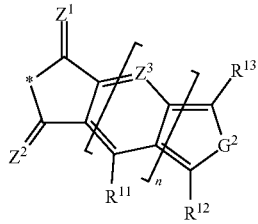

[Chemical Formula 4E]

wherein, in Chemical Formula 4E, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group or a cyano-containing group, provided that when $Z^2$ is $CR^aR^b$, at least one of $R^a$ and $R^b$ is a cyano group or a cyano-containing group, $Z^3$ is N or $CR^c$, wherein $R^c$ is hydrogen or a substituted or unsubstituted C1 to C10 alkyl group, $G^2$ is —O—, —S—, —Se—, —Te—, —$SiR^xR^y$—, or —$GeR^zR^w$—, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group, $R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, n is 0 or 1, and

* is a linking point,

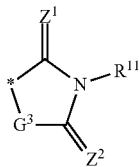

[Chemical Formula 4F]

wherein, in Chemical Formula 4F, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group or a cyano-containing group, provided that when $Z^2$ is $CR^aR^b$, at least one of $R^a$ and $R^b$ is a cyano group or a cyano-containing group, $R^{11}$ is hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and $G^3$ is —O—, —S—, —Se—, —Te—, —$SiR^xR^y$—, or —$GeR^zR^w$—, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group.

14. The compound of claim 13, wherein $Z^1$ and $Z^2$ are the same in Chemical Formula 4A to Chemical Formula 4F.

15. The compound of claim 13, wherein $Z^1$ and $Z^2$ are different in Chemical Formula 4A to Chemical Formula 4F.

16. The compound of claim 13, wherein
$Ar^1$ in Chemical Formula 1 is represented by one of Chemical Formula 4A, Chemical Formula 4D, or Chemical Formula 4E, and
n is 0 in Chemical Formula 4A, Chemical Formula 4D, and Chemical Formula 4E.

17. The compound of claim 13, wherein
$Ar^1$ in Chemical Formula 1 is represented by one of Chemical Formula 4A, Chemical Formula 4D, or Chemical Formula 4E, and
n is 1 in Chemical Formula 4A, Chemical Formula 4D, and Chemical Formula 4E.

18. The compound of claim 1, wherein the compound has a maximum absorption wavelength ($\lambda_{max}$) in a wavelength region of greater than or equal to about 500 nm and less than or equal to about 600 nm, in a thin film state.

19. The compound of claim 1, wherein the compound exhibits a light absorption curve having a full width at half maximum (FWHM) of about 50 nm to about 120 nm, in a thin film state.

20. The compound of claim 1, wherein a difference between a melting point of the compound and a temperature at which 10% by weight of an initial weight is lost (deposition temperature) is greater than or equal to about 10° C.

21. The compound of claim 1, wherein
$R^1$ to $R^3$ in Chemical Formula 1 are independently hydrogen, deuterium, or a substituted or unsubstituted C1 to C30 alkyl group, and
X in Chemical Formula 1 is Se or Te.

22. A photoelectric device, comprising:
a first electrode and a second electrode facing each other, and
an active layer between the first electrode and the second electrode,
the active layer comprising the compound of claim 1.

23. An image sensor comprising:
the photoelectric device of claim 22.

24. The image sensor of claim 23, further comprising:
a semiconductor substrate integrated with a plurality of first photo-sensing devices configured to sense light in a blue wavelength region and a plurality of second photo-sensing devices configured to sense light in a red wavelength region, wherein
the photoelectric device is on the semiconductor substrate and selectively configured to sense light in a green wavelength region.

25. The image sensor of claim 24, further comprising:
a color filter layer comprising a blue filter configured to selectively transmit light in a blue wavelength region and a red filter configured to selectively transmit light in a red wavelength region, wherein
the color filter layer is on the semiconductor substrate.

26. The image sensor of claim 24, wherein the plurality of first photo-sensing devices and the plurality of second photo-sensing devices are stacked in a vertical direction in the semiconductor substrate.

27. The image sensor of claim 23, further comprising:
an organic photoelectric device including the photoelectric device;
a blue photoelectric device configured to selectively absorb light in a blue wavelength region; and
a red photoelectric device configured to selectively absorb light in a red wavelength region,
wherein the organic photoelectric device is a green photoelectric device, and
the organic photoelectric device, the blue photoelectric device, and the red photoelectric device are stacked.

28. An electronic device comprising:
the image sensor of claim 23.

* * * * *